US 7,176,013 B2

United States Patent
Wu

(10) Patent No.: US 7,176,013 B2
(45) Date of Patent: Feb. 13, 2007

(54) MODIFIED CORIN MOLECULES HAVING SUBSTITUTE ACTIVATION SEQUENCES AND USES THEREOF

(75) Inventor: Qingyu Wu, Lafayette, CA (US)

(73) Assignee: Schering Aktiengesellschaft, Berlin (DE)

( * ) Notice: Subject to any disclaimer, the term of this patent is extended or adjusted under 35 U.S.C. 154(b) by 93 days.

(21) Appl. No.: 10/865,978

(22) Filed: Jun. 9, 2004

(65) Prior Publication Data

US 2005/0003416 A1  Jan. 6, 2005

Related U.S. Application Data

(60) Provisional application No. 60/477,683, filed on Jun. 11, 2003.

(51) Int. Cl.
  C12N 9/64   (2006.01)
  C12N 15/57  (2006.01)
  C12N 15/62  (2006.01)
  C12N 15/79  (2006.01)
  A61K 38/48  (2006.01)

(52) U.S. Cl. ............... 435/226; 435/69.1; 435/69.7; 435/252.3; 435/320.1; 435/975; 424/94.64; 536/23.2; 536/23.4

(58) Field of Classification Search .............. None
See application file for complete search history.

(56) References Cited

U.S. PATENT DOCUMENTS

| 5,869,637 | A  |   | 2/1999  | Au-Young et al. | 536/235  |
|-----------|----|---|---------|-----------------|----------|
| 5,968,782 | A  | * | 10/1999 | Stevens         | 435/69.7 |
| 6,479,274 | B1 |   | 11/2002 | Antalis et al.  | 435/252.3 |
| 6,906,176 | B2 | * | 6/2005  | Ley et al.      | 530/350  |

| 2003/0211997 | A1 | * | 11/2003 | Kim et al.   | 514/12  |
|--------------|----|---|---------|--------------|---------|
| 2004/0132156 | A1 | * | 7/2004  | Parry et al. | 435/226 |

FOREIGN PATENT DOCUMENTS

| EP | 0 292 009 A1 | * | 11/1988 |
|----|--------------|---|---------|
| EP | 0927764      |   | 7/1999  |
| WO | WO 99/10503  |   | 3/1999  |
| WO | WO99/64608   |   | 12/1999 |
| WO | WO 01/16289  |   | 3/2001  |
| WO | WO 01/57194  |   | 8/2001  |
| WO | WO 03/035861 | * | 5/2003  |

OTHER PUBLICATIONS

Yan et al., "Corin, A Mosaic Transmembrane Serine Protease Encoded by a Novel cDNA from Human Heart", J. Biol. Chem. (1999) 274:14926-14935.
Yan et al., "Corin, A Transmembrane Cardiac Serine-Protease Acts as a Pro-Atrial Natriuretic Peptide-Converting Enzyme", Proc. Natl. Acad. Sci. USA (2000) 97:8525-8529.
Wu et al., "Processing of Pro-Atrial Natriuretic Peptide by Corin in Cardiac Myocytes", J. Biol. Chem. (2002) 277:16900-16905.
Hooper, J.D., "Type II Transmembrane Serine Proteases", The Journal of Biological Chemistry, vol. 276, No. 2, Issue of Jan. 12, pp. 857-860, 2001.

* cited by examiner

Primary Examiner—Nashaat T. Nashed
Assistant Examiner—William W. Moore
(74) Attorney, Agent, or Firm—Berlex Inc.

(57) ABSTRACT

This invention relates to novel modified corin molecules, or fragments or derivatives thereof, comprising a substitute activation sequence. The modified corin molecules are cleaved at the substitute activation sequence, thereby generating activated corin molecules, or fragments or derivatives thereof, that exhibit the functional activity of naturally occurring, wild-type corin molecules. The modified corin molecules can be used to treat a variety of diseases or disorders, including congestive heart failure and acute myocardial infarction.

22 Claims, 12 Drawing Sheets

Transmembrane Corin Deletion Mutants

TM = Transmembrane domain, LDLR = Low density lipoprotein receptor, CRD = Frizzled-like cysteine-rich domain,
SRCR = Scavenger receptor cysteine-rich domain, CAT = Serine protease domain

FIGURE 1

```
   1 ATGAAACAGTCTCCTGCCCTCGCTCCGGAAGAGCGCTACCGCAGAGCCGGGTCCCCAAAG
     CCGGTCTTGAGAGCTGATGACAATAACATGGGCAATGGCTGCTCTCAGAAGCTGGCGACT
 121 GCTAACCTCCTCCGGTTCCTATTGCTGGTCCTGATTCCATGTATCTGTGCTCTCGTTCTC
 181 TTGCTGGTGATCCTGCTTTCCTATGTTGGAACATTACAAAAGGTCTATTTTAAATCAAAT
 241 GGGAGTGAACCTTTGGTCACTGATGGTGAAATCCAAGGGTCCGATGTTATTCTTACAAAT
 301 ACAATTTATAACCAGAGCACTGTGGTGTCTACTGCACATCCCGACCAACACGTTCCAGCC
 361 TGGACTACGGATGCTTCTCTCCCAGGGGACCAAAGTCACAGGAATACAAGTGCCTGTATG
 421 AACATCACCCACAGCCAGTGTCAGATGCTGCCCTACCACGCCACGCTGACACCTCTCCTC
 481 TCAGTTGTCAGAAACATGGAAATGGAAAAGTTCCTCAAGTTTTTCACATATCTCCATCGC
 541 CTCAGTTGCTATCAACATATCATGCTGTTTGGCTGTACCCTCGCCTTCCCTGAGTGCATC
 601 ATTGATGGCGATGACAGTCATGGACTCCTGCCCTGTAGGTCCTTCTGTGAGGCTGCAAAA
 661 GAAGGCTGTGAATCAGTCCTGGGGATGGTGAATTACTCCTGGCCGGATTTCCTCAGATGC
 721 TCCCAGTTTAGAAACCAAACTGAAAGCAGCAATGTCAGCAGAATTTGCTTCTCACCTCAG
 781 CAGGAAAACGGAAAGCAATTGCTCTGTGGAAGGGGTGAGAACTTTCTGTGTGCCAGTGGA
 841 ATCTGCATCCCCGGGAAACTGCAATGTAATGGCTACAACGACTGTGACGACTGGAGTGAC
 901 GAGGCTCATTGCAACTGCAGCGAGAATCTGTTTCACTGTCACACAGGCAAGTGCCTTAAT
 961 TACAGCCTTGTGTGTGATGGATATGATGACTGTGGGATTTGAGTGATGAGCAAACTGT
1021 GATTGCAATCCCACAACAGAGCATCGCTGCGGGGACGGGCGCTGCATCGCCATGGAGTGG
1081 GTGTGTGATGGTGACCACGACTGTGTGGATAAGTCCGACGAGGTCAACTGCTCCTGTCAC
1141 AGCCAGGGTCTGGTGGAATGCAGAAATGGACAATGTATCCCCAGCACGTTTCAATGTGAT
1201 GGTGACGAGGACTGCAAGGATGGAGTGATGAGGAGAACTGCAGCGTCATTCAGACTTCA
1261 TGTCAAGAAGGAGACCAAAGATGCCTCTACAATCCCTGCCTTGATTCATGTGGTGGTAGC
1321 TCTCTCTGTGACCCGAACAACAGTCTGAATAACTGTAGTCAATGTGAACCAATTACATTG
1381 GAACTCTGCATGAATTTGCCCTACAACAGTACAAGTTATCCAAATTATTTTGGCCACAGG
1441 ACTCAAAAGGAAGCATCCATCAGCTGGGAGTCTTCTCTTTTCCCTGCACTTGTTCAAACC
1501 AACTGTTATAAATACCTCATGTTCTTTTCTTGCACCATTTTGGTACCAAAATGTGATGTG
1561 AATACAGGCGAGCGTATCCCTCCTTGCAGGGCATTGTGTGAACACTCTAAAGAACGCTGT
1621 GAGTCTGTTCTTGGGATTGTGGCCTACAGTGGCCTGAAGACACAGATTGCAGTCAATTT
1681 CCAGAGGAAAATTCAGACAATCAAACCTGCCTGATGCCTGATGAATATGTGGAAGAATGC
1741 TCACCTAGTCATTTCAAGTGCCGCTCAGGACAGTGTGTTCTGGCTTCCAGAAGATGTGAT
1801 GGCCAGGCCGACTGTGACGATGACAGTGATGAGGAAACTGTGGTTGTAAAGAGAGAGAT
1861 CTTTGGGAATGTCCATCCAATAAACAATGTTTGAAGCACACAGTGATCTGCGATGGGTTC
1921 CCAGACTGCCCTGATTACATGGACGAGAAAAACTGCTCATTTTGCCAAGATGATGAGCTG
1981 GAATGTGCAAACCATGCGTGTGTGTCACGTGACCTGTGGTGTGATGGTGAAGCCGACTGC
2041 TCAGACAGTTCAGATGAATGGGACTGTGTGACCCTCTCTATAAATGTGAACTCCTCTTCC
2101 TTTCTGATGGTTCACAGAGCTGCCACAGAACACCATGTGTGTGCAGATGGCTGGCAGGAG
2161 ATATTGAGTCAGCTGGCCTGCAAGCAGATGGGTTTAGGAGAACCATCTGTGACCAAATTG
2221 ATACAGGAACAGGAGAAAGAGCCGCGGTGGCTGACATTACACTCCAACTGGGAGAGCCTC
2281 AATGGGACCACTTTACATGAACTTCTAGTAAATGGGCAGTCTTGTGAGAGCAGAAGTAAA
2341 ATTTCTCTTCTGTGTACTAAACAAGACTGTGGGCGCCGCCCTGCTGCCCGAATGAACAAA
2401 AGGATCCTTGGAGGTCGGACGAGTCGCCCTGGAAGGTGGCCATGGCAGTGTTCTCTGCAG
2461 AGTGAACCCAGTGGACATATCTGTGGCTGTGTCCTCATTGCCAAGAAGTGGGTTCTGACA
2521 GTTGCCCACTGCTTCGAGGGGAGAGAATGCTGCAGTTTGGAAAGTGGTGCTTGGCATC
2581 AACAATCTAGACCATCCATCAGTGTTCATGCAGACACGCTTTGTGAAGACCATCATCCTG
2641 CATCCCCGCTACAGTCGAGCAGTGGTGGACTATGACATCAGCATCGTTGAGCTGAGTGAA
2701 GACATCAGTGAGACTGGCTACGTCCGGCCTGTCTGCTTGCCCAACCCGGAGCAGTGGCTA
2761 GAGCCTGACACGTACTGCTATATCACAGGCTGGGGCCACATGGGCAATAAAATGCCATTT
2821 AAGCTGCAAGAGGGAGAGGTCCGCATTATTTCTCTGGAACATTGTCAGTCCTACTTTGAC
2881 ATGAAGACCATCACCACTCGGATGATATGTGCTGGCTATGAGTCTGGCACAGTTGATTCA
2941 TGCATGGGTGACAGCGGTGGGCCTCTTGTTTGTGAGAAGCCTGGAGGACGGTGGACATTA
3001 TTTGGATTAACTTCATGGGGCTCCGTCTGCTTTTCCAAAGTCCTGGGGCCTGGCGTTTAT
3061 AGTAATGTGTCATATTTCGTCGAATGGATTAAAAGACAGATTTACATCCAGACCTTTCTC
3121 CTAAACTAA
```

FIGURE 2

```
   1  MKQSPALAPE  ERYRRAGSPK  PVLRADDNNM  GNGCSQKLAT  ANLLRFLLLV  LIPCICALVL
  61  LLVILLSYVG  TLQKVYFKSN  GSEPLVTDGE  IQGSDVILTN  TIYNQSTVVS  TAHPDQHVPA
 121  WTTDASLPGD  QSHRNTSACM  NITHSQCQML  PYHATLTPLL  SVVRNMEMEK  FLKFFTYLHR
 181  LSCYQHIMLF  GCTLAFPECI  IDGDDSHGLL  PCRSFCEAAK  EGCESVLGMV  NYSWPDFLRC
 241  SQFRNQTESS  NVSRICFSPQ  QENGKQLLCG  RGENFLCASG  ICIPGKLQCN  GYNDCDDWSD
 301  EAHCNCSENL  FHCHTGKCLN  YSLVCDGYDD  CGDLSDEQNC  DCNPTTEHRC  GDGRCIAMEW
 361  VCDGDHDCVD  KSDEVNCSCH  SQGLVECRNG  QCIPSTFQCD  GDEDCKDGSD  EENCSVIQTS
 421  CQEGDQRCLY  NPCLDSCGGS  SLCDPNNSLN  NCSQCEPITL  ELCMNLPYNS  TSYPNYFGHR
 481  TQKEASISWE  SSLFPALVQT  NCYKYLMFFS  CTILVPKCDV  NTGERIPPCR  ALCEHSKERC
 541  ESVLGIVGLQ  WPEDTDCSQF  PEENSDNQTC  LMPDEYVEEC  SPSHFKCRSG  QCVLASRRCD
 601  GQADCDDDSD  EENCGCKERD  LWECPSNKQC  LKHTVICDGF  PDCPDYMDEK  NCSFCQDDEL
 661  ECANHACVSR  DLWCDGEADC  SDSSDEWDCV  TLSINVNSSS  FLMVHRAATE  HHVCADGWQE
 721  ILSQLACKQM  GLGEPSVTKL  IQEQEKEPRW  LTLHSNWESL  NGTTLHELLV  NGQSCESRSK
 781  ISLLCTKQDC  GRRPAARMNK  RILGGRTSRP  GRWPWQCSLQ  SEPSGHICGC  VLIAKKWVLT
 841  VAHCFEGREN  AAVWKVVLGI  NNLDHPSVFM  QTRFVKTIIL  HPRYSRAVVD  YDISIVELSE
 901  DISETGYVRP  VCLPNPEQWL  EPDTYCYITG  WGHMGNKMPF  KLQEGEVRII  SLEHCQSYFD
 961  MKTITTRMIC  AGYESGTVDS  CMGDSGGPLV  CEKPGGRWTL  FGLTSWGSVC  FSKVLGPGVY
1021  SNVSYFVEWI  KRQIYIQTFL  LN*
```

Processing of Pro-ANP by Corin Deletion Mutants

Activation of Soluble Corin by Enterokinase

FIGURE 9
Cleavage of Pro-ANP by EK-activated Soluble Corin
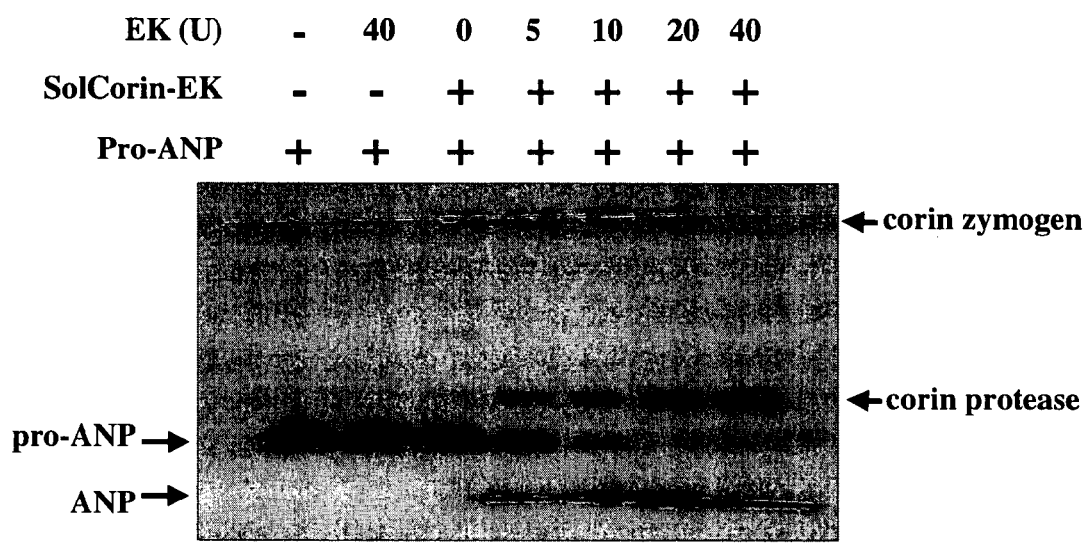
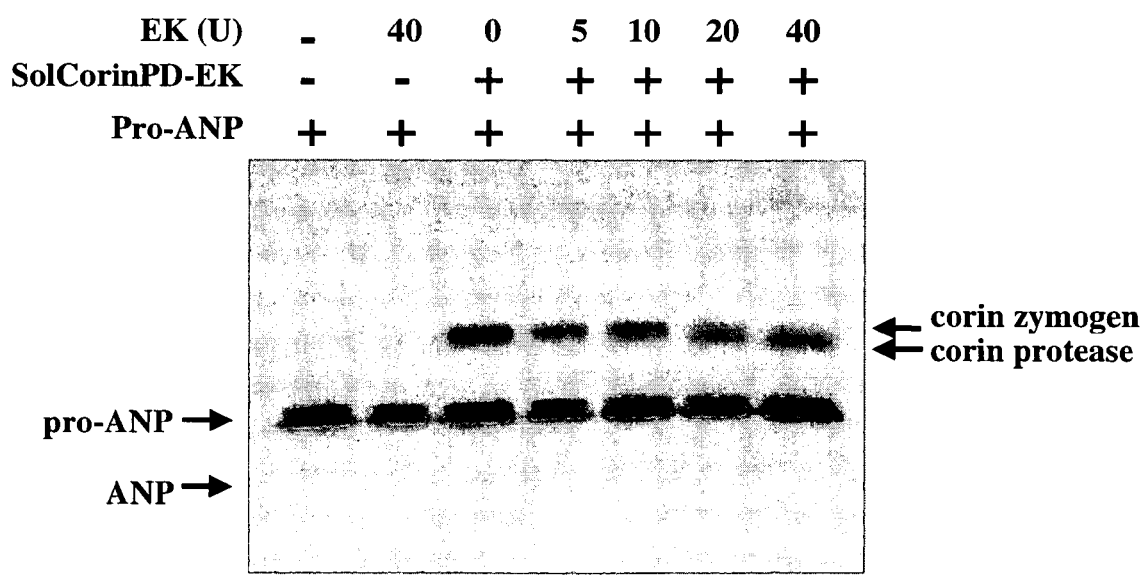

FIGURE 10

```
   1 ATGGAGACAGACACACTCCTGCTATGGGTACTGCTGCTCTGGGTTCCAGGTTCCACTGGT
  61 GACGCGGCCCAGCCGGCCAGGCGCGCGCGCCGTACGAAGCTCGCCCTTCTCGAGGATGCT
 121 TCTCTCCCAGGGGACCAAAGTCACAGGAATACAAGTGCCTGTATGAACATCACCCACAGC
 181 CAGTGTCAGATGCTGCCCTACCACGCCACGCTGACACCTCTCCTCTCAGTTGTCAGAAAC
 241 ATGGAAATGGAAAAGTTCCTCAAGTTTTTCACATATCTCCATCGCCTCAGTTGCTATCAA
 301 CATATCATGCTGTTTGGCTGTACCCTCGCCTTCCCTGAGTGCATCATTGATGGCGATGAC
 361 AGTCATGGACTCCTGCCCTGTAGGTCCTTCTGTGAGGCTGCAAAGAAGGCTGTGAATCA
 421 GTCCTGGGGATGGTGAATTACTCCTGGCCGGATTTCCTCAGATGCTCCCAGTTTAGAAAC
 481 CAAACTGAAAGCAGCAATGTCAGCAGAATTTGCTTCTCACCTCAGCAGGAAAACGGAAAG
 541 CAATTGCTCTGTGGAAGGGGTGAGAACTTTCTGTGTGCCAGTGGAATCTGCATCCCCGGG
 601 AAACTGCAATGTAATGGCTACAACGACTGTGACGACTGGAGTGACGAGGCTCATTGCAAC
 661 TGCAGCGAGAATCTGTTTCACTGTCACACAGGCAAGTGCCTTAATTACAGCCTTGTGTGT
 721 GATGGATATGATGACTGTGGGGATTTGAGTGATGAGCAAAACTGTGATTGCAATCCCACA
 781 ACAGAGCATCGCTGCGGGACGGGCGCTGCATCGCCATGGAGTGGGTGTGTGATGGTGAC
 841 CACGACTGTGTGGATAAGTCTGACGAGGTCAACTGCTCCTGTCACAGCCAGGGTCTGGTG
 901 GAATGCAGAAATGGACAATGTATCCCCAGCACGTTTCAATGTGATGGTGACGAGGACTGC
 961 AAGGATGGGAGTGATGAGGAGAACTGCAGCGTCATTCAGACTTCATGTCAAGAAGGAGAC
1021 CAAAGATGCCTCTACAATCCCTGCCTTGATTCATGTGGTGGTAGCTCTCTCTGTGACCCG
1081 AACAACAGTCTGAATAACTGTAGTCAATGTGAACCAATTACATTGGAACTCTGCATGAAT
1141 TTGCCCTACAACAGTACAAGTTATCCAAATTATTTTGGCCACAGGACTCAAAAGGAAGCA
1201 TCCATCAGCTGGGAGTCTTCTCTTTTCCCTGCACTTGTTCAAACCAACTGTTATAAATAC
1261 CTCATGTTCTTTTCTTGCACCATTTTGGTACCAAAATGTGATGTGAATACAGGCGAGCGT
1321 ATCCCTCCTTGCAGGGCATTGTGTGAACACTCTAAAGAACGCTGTGAGTCTGTTCTTGGG
1381 ATTGTGGGCCTACAGTGGCCTGAAGACACAGATTGCAGTCAATTTCCAGAGGAAAATTCA
1441 GACAATCAAACCTGCCTGATGCCTGATGAATATGTGGAAGAATGCTCACCTAGTCATTTC
1501 AAGTGCCGCTCAGGACAGTGTGTTCTGGCTTCCAGAAGATGTGATGGCCAGGCCGACTGT
1561 GACGATGACAGTGATGAGGAAAACTGTGGTTGTAAAGAGAGAGATCTTTGGGAATGTCCA
1621 TCCAATAAACAATGTTTGAAGCACACAGTGATCTGCGATGGGTTCCCAGACTGCCCTGAT
1681 TACATGGACGAGAAAAACTGCTCATTTTGCCAAGATGATGAGCTGGAATGTGCAAACCAT
1741 GCGTGTGTGTCACGTGACCTGTGGTGTGATGGTGAAGCCGACTGCTCAGACAGTTCAGAT
1801 GAATGGGACTGTGTGACCCTCTCTATAAATGTGAACTCCTCTTCCTTTCTGATGGTTCAC
1861 AGAGCTGCCACAGAACACCACGTGTGTGCAGATGGCTGGCAGGAGATATTGAGTCAGCTG
1921 GCCTGCAAGCAGATGGGTTTAGGAGAACCATCTGTGACCAAATTGATACAGGAACAGGAG
1981 AAAGAGCCGCGGTGGCTGACATTACACTCCAACTGGGAGAGCCTCAATGGGACCACTTTA
2041 CATGAACTTCTAGTAAATGGGCAGTCTTGTGAGAGCAGAAGTAAAATTTCTCTTCTGTGT
2101 ACTAAACAAGACTGTGGGCGCCGCCCTGCTGCCGACGATGACGATAAGATCCTTGGAGGT
2161 CGGACGAGTCGCCCTGGAAGGTGGCCATGGCAGTGTTCTCTGCAGAGTGAACCCAGTGGA
2221 CATATCTGTGGCTGTGTCCTCATTGCCAAGAAGTGGGTTCTGACAGTTGCCCACTGCTTC
2281 GAGGGGAGAGAGAATGCTGCAGTTTGGAAAGTGGTGCTTGGCATCAACAATCTAGACCAT
2341 CCATCAGTGTTCATGCAGACACGCTTTGTGAAGACCATCATCCTGCATCCCCGCTACAGT
2401 CGAGCAGTGGTGGACTATGACATCAGCATCGTTGAGCTGAGTGAAGACATCAGTGAGACT
2461 GGCTACGTCCGGCCTGTCTGCTTGCCCAACCCGGAGCAGTGGCTAGAGCCTGACACGTAC
2521 TGCTATATCACAGGCTGGGGCCACATGGGCAATAAAATGCCATTTAAGCTGCAAGAGGGA
2581 GAGGTCCGCATTATTTCTCTGGAACATTGTCAGTCCTACTTTGACATGAAGACCATCACC
2641 ACTCGGATGATATGTGCTGGCTATGAGTCTGGCACAGTTGATTCATGCATGGGTGACAGC
2701 GGTGGGCCTCTTGTTTGTGAGAAGCCTGGAGGACGGTGGACATTATTTGGATTAACTTCA
2761 TGGGGCTCCGTCTGCTTTTCCAAAGTCCTGGGGCCTGGCGTTTATAGTAATGTGTCATAT
2821 TTCGTCGAATGGATTAAAAGACAGATTTACATCCAGACCTTTCTCCTAAACAAGGGCGAG
2881 CTTGGTACCGAGCTCGGATCCGAAGGTAAGCCTATCCCTAACCCTCTCCTCGGTCTCGAT
2941 TCTACGCGTACCGGTCATCATCACCATCACCATTGA
```

MODIFIED CORIN MOLECULES HAVING SUBSTITUTE ACTIVATION SEQUENCES AND USES THEREOF

This is a non-provisional application claiming priority under 35 U.S.C. § 119 provisional application No. 60/477,683, filed Jun. 11, 2003.

FIELD OF THE INVENTION

The present invention relates to novel modified corin molecules, or fragments or derivatives thereof, comprising a substitute activation sequence.

BACKGROUND

Serine proteases are essential for a variety of biological processes, including food digestion, hormone processing, blood coagulation, complement activation, wound healing, and embryonic development (Davie, E. W. et al. (1991) *Biochemistry* 30:10463–10370; Kraut, J. (1977) *Annu. Rev. Biochem.* 46:331–358; Neurath, H. (1986) *J. Cell Biochem.* 32:35–49; and Stroud, R. M. (1974) *Sci. Am.* 231–74–88). Most trypsin-like serine proteases are secreted proteins, but several type II transmembrane proteins containing a trypsin-like protease domain at their extracellular C-terminus have been described (Hooper, J. D. et al. (2001) *J. Biol. Chem.* 276:857–860).

Corin is a member of the type II transmembrane serine protease class of the trypsin superfamily composed of multiple structurally distinct domains (Yan, W. et at. (1999)*J. Biol. Chem.* 274: 14926–14935). Mature corin is a polypeptide of 1042 amino acids (SEQ ID NO:2) consisting of a cytoplasmic tail at its N-terminus, followed by a transmembrane domain (TM, amino acids 46 to 66), a stem region composed of two frizzled-like cysteine-rich domains (CRD, amino acids 134 to 259 and 450 to 573), eight low density lipoprotein receptor repeats (LDLR, amino acids 268 to 415 and 579 to 690), a macrophage scavenger receptor-like domain (SRCR, amino acids 713 to 800, and a serine protease catalytic domain at its C-terminus (CAT, amino acids 802 to 1042) (Yan, W. et at. (1999) supra). The overall topology of corin is similar to that of other type II transmembrane serine proteases, such as hepsin (Leytus, S. P. et at. (1988) *Biochemistry* 27: 1067–1074) and enterokinase (Kitamoto, Y. et at. (1994) *Proc. Natl. Acad. Sci. USA* 91:7588–7592); however, the combination of domain structures in corin appears to be unique.

Corin contains two LDLR motifs, one with 5 repeats and the other with 3 repeats, and a SRCR motif. The LDLR and SRCR motifs are also found in other type II transmembrane serine proteases, for example, enterokinase, matriptase and TMPRSS2-4 (Hooper, J. D. et al. (2001) supra). Corin, the only trypsin-like serine protease to date that contains frizzled-like cysteine-rich domains, has two such CRD repeats, each about 120 amino acids in length containing 10 conserved cysteine residues. The functions of the CRD, LDLR, and SRCR motifs in corin remain to be defined.

The protease catalytic domain of corin is homologous to those of trypsin-like serine proteases. Amino acid sequence identities between corin and prokallikrein (Chung, D. W. et al. (1986) *Biochemistry* 25:2410–2417), factor XI (Fujikawa, K. et al. (1986) *Biochemistry* 25:2417–2424) and hepsin (Leytus, S. P. et al. (1988) supra) are 38–40%. The essential features of trypsin-like serine proteases are conserved, including the residues of the catalytic triad His843, Asp892, and Ser985 of SEQ ID NO:2, and the residues forming the substrate specificity pocket Asp979, Gly1007, and Gly1008 of SEQ ID NO:2 (Yan, W. et al. (1999) supra). The substrate specificity of corin is predicted to favor basic residues in the P1 position. The sequence Arg801-Ile802-Leu803-Gly804-Gly805 of SEQ ID NO:2, or RILGG (SEQ ID NO:42), represents a conserved activation cleavage site, indicating that proteolytic cleavage of the peptide bond between Arg801 and Ile802 is required to generate a catalytically active corin enzyme. The presence of residues Cys790 and Cys912 indicates that the catalytic domain of corin remains attached to the cell surface by a disulfide bond after the activation cleavage at Arg801. The enzyme responsible for the activation of corin under physiological conditions in vivo is not known.

Native corin appears as a major band of ~130 kDa in SDS-PAGE and Western blot analysis (Hooper, J. D. et al. (2001) supra), consistent with the calculated mass of 116 kDa for recombinant human corin containing 19 potential N-linked glycosylation sites in its extracellular domains (Yan, W. et al. (1999) supra).

Atrial natriuretic peptide (ANP) and brain-type natriuretic peptide (BNP) are circulating peptide hormones produced primarily by cardiomyocytes in the atrium and ventricle, respectively (Levin, E. R. et al. (1998) *N. Engl. J. Med.* 339:321–328; Wilkins, M. R. et al. (1997) *Lancet* 349: 1307–1310). In target organs such as kidney and peripheral vessels, these peptide hormones bind to their receptors and stimulate the intrinsic guanylate cyclase activity of the receptor, leading to production of intracellular cGMP. The biological effects of ANP and BNP are to promote salt excretion, reduce blood volume, and decrease vascular resistance, thereby reducing blood pressure (de Bold, A. J. et al. (1981) *Life Sci.* 28:89–94; Inagami, T. (1989) J. Biol. Chem. 264:3043–3046; Brenner, B. M. et al. (1990) *Physiol. Rev.* 70:665–699; Rosenzweig, A. and Seidman, C. E. (1991) *Annu. Rev. Biochem.* 60:229–255; Wilkins, M. R. et al. (1997) supra; Stein, B. C. and Levin, R. I. (1998) *Am. Heart J.* 135:914–923; Liang, F. et al. (1997) *J. Biol. Chem.* 272:28050–28056). BNP also has a local antifibrotic effect in the heart (Tamura, N. et al. (2000) *Proc. Natl. Acad. Sci. USA* 97:4239–4244). The biological importance of the ANP-mediated pathway in maintaining normal blood pressure has been demonstrated in a number of studies. In knockout mice, for example, deficiency of either ANP or its receptor leads to spontaneous hypertension (John, S. W. et al. (1995) *Science* 267:679–681; John, S. W. et al. (1996) *Am. J. Physiol.* 271:R109-R114; Lopez, M. J. et al. (1995) *Nature* 378:65–68).

ANP and BNP are synthesized as pre-pro-peptides in cardiomyocytes, and proteolytic cleavage is required to convert the precursors to biologically active peptide hormones (Shields, P. P. and Glembotski, C. C. (1988) *J. Biol. Chem.* 263:8091–8098; Ito, T. et al. (1988) *Proc. Natl. Acad. Sci. USA* 85:8365–8369). In response to volume overload or a hypertrophic signal, the heart increases its release of these hormones, which in turn reduce blood volume and lower blood pressure. The increased release of ANP and BNP has been attributed to the increased synthesis of pro-ANP and pro-BNP (McBride, K. and Nemer, M. (2001) *Can. J. Physiol. Pharmacol.* 79:673–681).

In cardiac myocytes, ANP is synthesized as a 126 amino acid pre-pro-peptide (Schwartz, D. et al. (1985) Science 229:397–400; Thibault, G. et al. (1987) *Biochem. J.* 241: 265–272). After the signal peptide is removed, pro-ANP is stored in the dense granules of the cell. Upon secretion from the dense granules, pro-ANP is activated on the surface of cardiac myocytes by proteolytic cleavage at Arg98, generating an N-terminal pro-peptide and a biologically active, mature 26 amino acid C-terminal peptide (Shields, P. P. and Glembotski, C. C. (1988) supra; Ito, T. et al. (1988) supra). BNP is also synthesized as a pre-pro-peptide and cleavage is required to produce the mature, active peptide. The activation cleavage sequence in pro-BNP is similar to that of pro-ANP, with proteolytic cleavage occurring at Arg76. Several studies indicate that a high-molecular-weight trypsin-like enzyme associated with the membrane of cardiac myocytes is responsible for the activation cleavage of pro-ANP (Seidah, N. G. et al. (1986) *Biosci. Rep.* 6:835–844; Imada, T. et al. (1988) *J. Biol. Chem.* 263: 9515–9519; Sei, C. A. et al. (1992) *Mol. Endocrinol.* 6:309–319).

Corin cDNA was first identified by searching genomic databases for expressed sequence tags (ESTs) that share homology with trypsin-like proteases, and was subsequently cloned from a human heart library (Yan, W. et al. (1999) supra). Northern blot and in situ hybridization analyses show that corin mRNA is highly expressed in tissues where ANP and BNP peptides are produced, predominantly in the atrium and ventricle of the heart (Yan, W. et al. (1999) supra). In functional studies (Yan, W. et al. (2000) *Proc. Natl. Acad. Sci. USA* 97:8525–8529; Wu, F. et al. (2002) *J. Biol. Chem.* 277:16900–16905), recombinant corin converts pro-ANP into biologically active ANP in a highly sequence-specific manner, indicating that corin is the pro-ANP convertase. In addition, recombinant corin processes pro-BNP to BNP (Yan, W. et al. (2000) supra).

Congestive heart failure (CHF) is a life-threatening disease, afflicting approximately 4.8 million Americans. Each year, approximately 550,000 new cases are diagnosed in the United States. Symptomatic decompensation is the most common reason for the hospitalization of patients with CHF due to left ventricular systolic dysfunction. Most common symptoms include dyspnea and fatigue resulting mainly from pulmonary venous congestion and reduced cardiac output. Traditionally, patients with decompensated CHF are treated with diuretics, inotropic agents, vasodilators and β blockers (Braunwald, E. et al. (1997) in *Heart Disease: A Textbook of Cardiovascular Medicine*, Braunwald, E., ed., W. B. Saunders, Philadelphia, pp.445–470). The therapeutic goal is to increase sodium and fluid excretion, decrease cardiac filling pressures, reduce peripheral vascular resistance, and increase cardiac output. The various drugs used to treat CHF usually alleviate symptoms, although each therapy has inherent limitations. For example, inotropic drugs increase cardiac contractility and oxygen consumption of the failing heart, but also increase the incidence of cardiac arrhythmias and may increase mortality. Repeated and prolonged use of nitroglycerin, a vasodilator originally manufactured by Alfred Nobel to produce dynamite over 130 years ago, results in nitrate tolerance with the loss of clinical efficacy over time, leaving patients vulnerable to new ischemic attacks.

Despite advances in the understanding of the pathophysiology of CHF, effective treatments for advanced disease are limited and the morbidity and mortality remains high. Current approaches to chronic treatment of CHF target the renin-angiotension system (angiotensin-converting enzyme (ACE) inhibitors, angiotensin receptor blockers), the sympathetic nervous system (β-blockers), endothelin-1 (ET-1) (ET-1 receptor antagonists) and the natriuretic peptide system (ANP, BNP, and neutral endopeptidase (NEP) inhibitors) (McMurray, J. and Pfeffer, M. A. (2000a) *Circulation* 105:2099–2106; McMurray, J. and Pfeffer, M. A. (2000b) *Circulation* 105:2223–2228; Corti, R. et al. (2001) *Circulation* 104:1856–1862). Clinically, high plasma concentrations of ANP and BNP are found in patients with CHF. The levels of these natriuretic peptides are often correlated with the extent of ventricular dysfunction and development of cardiac arrhythmias (Burnett, J. C., Jr. et al. (1986) *Science* 231:1145–1147; Gottleib, S. S. et al. (1989) *J. Am. Coll. Cardiol.* 13:1534–1539). BNP is currently used as a diagnostic and prognostic marker in CHF (Gottleib, S. S. et al. (1989) supra; Maisel, A. S. et al. (2002) *N. Engl. J. Med.* 347:161–167). Natrecor, a recombinant form of human BNP, has been approved in the U.S. as a short-term, in hospital treatment for decompensated CHF. Infusion of BNP has been shown to be more effective than nitroglycerin in improving hemodynamics and cardiac and renal function in patients with CHF (Colucci, W. S. et al. (2001) supra). ANP has also been used in Japan to treat patients with CHF and renal failure (Hayashi, M. et al. (2001) supra; Mizuno, O. et al. (2001) *J. Am. Cardiol.* 88:863–866; Allgren, R. L. et al. (1997) *N. Engl. J. Med.* 336:828–834). The results with ANP and BNP demonstrate that natriuretic peptide-based therapies are effective in relieving symptoms and improving hemodynamics and cardiac function in patients with severe CHF.

The discovery of corin provides an opportunity to use recombinant corin as a biological agent to increase the production of both ANP and BNP in vivo. Corin-based therapy may be more effective than either ANP or BNP alone in the treatment of decompensated CHF. In addition, corin may offer pharmacokinetic advantages over ANP or BNP, which must be administered by continuous, intravenous infusion. The instant invention is a novel soluble form of corin as a biological therapy for decompensated CHF.

SUMMARY OF THE INVENTION

The present invention provides novel modified corin molecules, or fragments or derivatives thereof, comprising a substituted activation sequence differing from the wild-type human corin activation sequence, and methods to encode, express, and use stable modified corin molecules.

In one embodiment, the modified corin molecule is a modified corin zymogen, or fragments or derivatives thereof, comprising a substituted activation sequence differing from the wild-type human corin activation sequence.

In another embodiment, the modified corin molecule is an activated modified corin, or fragments or derivatives thereof, wherein a substituted activation sequence, differing from the wild-type human corin activation sequence is cleaved, rendering the corin active.

The present invention provides fusion molecules comprising a modified corin molecule, or fragments or derivatives thereof, fused to a non-corin molecule. In one embodiment, the non-corin molecule is an epitope tag or a reporter molecule. The invention further provides methods to encode, express, and use modified corin fusion molecules.

The present invention provides chimeric molecules comprising a portion of a corin molecule, isolated from a first source, fused to a portion of a corin molecule, isolated from a second, different source. The invention further provides methods to encode, express, and use chimeric corin molecules.

The present invention provides a host vector system comprising a vector comprising a nucleotide sequence encoding a modified corin molecule, or a fragment or derivative thereof, introduced into a suitable host cell. The invention further provides methods to make and use the host vector system.

The present invention provides a pharmaceutical composition comprising a pharmaceutically acceptable carrier and a composition of the invention. In one embodiment, the pharmaceutical composition comprises a pharmaceutically acceptable carrier admixed with a modified corin molecule of the invention.

The present invention provides in vitro and in vivo assays to characterize the compositions of the invention.

Kits comprising compositions are also encompassed by the invention. In one embodiment, a kit comprising one or more of the compositions of the invention is used in a screening assay to identify corin ligands or inhibitors. In another embodiment, a kit comprising one or more of the compositions of the invention is used in a screening assay to identify activated corin molecules.

Methods for using the compositions of the invention are provided. The compositions can be used to treat diseases associated with over-, under- and/or aberrant-expression of corin. In one embodiment, the compositions can be used to treat cardiovascular diseases associated with elevated blood pressure.

BRIEF DESCRIPTION OF THE FIGURES

FIG. 1. Nucleic acid sequence of the human corin coding region (SEQ ID NO:1). The coding sequence is 3129 nucleotides in length starting from the methionine initiation codon ATG at position 1–3 and ending at the translation termination codon TAA at position 3127–3129.

FIG. 2. Amino acid sequence of the human corin polypeptide (SEQ ID NO:2). Full-length human corin is 1042 amino acids in length consisting of an N-terminal cytoplasmic tail, followed by a transmembrane domain (amino acids 46 to 66), two frizzled-like cysteine-rich domains (amino acids 134 to 259 and 450 to 573), eight low density lipoprotein receptor repeats (amino acids 268 to 415 and 579 to 690), a macrophage scavenger receptor-like domain (amino acids 713 to 800, and a serine protease catalytic domain at its C-terminus (amino acids 802 to 1042). A schematic structure of the full-length corin polypeptide is depicted in FIG. 3.

FIG. 9. Cleavage of pro-ANP by enterokinase-activated soluble modified human corin. SolCorin-EK or SolCorinPD-EK expression vectors were transfected into human 293 cells as indicated. The conditioned medium was treated with the indicated amounts of recombinant enterokinase, and the enterokinase-depleted conditioned medium was exposed to conditioned medium from 293 cells transfected with a pro-ANP expression vector. Corin, enterokinase-activated corin, pro-ANP and ANP were detected by Western blotting using an anti-V5 antibody.

FIG. 10. Nucleic acid sequence of soluble modified human corin polypeptide SolCorin-EK. The nucleic acid sequence of SolCorin-EK (SEQ ID NO:33) consists of the N-terminal ATG initiation codon and Igκ secretion signal sequence (position 1 to 108), Leu-Glu (position 109 to 114), human corin amino acids 124 to 796 (position 115 to 2133), the enterokinase activation cleavage sequence (position 2134 to 2148), human corin amino acids 802 to 1042 (position 2149 to 2871), the C-terminal viral V5 and 6xHis epitope tags (position 2871 to 2973), and a TGA termination codon (position 2974 to 2976).

FIG. 11. Amino acid sequence of soluble modified human corin polypeptide SolCorin-EK. The amino acid sequence of SolCorin-EK (SEQ ID NO:34) consists of the N-terminal ATG initiation codon and Igκ secretion signal sequence (amino acids 1 to 36), Leu-Glu (amino acids 37 to 38), human corin amino acids 124 to 796 (amino acids 39 to 711), the enterokinase activation cleavage sequence (underlined, amino acids 712 to 716), human corin amino acids 802 to 1042 (amino acids 717 to 957), the C-terminal viral V5 and 6xHis epitope tags (amino acids 958 to 991), and a TGA termination codon.

DETAILED DESCRIPTION OF THE INVENTION

A. Definitions

Figure 3:
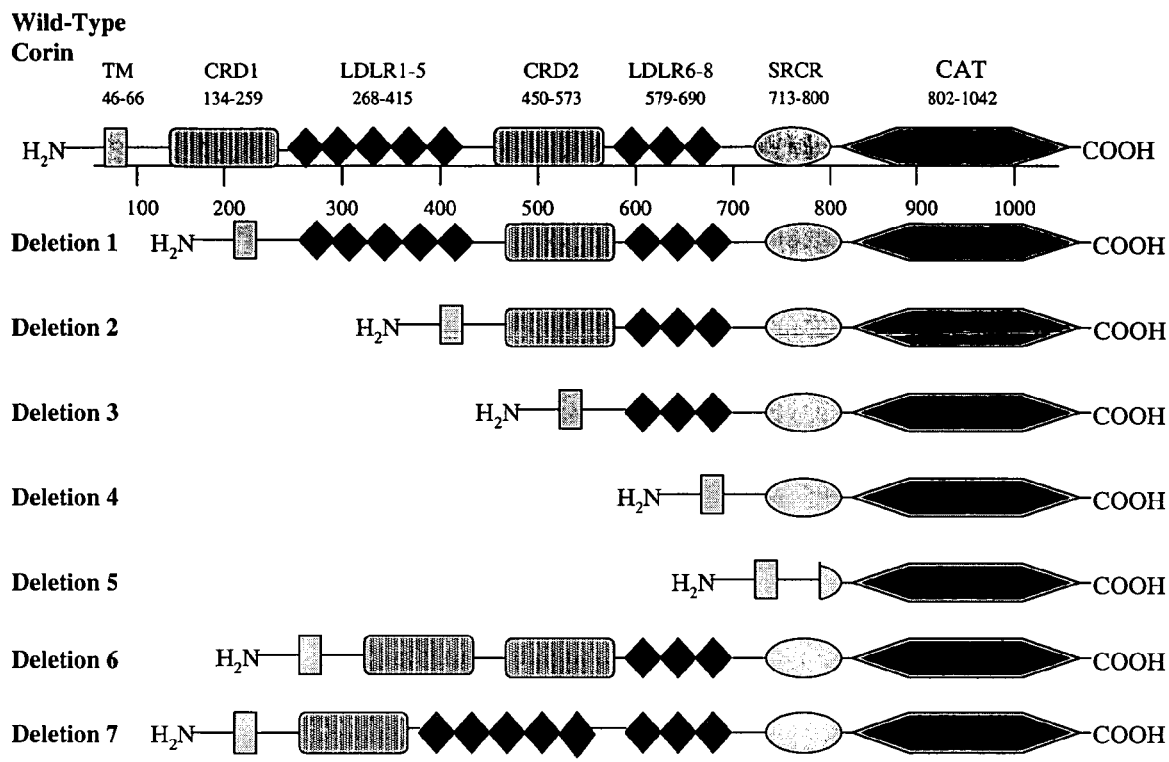
FIG. 3. Schematic structures of transmembrane human corin deletion mutants. The construction of human corin internal deletion mutants is described in Example 1. Deletion 1 lacks amino acids 124 to 267, Deletion 2 lacks amino acids 124 to 448, Deletion 3 lacks amino acids 124 to 576, Deletion 4 lacks amino acids 124 to 712, Deletion 5 lacks amino acids 124 to 788, Deletion 6 lacks amino acids 269 to 414, and Deletion 7 lacks amino acids 450 to 568.

All scientific and technical terms used in this application have meanings commonly used in the art unless otherwise specified. As used in this application, the following words or phrases have the meanings specified.

As used herein, "corin" refers to a transmembrane polypeptide molecule having a cytoplasmic, transmembrane and extracellular domain (also referred to herein as the ectodomain) with an activation site, or fragments or derivatives thereof. The term "corin" includes: wild-type corin including corin zymogens, activated corin molecules and fragments or derivatives thereof; and modified corin molecules, including modified corin zymogens, modified activated corin molecules, and fragments or derivatives thereof.

As used herein, "wild-type" refers to a nucleic acid or polypeptide molecule having the same nucleotide and/or amino acid sequence as a naturally occurring molecule, respectively. A wild-type corin polypeptide molecule has the amino acid sequence of naturally occurring corin as shown in FIG. 1 and in Yan, W. et al. (1999) supra, or any fragment or portion thereof. Wild-type corin is synthesized as a zymogen, i.e., an enzyme precursor, which is activated upon cleavage of an activation site in its extracellular domain.

As used herein, the term "activity" refers to a molecule having a function or action. Activity includes enzymatic activity, wherein the molecule is an enzyme, e.g., a protease that recognizes, binds, cleaves, and/or modifies a substrate.

As used herein, the term "zymogen" refers to a precursor polypeptide molecule having an activation sequence that, upon cleavage by a cognate protease, yields an activated molecule. An example of a zymogen is a modified corin zymogen comprising an enterokinase substitute activation sequence, which becomes activated upon cleavage by enterokinase.

As used herein, the term "activation sequence" refers to an amino acid sequence in a molecule which is cleaved by a cognate protease, and which, when cleaved, renders the molecule biologically active, e.g., capable of protease activity. In an activated molecule, the activation sequence is cleaved. An example of an activation sequence in the corin molecule is R-ILGG (SEQ ID NO:42).

As used herein, the term "substitute activation sequence" refers to an amino acid sequence that replaces an activation sequence found in a wild-type molecule. An example of a substitute activation sequence is DDDDK-ILGG (SEQ ID NO:43), which is substituted for the naturally occurring activation sequence, R-ILGG (SEQ ID NO:42), in corin.

As used herein, the term "modified" refers to molecule with an amino acid or nucleotide sequence differing from a naturally occurring, i.e., wild-type amino acid or nucleotide sequence. For example, a modified corin molecule can include a substitute activation sequence. A modified molecule can retain the function or activity of a wild-type molecule.

As used herein, the term "derivative" means any modification or alteration of a wild-type molecule. Derivatives include, but are not limited to: a substitution, conservative or non-conservative, in a amino acid and/or nucleotide sequence including substitutions by other amino acids, nucleotides, amino acid analogs or nucleotide analogs; a deletion of one or more amino acids and/or nucleotides; an insertion of one or more amino acids and/or nucleotides; and pre- and/or post-translational modifications. A derivative molecule can share sequence similarity and/or activity with its parent molecule.

As used herein, the term "protease" refers to a class of enzymes which recognizes a molecule and cleaves an activation sequence in the molecule. The protease can be an endopeptidase, which cleaves internal peptide bonds. Alternatively, the protease can be an exopeptidase, which hydrolyzes the peptide bonds from the N-terminal end or the C-terminal end of the polypeptide or protein molecule. The protease folds into a conformation to form a catalytic site, which receives and cleaves the activation sequence.

As used herein, the term "catalytic site" refers to a region in a folded protease that receives and cleaves the activation sequence.

As used herein, the term "ligand" refers to any molecule that interacts with corin. A ligand can be a molecule that recognizes and binds to corin. Alternatively, a ligand can be a molecule recognized and bound by corin. For example, a substrate that corin binds to and cleaves can be a ligand. In another example, a molecule that binds to and cleaves corin can be a ligand. An anti-corin antibody can also be a ligand.

As used herein, the term "serine protease" refers to a class of protease enzymes characterized by the presence of a unique serine residue that forms part of the catalytic site in the enzyme. In general, each serine protease member has a different substrate specificity.

As used herein, a first nucleotide or amino acid sequence is said to have sequence "identity" to a second nucleotide or amino acid sequence, respectively, when a comparison of the first and the second sequences shows that they are exactly alike.

As used herein, a first nucleotide or amino acid sequence is said to be "similar" to a second sequence when a comparison of the two sequences shows that they have few sequence differences (i.e., the first and second sequences are nearly identical). For example, two sequences are considered to be similar to each other when the percentage of nucleotides or amino acids that differ between the two sequences can be between about 60% to 99.99%.

As used herein, the term "complementary" refers to nucleic acid molecules having purine and pyrimidine nucleotide bases which have the capacity to associate through hydrogen bonding to form base pairs thereby mediating formation of double stranded nucleic acid molecules. The following base pairs are related by complementarity: guanine and cytosine; adenine and thymine; and adenine and uracil. Complementary applies to all base pairs comprising two single-stranded nucleic acid molecules, or to all base pairs comprising a single-stranded nucleic acid molecule folded upon itself.

As used herein, the term "conservative" refers to substituting an amino acid residue for a different amino acid residue that has similar chemical properties. A conservative amino acid substitution includes: substituting any hydrophobic (e.g., nonpolar) amino acid for any other hydrophobic amino acid; or substituting any hydrophilic (polar, uncharged) amino acid for any other hydrophilic amino acid; or substituting any positively charged amino acid for any other positively charge amino acid; or substituting any negatively charge amino acid for any other negatively charged amino acid (Creighton, T. E. (1993) Proteins, W. H. Freeman and Company, New York). The amino acid substitutions include, but are not limited to, substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A), or glycine (G) and serine (S) can frequently be interchangeable, as can alanine (A) and valine (V). Methionine (M), which is relatively hydrophobic, can frequently be interchanged with leucine and isoleucine, and sometimes with valine (V). Lysine (K) and arginine (R) are frequently interchangeable in locations in which the significant feature of the amino acid residue is its charge and the differing pK's of these two amino acid residues are not significant. Still other changes can be considered conservative in particular environments.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

As used herein, the term "soluble" refers to any molecule, or fragments and derivatives thereof, not bound or attached to a cell. A soluble molecule can be circulating. A soluble molecule typically lacks a transmembrane domain. A soluble molecule typically includes an extracellular domain.

The single- and triple-letter codes for amino acid residues include the following: A=Ala=alanine, R=Arg=arginine, N=Asn=asparagine, D=Asp=aspartic acid, C=Cys=cysteine, Q=Gln=glutamine, E=Glu=glutamic acid, G=Gly=glycine, H=His=histidine, I=Ile=isoleucine, L=Leu=leucine, K=Lys=lysine, M=Met=methionine, F=Phe=phenylalanine, P=Pro=proline, S=Ser=serine, T=Thr=threonine, W=Trp=tryptophan, Y=Tyr=tyrosine, and V=Val=valine.

As used herein, the term "mammal" includes humans and domesticated animals, such as cats, dogs, swine, cattle, sheep, goats, horses, rabbits, and the like.

As used herein, the term "therapeutically effective amount" refers to that amount of a protein of the invention which, when administered to a human in need thereof, is sufficient to effect treatment, as defined below, for example, for congestive heart failure or acute myocardial infarction. The amount of a modified corin molecule of the invention which constitutes a "therapeutically effective amount" will vary depending on the protein, the condition and its severity, and the age of the human to be treated, but can be determined routinely by one of ordinary skill in the art having regard to his own knowledge and to this disclosure.

As used herein, the term "treating" or "treatment" covers the treatment of disease-state in a mammal, preferably a human, which disease-state is characterized by elevated blood pressure, and includes:

(i) preventing the condition from occurring in a human, in particular, when such human is predisposed to the condition but has not yet been diagnosed as having it;

(ii) inhibiting the condition, i.e., arresting its development; or (iii) relieving the condition, i.e., causing regression of the condition.

B. Modified Corin Polypeptide Molecules of the Invention

The modified corin molecules of the present invention include modified corin zymogens and activated modified corin molecules, or fragments or derivatives thereof. These modified corin molecules are useful because they comprise a substituted activation sequence that, when cleaved, activates the modified corin molecule. The modified corin molecules of the invention are stable.

In its various aspects, the present invention provides: modified corin molecules, including modified corin zymogens, activated modified corins, or fragments or derivatives thereof; nucleic acid molecules encoding the modified corin molecules, or fragments or derivatives thereof; recombinant DNA molecules; transformed host cells; host-vector systems; methods for using the compositions of the invention; methods for generating the compositions of the invention; assays; inhibitors of modified corin; and nucleic acid-based assays.

Modified Corin Molecules

Activation of a corin molecule can proceed by cleavage of the peptide bond between Arg801 and Ile802 in a naturally occurring activation sequence, Arg801-Ile802-Leu803-Gly804-Gly805 or R-ILGG, to generate a catalytically active enzyme, i.e., an active corin.

The modified corin molecules of the invention, including modified corin zymogens, activated modified corin, or fragments or derivatives thereof, comprise a substitute activation sequence.

The substitute activation sequence provides a known activation sequence in the modified corin molecule, which will permit cleavage of the modified corin molecule by a protease, e.g., a cognate protease, producing an modified activated corin molecule. In one embodiment, the modified corin molecule comprises a substitute activation sequence specifically recognized by enterokinase comprising an amino acid sequence, Asp-Asp-Asp-Asp-Lys or DDDDK (SEQ ID NO:44), replacing amino acid Arg801. Contacting a modified corin molecule in its zymogen form with an enterokinase, e.g. a recombinant enterokinase, cleaves the substitute activation sequence and produces a modified corin molecule in its activated form.

Examples of substitute activation sequences are described, infra. The sequence and length of the substitute activation sequence are selected to permit the modified corin zymogen to be cleaved by a desired cognate protease, thereby generating an activated modified corin.

The activated modified corin molecules of the invention exhibit the functional activity of a naturally occurring, wild-type activated corin. The functional activity of a naturally occurring, wild-type activated corin is recognizing and cleaving the sequence, Arg-Ser, on a protein substrate, such as pro-ANP or pro-BNP to produce biologically active ANP or BNP (Yan, W. et al. (2000) supra). In a similar manner, the activated modified corin can function as a protease and can recognize and cleave the same substrate as wild-type activated corin.

In accordance with the practice of the invention, modified corin molecules of the invention can have a folded structure which is the same, or similar to, that of naturally occurring, wild-type corin molecules. For example, an activated modified corin can be folded into a conformation that permits the catalytic site to receive and cleave a substrate recognized by wild-type activated corin.

A full-length, naturally occurring, human corin molecule (FIG. 1) (Yan, W. et al. (1999) supra, and published PCT patent application WO99/64608) includes the following: 1) a cytoplasmic domain encompassing amino acid residues 1 to 45; 2) a transmembrane domain encompassing amino acid residues 46 to 66; and 3) an extracellular domain encompassing amino acid residues 67 to 1042 and comprising two frizzled-like cysteine-rich domains, eight low density lipoprotein receptor repeats, a macrophage scavenger receptor-like domain, an activation sequence, and a serine protease catalytic domain.

The present invention provides modified corin molecules, comprising fragments or derivatives of the naturally occurring corin molecules. Fragments or derivatives of the modified corin molecules can include any portion of the domains, described above, associated and/or linked in any combination or order.

In one embodiment, a modified corin molecule comprises the extracellular domain of a naturally occurring human corin molecule, encompassing amino acid residues 67 to 1042, or portion thereof, of the sequence shown in FIG. 1. In another embodiment, a modified corin molecule comprises the extracellular domain, or portion thereof, of a naturally occurring corin molecule modified to include an enterokinase, or other protease recognition sequence, e.g., an enterokinase recognition sequence. Such embodiments are typically soluble molecules because they lack a transmembrane domain.

The present invention provides modified corin molecules, or fragments or derivatives thereof, derived or isolated from any source whether natural, synthetic, semi-synthetic, or recombinant.

Sources include prokaryotes or eukaryotes. Eukaryotic sources include animal, plants, fungi or protista. Animal sources include mammalian such bovine, porcine, murine (PCT patent application WO99/64608), equine, canine, feline, simian, human (Yan, W. et al. (1999) supra), ovine, piscine, avian or insects.

The modified corin molecules of the invention, or fragments or derivatives thereof, can be expressed as recombinant molecules produced in prokaryote or eukaryote host cells, or generated as synthetic molecules. In one embodiment, a recombinant modified corin molecule can be isolated from bacterial host cells, which produce inclusion bodies including the modified corin molecule. Alternative methods to isolate corin molecules can also be used. In another embodiment, modified corin molecules can be isolated from baculovirus infected insect cells.

Purification of Modified Corin Molecules

Modified corin molecules of the invention, or fragments or derivatives thereof, can be purified by methods well known in the art. These purification methods include: affinity chromatography using antibodies that selectively bind the modified corin molecules; affinity chromatography using antibodies that selectively bind an epitope tag linked to the modified corin molecules, such as 6×His tags, V5 tags or other well known tags (Marchak, D. R. et al. (1996) in *Strategies for Protein Purification and Characterization*, Cold Spring Harbor Press, Plainview, N.Y.); ion exchange chromatography; and gel filtration chromatography. The nature and degree of isolation and purification will depend on the intended use. For example, purified, modified corin molecules will be substantially free of other proteins or molecules that impair the binding of ligands or antibodies to the modified corin molecules.

Fusion Molecules

The present invention provides fusion molecules, or fragments or derivatives thereof, comprising a modified corin molecule fused to a non-corin molecule encoding sequence.

The fusion molecules of the invention include a modified corin molecule fused to an epitope tag, such as histidine (6×His) tags, or V5 tags, FLAG tags, influenza hemagglutinin (HA) tags, Myc tags, VSV-G tags, or thioredoxin (Trx) tags. The tagged-fusion molecules are useful for fasciitating isolation and/or purification the modified corin molecule (Marchak, D. R. et al. (1996) supra).

The fusion molecules of the invention include a modified corin molecule fused to a reporter molecule. The reporter molecule can be a full-length protein, or a fragment or derivative thereof. Reporter molecules commonly used include glutathione-S-transferase (GST), horseradish peroxidase (HRP), chloramphenicol acetyltransferase (CAT) beta-galactosidase, beta-glucuronidase, luciferase, green fluorescent protein (GFP), and auto-fluorescent proteins including blue fluorescent protein (BFP).

Other fusion molecule constructions can include maltose binding protein (MBP), S-tag, Lex A DNA binding domain (DBD) fusions, GAL4 DNA binding domain fusions, and herpes simplex virus (HSV) BP16 protein fusions.

A fusion molecule also can be engineered to include a cleavage site located between the modified corin molecule and the non-corin molecule, so that the modified corin molecule can be cleaved and purified away from the non-corin molecule. The cleavage site can include recognition sequences for the following enzymes: enterokinase, hepsin, MT-SP/matryptase, trypsin, chymotrypsin, human airway trypsin-like protease (HAT), mast cell tryptase, elastase, plasmin, kallikrein, TMPRSS2, MBL-associated serine proteases (MASP-1 and MASP-2), Stubble-stubbloid, furin, thrombin, or factor Xa.

Chimeric Polypeptides

The present invention provides chimeric molecules, or fragments or derivatives thereof, which include a fragment of a corin molecule isolated from a first source fused to a fragment of a corin molecule isolated from a second, different source. The first and second source can be from any source including mammalian such as bovine, porcine, murine, equine, canine, feline, monkey, ape, ovine or human, or other sources such as piscine, avian or insect.

One or more of the corin fragments used to form a chimeric modified corin molecule can be modified, e.g., to include an enterokinase activation sequence. In one embodiment, a chimeric, modified corin molecule comprises the extracellular domain of a corin molecule from a first source, fused to the cytoplasmic domain of a corin molecule from a second source, where the extracellular domain includes a substitute activation sequence. In another embodiment, a chimeric, modified corin molecule comprises a fragment of the extracellular domain of a corin molecule from a first source, fused to another fragment of the extracellular domain of a corin molecule from a second source, where the chimeric corin molecule thus formed includes a substitute activation sequence.

Amino Acid Analogs and Altered Polypeptides

The present invention further provides modified corin molecules, or fragments or derivatives thereof, comprising amino acid analogs. The amino acid analogs can be chemically synthesized, and include dextro or levo forms, or peptidomimetics.

The present invention also provides modified corin molecules that are altered, for example, by post-translational pathways or by chemical synthesis, including N- or O-glycosylated amino acid residues. The N-terminal end of the polypeptides can be altered to include acylated or alkylated residues. The C-terminal end of the polypeptides can be altered to include esterified or amidated residues. The non-terminal amino acid residues can be altered, including but not limited to, alterations of the amino acids, arginine, aspartic acid, asparagine, proline, glutamic acid, lysine, serine, threonine, tyrosine, histidine, and cysteine.

Sequence Variants

The present invention provides modified corin molecules, or fragments or derivatives thereof, comprising sequence variations in the extracellular domain of a naturally occurring corin molecule. As persons skilled in the art understand, any number of amino acids can be varied alone, or in combination with other amino acids and yet the modified corin molecules will retain their functional activity (e.g., to be cleaved by a cognate protease and/or to cleave its substrates). Sequence variants of the extracellular domain of the modified corin molecules include: amino acid substitutions, amino acid insertions, amino acid deletions, mutant forms, allelic forms, homologs, and orthologs.

Amino Acid Substitutions

The modified corin molecules, or fragments or derivatives thereof, can include amino acid substitutions. The extracellular domain of a modified corin molecule can have conservative or non-conservative amino acid substitutions. Guidance in determining which and how many amino acid residues can be substituted in the extracellular domain of the modified corin molecule can be found in the properties of a naturally occurring, corin molecule. These properties include the amino acid length and the physical length, in the denatured or the folded conformation. These properties can be derived by prediction (e.g., based on amino acid sequence) and/or experiment (e.g., based on X-ray crystallography). The substituted amino acids are selected so that the properties of the variant, modified corin molecule are identical or similar to those of a naturally occurring corin molecule.

Mutant Forms

The present invention also provides modified corin molecules, or fragments or derivatives thereof, having a mutant form of an extracellular domain of a corin molecule. The mutant variant has an amino sequence that differs from that of the extracellular domain of a wild-type corin molecule. The mutation includes amino acid substitutions, deletions, insertions, additions, truncations, or processing or cleavage errors of the protein. The mutant variant can have the same or similar functional activity of a wild-type corin molecule.

Allelic Variants

The present invention provides modified corin molecules, or fragments or derivatives thereof, comprising allelic variants of a naturally occurring corin molecule. Allelic variants are molecules encoded by different genes residing at the same chromosomal locus.

Homologs

The present invention provides modified corin molecules, or fragments or derivatives thereof, comprising homologs of a naturally occurring corin molecule. Homologs are molecules encoded by nucleotide sequences from the same loci but on different chromosomes. The homologs can have the same or similar functional activity.

Orthologs

The present invention provides modified corin molecules, or fragments or derivatives thereof, comprising orthologs of a naturally occurring corin molecule. An ortholog is a corin molecule encoded by a nucleotide sequence from a different species. The ortholog can have the same or similar functional activity of a wild-type corin molecule.

The Substitute Activation Sequence

The present invention provides modified corin molecules, or fragments or derivatives thereof, each including a substitute activation sequence that replaces the naturally occurring activation sequence. The substitute activation sequence differs from the naturally occurring activation sequence of a corin molecule. For example, the naturally occurring activation sequence of a human, corin molecule comprises the amino acid sequence R-ILGG (Yan, W. et al. (1999) supra; Yan, W. et al. (2000) supra). The substitute activation sequence is recognized and cleaved by a cognate protease.

The substitute activation sequence can be an amino acid sequence recognized and cleaved by a protease from any species, particularly mammalian sources, including bovine, porcine, murine, equine, canine, feline, simian, ovine or human, or other sources such as piscine, avian or insect.

The substitute activation sequence can be an amino acid sequence recognized and cleaved by a protease, including any serine protease, any member of the trypsin family, any trypsin-like protease, and any type II transmembrane protease.

The activation sequence can be an amino acid sequence recognized and cleaved by the following enzymes (Barrett, A. J. et al. (eds) (1998) *Handbook of Proteolytic Enzymes*, Academic Press, London): enterokinase; thrombin; clotting factor Xa; furin; trypsin; chymotrypsin; elastase; plasmin; kallikrein; aerosin; human airway trypsin-like protease (HAT) (Yamaoka, K. et al. (1998) *J. Biol. Chem.* 273: 11895–11901); mast cell tryptase; MBL-associated serine proteases (MASP-1 and MASP-2) (Matsushita, M. et al. (2000) *J. Immunol.* 164:2281–2284); hepsin (Torres-Rosado, A. et al. (1993) *Proc. Natl. Acad. Sci. USA* 90:7181–7185); MT-SP1/matryptase (Takeuchi, T. et al. (1999) *Proc. Natl. Acad. Sci. USA* 96:11054–11061; Lin, C. Y. et al. (1999) *J. Biol. Chem.* 274:18231–18236); TMPRSS2 (Paoloni-Giacobina, A. et al. (1997) *Genomics* 44:309–320); or Stubble-stubbloid (Appel, L. F. et al. (1993) *Proc. Natl. Acad. Sci. USA* 90:4937–4941).

In one embodiment, the substitute activation sequence can be an amino acid sequence recognized and cleaved by a TMPRSS3 protease or an epitheliasin protease, such as the sequence LKTPR-VVGG (SEQ ID NO:38) (Paoloni-Giacobino, A. et al. (1997) supra; Lin, B. et al. (1999) *Cancer Res.* 59:4180–4184); or recognized and cleaved by an MT-SP1 protease or an epithin protease, such as the sequence TRQAR-VVGG (SEQ ID NO:39) (Kim, M. et al. (1999) *Immunogenetics* 49:420–428).

In another embodiment, the substitute activation sequence can be an amino acid sequence recognized and cleaved by an enterokinase protease, such as the sequence DDDDK-IVGG (SEQ ID NO:40) (Kitamoto, Y. et al. (1994) *Proc. Natl. Acad. Sci. USA* 91:7588–7592; La Vallie, E. R. et al. (1993) *J. Biol. Chem.* 268:23311–23317). In another embodiment, the substitute activation sequence is recognized and cleaved by human or bovine enterokinase, comprising the amino acid sequence DDDDK-I (SEQ ID NO:41).

Variant Substitute Activation Sequences

The present invention also provides modified corin molecules, or fragments or derivative thereof, comprising substitute activation sequences having sequence variations of the substitute activation sequences described above. The substitute activation sequence can have conservative amino acid substitutions, where a substituted amino acid has similar structural or chemical properties. Variants can have non-conservative changes. The variant substitute activation sequences are selected to permit the folded modified corin molecule to be cleaved by a cognate protease, thereby generating an activated modified corin molecule.

Length of the Substitute Activation Sequence

The present invention provides modified corin molecules comprising a substitute activation sequence ranging in size between about 2 to about 10 amino acid residues in length. In one embodiment, the substitute activation sequence is about 2 to about 6 amino acids in length.

The substitute activation sequence can be selected to span the same or similar distance of the activation sequence in a folded wild-type corin molecule. In one embodiment, the substitute activation sequence will not affect the functional activity of the modified corin molecule.

Guidance in determining which and how many amino acid residues can be varied in the substitute activation sequence can be found in the distance spanned by the activation sequence in a folded modified corin molecule. The distance that spans the activation sequence in a folded wild-type corin molecule can be predicted from the amino acid sequence of a wild-type corin molecule and/or obtained experimentally from X-ray crystal structures of a wild-type corin molecule.

For example, the amino acid sequence of wild-type human corin (Yan, W. et al. (1999) supra) can be used as a basis to predict the distance that spans the activation sequence in a folded human wild-type corin molecule. The activation sequence of wild-type human corin molecule, encompassing residues RILGG (SEQ ID NO:42), spans a linear length of five amino acid residues (FIG. 2).

C. Modified Corin Nucleic Acid Molecules of the Invention

Nucleic Acid Molecules Encoding Modified Corin Molecules

The present invention provides various isolated, and recombinant nucleic acid molecules, or fragments or derivatives thereof, comprising polynucleotide sequences encoding the modified corin molecules of the invention, herein referred to as "modified corin polynucleotide sequences," "corin sequences", "corin molecule sequences" or "nucleic acid molecules of the invention". The present invention also provides polynucleotide sequences that encode a fragment or derivative of the modified corin molecules. The present invention further provides related polynucleotide molecules, such as complementary modified corin polynucleotide sequences, or a part thereof, and those that hybridize to the nucleic acid molecules of the invention.

The modified corin polynucleotide sequences are preferably in isolated form, and include, but are not limited to, DNA, RNA, DNA/RNA hybrids, and related molecules, and fragments thereof. Specifically contemplated are genomic DNA, cDNA, ribozymes, and antisense RNA or DNA molecules, as well as nucleic acids molecules based on an alternative backbone or including alternative bases, whether derived from natural sources or synthesized.

The nucleic acid molecules of the invention encode the modified corin molecules of the invention and/or fragments or derivatives thereof, where the encoded modified corin molecule exhibits similar or identical functional activity of a naturally occurring corin molecule.

In one embodiment, an isolated nucleotide sequence encoding a soluble modified corin molecule is shown in FIG. 10, beginning at codon GAT at position 115 and ending at codon AAC at position 2871 (SEQ ID NO:33). The nucleic acid sequence of FIG. 10 encodes the enterokinase activation cleavage sequence DDDDK (SEQ ID NO:44) at position 2134 to 2148. Additionally, the nucleic acid sequence of FIG. 10 encodes an Igκ signal sequence for protein secretion at position 1 to 108 and encodes viral V5 and 6×His epitope tag sequences at position 2871 to 2973.

In accordance with the practice of the invention, the nucleic acid molecules of the invention can be isolated full-length or partial length molecules or oligomers of the modified corin nucleotide sequences. The corin sequence of the invention can encode all or portions of the modified corin molecules of the invention, including the cytoplasmic domain, transmembrane domain, and/or the extracellular domain. The extracellular domain comprises two frizzled-like cysteine-rich domains, eight low density lipoprotein receptor repeats, a macrophage scavenger receptor-like domain, a substitute activation sequence, and a serine protease catalytic domain.

Isolated Nucleic Acid Molecules

The nucleic acid molecules of the invention are preferably in isolated form, where the nucleic acid molecules are substantially separated from contaminant nucleic acid molecules having sequences other than modified corin molecule sequences. A skilled artisan can readily employ nucleic acid isolation procedures to obtain isolated, modified hepsin molecule sequences, see for example Sambrook, J. E. et al. (1989) in *Molecular Cloning*, Cold Spring Harbor Press, N.Y.). The present invention also provides for isolated modified corin molecule sequences generated by recombinant DNA technology or chemical synthesis methods. The present invention also provides nucleotide sequences isolated from various mammalian species including, bovine, porcine, murine, equine, canine, feline, simian, ovine or human, or other sources such as piscine, avian or insect.

The isolated nucleic acid molecules include DNA, RNA, DNA/RNA hybrids, and related molecules, nucleic acid molecules complementary to the modified corin molecule nucleotide sequence encoding a modified corin molecule, or a fragment or derivative thereof, and those which hybridize to the nucleic acid molecules that encode the modified corin molecules. The preferred nucleic acid molecules have nucleotide sequences identical to or similar to the nucleotide sequences disclosed herein. Specifically contemplated are genomic DNA, RNA, e.g., small interfering RNA, cDNA, ribozymes, and antisense molecules.

Identical and Similar Nucleotide Sequences

The present invention provides isolated nucleic acid molecules having a polynucleotide sequence identical or similar to the modified corin molecule sequences disclosed herein. Accordingly, the polynucleotide sequences can be identical to a particular modified corin molecule sequence, for example, as described in FIG. 10. Alternatively, the polynucleotide sequences can be similar to the disclosed sequences.

One embodiment of the invention provides nucleic acid molecules that exhibit sequence identity or similarity with the modified corin molecule nucleotide sequences, such as molecules that have at least 60% to 99.9% sequence similarity and up to 100% sequence identity with the sequences of the invention as described in FIG. 10. Another embodiment provides nucleic acid molecules that exhibit between about 75% to 99.9% sequence similarity, and another embodiment provides molecules that have between about 86% to 99.9% sequence similarity. Yet another embodiment provides molecules that have 100% sequence identity with the modified corin molecule sequences of the invention as described in FIG. 10.

Complementary Nucleotide Sequences

The present invention also provides nucleic acid molecules that are complementary to the sequences as described in FIGS. 1 and 10. Complementarity can be full or partial.

A nucleotide sequence that is fully complementary is complementary to the entire corin sequence as described in any one of FIGS. 1 and 10. A nucleotide sequence that is partially complementary is complementary to only a portion of sequences as described in any one of FIGS. 1 and 10. The complementary molecules include anti-sense nucleic acid molecules. The anti-sense molecules are useful for RNA interference (RNAi), DNA interference, inhibiting growth of a cell or killing a cell expressing a naturally-occurring corin molecule or expressing a modified corin molecule (Yan, W. et al. (1999) supra). The complementary molecules also include small interfering RNA (siRNA) (Elbashir, S. M. et al. (2001) *Nature* 411:494–498; Hammond, S. M. et al. (2001) *Nat. Rev. Genet.* 2:110–119).

Hybridizing Nucleic Acid Molecules

The present invention further provides nucleic acid molecules having polynucleotide sequences that selectively hybridize to the modified corin molecule nucleotide sequence of the invention as shown in any one of FIGS. 1 and 10. The nucleic acid molecules that hybridize can hybridize under high stringency hybridization conditions. Typically, hybridization under standard high stringency conditions will occur between two complementary nucleic acid molecules that differ in sequence complementarity by about 70% to about 100%. It is readily apparent to one skilled in the art that the high stringency hybridization between nucleic acid molecules depends upon, for example, the degree of identity, the stringency of hybridization, and the length of hybridizing strands. The methods and formulas for conducting high stringency hybridizations are well known in the art, and can be found in, for example, Sambrook, J. E. et al. (1989) supra).

In general, stringent hybridization conditions are those that: (1) employ low ionic strength and high temperature for washing, for example, 0.015 M NaCl/0.0015 M sodium titrate/0.1% SDS at 50° C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example of stringent conditions include the use of 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 mg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

Nucleic Acid Fragments

The present invention further provides nucleic acid molecules having fragments of the modified corin molecule sequences of the invention, such as a portion of the modified corin molecule sequences disclosed herein and as shown in any one of FIGS. 1 and 10. The size of the fragment will be determined by its intended use. For example, if the fragment is chosen to encode a modified corin molecule comprising the extracellular domain of a naturally occurring, wild-type corin molecule comprising a substitute activation sequence, then the skilled artisan shall select the polynucleotide fragment that is large enough to encode this domain(s). If the fragment is to be used as a nucleic acid probe or PCR primer, then the fragment length is chosen to obtain a relatively small number of false positives during a probing or priming procedure.

The nucleic acid molecules, fragments thereof, and probes and primers of the present invention are useful for a variety of molecular biology techniques including, for example, hybridization screens of libraries, or detection and quantification of mRNA transcripts as a means for analysis of gene transcription and/or expression. The probes and primers can be DNA, RNA, or derivatives of DNA or RNA molecules. A probe or primer length of at least 15 base pairs is suggested by theoretical and practical considerations (Wallace, B. and Miyada, G. (1987) *Methods Enzymol.* 152: 432–442).

Fragments of the modified corin molecule nucleotide sequences that are particularly useful as selective hybridization probes or PCR primers can be readily identified from the modified corin molecule nucleotide sequences, using art-known methods. For example, sets of PCR primers that bind and/or detect a portion of modified corin molecule transcripts can be made by the PCR method described in U.S. Pat. No. 4,965,188. The probes and primers of this invention can be prepared by methods well known to those skilled in the art (Sambrook, J. E. et al. (1989) supra). The probes and primers can be synthesized by chemical synthesis methods (Gait, M. J., ed. (1984) in *Oligonucleotide Synthesis*, IRL Press, Oxford, England).

One embodiment of the present invention provides nucleic acid primers that are complementary to the modified corin molecule sequences, which allow specific amplification of nucleic acid molecules of the invention or of any specific portions thereof. Another embodiment provides nucleic acid probes that are complementary for selectively or specifically hybridizing to the modified corin molecule sequences or to any portion thereof.

Alternatively, a fragment of the modified corin molecule sequence can be used to construct a recombinant fusion gene having a modified corin molecule sequence fused to a non-corin molecule sequence.

Fusion Gene Sequences

The present invention provides fusion gene sequences, which include a modified corin molecule sequence fused (e.g., linked or joined) to a non-corin molecule sequence. The modified corin molecule sequence is operatively fused, in-frame, to a non-corin molecule sequence.

The fusion gene sequences of the invention include a nucleotide sequence encoding modified corin molecule fused to an epitope tag, including but not limited to, histidine (6×His) tags, V5 tags, FLAG tags, influenza hemagglutinin (HA) tags, Myc tags, VSV-G tags, and thioredoxin (Trx) tags.

The fusion gene sequences of the invention include a nucleotide sequence encoding modified corin molecule fused to a full-length or partial-length reporter gene sequence, including but not limited to glutathione-S-transferase (GST), horseradish peroxidase (HRP), chloramphenicol acetyltransferase (CAT) beta-galactosidase, beta-glucuronidase, luciferase, green fluorescent protein (GFP), and auto-fluorescent proteins including blue fluorescent protein (BFP).

The fusion gene sequences of the invention include a nucleotide sequence encoding modified corin molecule fused to a gene sequence encoding a protein or a fragment of a protein that binds DNA molecules or binds other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions.

The fusion gene sequences of the invention include a nucleotide sequence encoding modified corin molecule fused to a gene sequence encoding a cleavage site moiety. The cleavage site can be located between the modified corin molecule-encoding sequence and the cleavage sequence. The cleavage site moiety includes, but is not limited to hepsin, thrombin, and factor Xa recognition sequences.

Chimeric Nucleotide Sequences

The present invention provides chimeric gene sequences encoding recombinant, chimeric modified corin molecules. The chimeric nucleotide molecules encode a portion of a corin molecule isolated from a first source fused to a portion of a corin molecule isolated from a second, different source. The chimeric molecules encode chimeric polypeptides operatively fused, in-frame.

In one example, a chimeric nucleotide molecule encodes the extracellular domain of a corin molecule from a first source, fused to the cytoplasmic domain of a corin molecule from a second source, where the extracellular domain includes a substitute activation sequence. In another example, a chimeric nucleotide molecule encodes a portion of the extracellular domain of a corin molecule from a first source, fused to the remaining portion of the extracellular domain of a corin molecule from a second source, where the chimeric molecule includes an extracellular domain having a substitute activation sequence.

Codon Usage Variants

The present invention provides isolated codon usage variants that differ from the disclosed modified corin molecule nucleotide sequences, yet do not alter the predicted polypeptide sequence or biological activity of the encoded modified corin molecule. For example, a number of amino acids are designated by more than one triplet codon. Codons that specify the same amino acid can occur due to degeneracy in the genetic code. Examples include nucleotide codons CGU, CGG, CGC, and CGA encoding the amino acid arginine (R); or codons GAU and GAC encoding the amino acid aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The codon usage variants can be generated by recombinant DNA technology. Codons can be selected to optimize the level of production of the modified corin molecule transcript or the modified corin molecule in a particular prokaryotic or eukaryotic expression host, in accordance with the frequency of codon utilized by the host cell. Alternative reasons for altering the nucleotide sequence encoding a modified corin molecule include the production of RNA transcripts having more desirable properties, such as an extended half-life or increased stability. A multitude of variant modified corin molecule nucleotide sequences that encode the respective modified corin molecule can be isolated, as a result of the degeneracy of the genetic code. Accordingly, the present invention provides selecting every possible triplet codon to generate every possible combination of nucleotide sequences that encode the disclosed modified corin molecule, or that encode molecules having the biological activity of the modified corin molecule. This particular embodiment provides isolated nucleotide sequences that vary from the sequences as described in described in any one of FIGS. 1 and 10, such that each variant nucleotide sequence encodes a molecule having sequence identity with the amino acid sequence described in FIGS. 2 and 11.

Variant Nucleotide Sequences

The present invention provides nucleic acid molecules comprising polynucleotide sequences encoding variant forms of any of the modified corin molecules of the invention. The variant nucleotide sequences encode variant forms of the extracellular domain of the modified corin molecule. The variant nucleotide sequences encode variant forms of the substitute activation sequence within the modified corin molecules of the invention. In one embodiment, the variant nucleotide sequence encodes a variant modified corin molecule having the same or similar functional activity of a naturally occurring, wild-type corin molecule.

The variant nucleotide sequences of the present invention include conservative or non-conservative amino acid substitutions. The variant nucleotide sequences include mutations such as amino acid substitutions, deletions, insertions, additions, truncations, or processing or cleavage errors of the protein. The variant nucleotide sequences include allelic, homolog, or ortholog variants of the naturally occurring corin molecule.

Derivative Nucleic Acid Molecules

The nucleic acid molecules of the invention also include derivative nucleic acid molecules which differ from DNA or RNA molecules, and anti-sense molecules. Derivative molecules include peptide nucleic acids (PNAs), and non-nucleic acid molecules including phosphorothioate, phosphotriester, phosphoramidate, and methylphosphonate molecules, that bind to single-stranded DNA or RNA in a base pair-dependent manner (Zamecnik, P. C. et al. (1978) *Proc. Natl. Acad. Sci. USA* 75:280284; Goodchild, P. C. et al. (1986) *Proc. Natl. Acad. Sci. USA* 83:4143–4146). Peptide nucleic acid molecules comprise a nucleic acid oligomer to which an amino acid residue, such as lysine, and an amino group have been added. These small molecules, also designated anti-gene agents, stop transcript elongation by binding to their complementary (template) strand of nucleic acid (Nielsen, P. E. et al. (1993) *Anticancer Drug Des* 8:53–63). Reviews of methods for synthesis of DNA, RNA, and their analogues can be found in Eckstein, E. et al., eds. (1991) in *Oligonucleotides and Analogues*, IRL Press, New York; and Gait, M. J., ed. (1984) in *Oligonucleotide Synthesis*, IRL Press, Oxford, England. Additionally, methods for antisense RNA technology are described in U.S. Pat. Nos. 5,194,428 and 5,110,802. A skilled artisan can readily obtain these classes of derivative nucleic acid molecules using the herein described modified hepsin molecule polynucleotide sequences, see. for example. Egholm, M. et al. (1992) *Innovative and Perspectives in Solid Phase Synthesis*, pp. 325–328, or U.S. Pat. No. 5,539,082.

Labeled Nucleic Acid Molecules

The present invention provides nucleic acid molecules of the invention linked or labeled with a detectable marker. Examples of a detectable marker include, but are not limited to, a radioisotope, a fluorescent compound, a bioluminescent compound, a chemiluminescent compound, a metal chelator or an enzyme. Technologies for generating labeled nucleic acid molecules are well known, see, for example, Sambrook, J. E. et al. (1989) supra.

D. Recombinant Modified Corin Nucleic Acid Molecules

The present invention provides recombinant DNA molecules (rDNAs) that include nucleotide sequences encoding modified corin molecules, or a fragment or derivative thereof, as described herein. As used herein, a rDNA molecule is a DNA molecule that has been subjected to molecular manipulation in vitro. Methods for generating recombinant DNA molecules are well known in the art, for example, see Sambrook, J. E. et al. (1989) supra. In one embodiment, the recombinant DNA molecules of the present invention are operably linked to one or more expression control sequences and/or vector sequences.

Vectors

The nucleic acid molecules of the invention can be recombinant molecules each comprising the polynucleotide sequences, or fragments or derivatives thereof, encoding modified corin molecules linked to a vector to generate a recombinant vector molecule.

The term vector includes, but is not limited to, plasmids, cosmids, BACs, YACs, PACs and phagemids. The vector can be an autonomously replicating vector comprising a replicon that directs the replication of the rDNA within the appropriate host cell. Alternatively, the vector directs integration of the recombinant vector into the host cell. Various viral vectors can also be used, such as, for example, a number of well-known retroviral and adenoviral vectors (Berkner, K. L. (1988) *BioTechniques* 6:616–629).

The vectors of the invention permit expression of the modified corin molecule, or fragments or derivatives thereof, in prokaryotic or eukaryotic host cells. The vectors can be expression vectors, comprising an expression control element, such as a promoter sequence, which enables transcription of the inserted modified corin molecule nucleotide sequence and can be used for regulating the expression (e.g., transcription and/or translation) of a linked modified corin molecule sequence in an appropriate host cell.

The expression control elements can be of various origins, including naturally occurring and synthetic. The naturally occurring elements can be cellular or viral in origin. Expression control elements are known in the art and include, but are not limited to, inducible promoters, constitutive promoters, secretion signals, enhancers, transcription terminators, and other transcriptional regulatory elements.

Other expression control elements that are involved in translation are known in the art, and include the Shine-Dalgarno sequence (e.g., prokaryotic host cells), and initiation and termination codons. Exogenous transcriptional elements and initiation codons can be of various origins, both natural and synthetic.

The promoters can be inducible which are regulated by environmental stimuli or the growth medium of the cells, including those from the genes for heat shock proteins, alcohol dehydrogenase 2, isocytochrome C, acid phosphatase, enzymes associated with nitrogen catabolism, and enzymes responsible for maltose and galactose utilization.

The promoters can be constitutive including yeast beta-factor, alcohol oxidase, cytomegalovirus, and PGH. For reviews, see Ausubel, F. M. et al. (1987) in *Current Protocols in Molecular Biology*, John Wiley & Sons, New York, N.Y.) and Bitter, G. A. et al. (1987) *Methods Enzymol* 153:516–544.

The efficiency of transcription can be augmented by the inclusion of enhancers appropriate to the cell system in use (Scharf, D. et al. (1994) *Results Probl. Cell. Differ.* 20:125–162; Bitter, G. A. et al. (1987) supra). Viral promoters include SV40 early promoter or the promoter included within the LTR of a retroviral vector. Other viral promoters include the cytomegalovirus promoter (Boshart, M. et al. (1985) *Cell* 41:521–530).

Commonly used eukaryotic control sequences for use in expression vectors include promoters and control sequences compatible with mammalian cells such as, for example, CMV promoter and avian sarcoma virus (ASV) (πLN vector). Other commonly used promoters include the early and late promoters from Simian Virus 40 (SV40) (Fiers, W. et al. (1978) *Nature* 273:113–120), or other viral promoters such as those derived from polyoma, Adenovirus 2, and bovine papilloma virus. An inducible promoter, such as hMTII (Karin, M. et al. (1982) *Nature* 299:797–802) can also be used.

Transcriptional control sequences for yeast vectors include promoters for the synthesis of glycolytic enzymes (Hess, B. et al. (1968) *J. Adv. Enzyme Reg.* 7:149; Holland, M. J. and Holland, J. P. (1978) *Biochemistry* 17:4900–4097). Additional promoters known in the art include the CMV promoter provided in the CDM8 vector (Toyama, R. and Okayama, H. (1990) *FEBS Lett.* 268:217–221); the promoter for 3-phosphoglycerate kinase (Hitzeman, R. A. et al. (1980) *J. Biol. Chem.* 255:12073–12080), and those for other glycolytic enzymes.

Specific translation initiation signals can also be required for efficient translation of a modified corin molecule sequence. These signals include the ATG initiation codon and adjacent sequences. The ATG initiation sequences or upstream sequences of a naturally occurring corin molecule can be inserted into the appropriate expression vector. Alternatively, a synthetic ATG initiation codon and other sequences can be used. The ATG initiation codon must be in the correct reading-frame to ensure translation of the insert sequence.

The expression control elements can be placed at the 3' end of the coding sequences. These sequences can act to stabilize messenger RNA. Such terminators are found in the 3' untranslated region following the coding sequences in several yeast-derived and mammalian genes.

The expression vector can include at least one selectable marker gene encoding a gene product that confers drug resistance, such as resistance to kanamycin, ampicillin or tetracyline.

The expression vector can include any marker gene. These include, but are not limited to, the herpes simplex virus thymidine kinase (Wigler, M. et al. (1977) *Cell* 11:223–232) and adenine phosphoribosyltransferase (Lowy, I. et al. (1980) *Cell* 22:817–823) genes which can be employed in tk-minus or aprt-minus cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci. USA* 77:3567–3570); npt, which confers resistance to the aminoglycosides neomycin and G-418 (Colbere-Garapin, F. et al. (1981) *J. Mol. Biol.* 150:1–14) and als or pat, which confer resistance to chlorsulfuron and phosphinotricin acetyltransferase, respectively (Murry, L. E. (1992) in *McGraw Yearbook of Science and Technology*, McGraw Hill, New York, N.Y., pp 191–196). Additional selectable genes have been described, for example, trpB, which allows cells to utilize indole in place of tryptophan, or hisD, which allows cells to utilize histinol in place of histidine (Hartman, S. C. and Mulligan, R. C. (1988) *Proc. Natl. Acad. Sci. USA* 85:8047–8051). Recently, the use of visible markers has gained popularity with such markers as anthocyanins, β-glucuronidase and its substrate, GUS, and luciferase and its substrate, luciferin, being widely used not only to identify transformants, but also to quantify the amount of transient or stable protein expression attributable to a specific vector system (Rhodes, C. A. et al. (1995) *Methods Mol. Biol.* 55:121–131).

The vector also comprises multiple endonuclease restriction sites that enable convenient insertion of exogenous DNA sequences. Methods for generating a recombinant expression vector encoding the modified corin molecules of the invention are well known in the art (Sambrook, J. E. et al. (1989) supra; Ausubel, F. M. et al. (1989) supra).

The expression vectors used for generating modified corin molecules are compatible with eukaryotic host cells. The vectors can be compatible with vertebrate cells. These vectors can include expression control elements such as promoters and/or enhancers from mammalian genes or mammalian viruses. Other expression vectors can include tissue- or cell-specific promoters and/or enhancers from mammalian genes or mammalian viruses.

The expression vectors can be compatible with other eukaryotic host cells, including insect, plant, or yeast cells. The expression vectors can include expression control elements, such as the baculovirus polyhedrin promoter for expression in insect cells. The promoters and/or enhancers derived from plant cells (e.g., heat shock, RUBISCO, storage protein genes), viral promoters or leader sequences or from plant viruses can also be used.

Eukaryotic cell expression vectors are well known in the art and are available from several commercial sources, including PSVL and pKSV-10 (Pharmacia), pBPV-1/pML2d (International Biotechnologies, Inc.), pTDT1 (ATCC, #31255), and similar eukaryotic expression vectors. Examples of expression vectors for eukaryotic host cells include, but are not limited to, vectors for mammalian host cells including: BPV-1; pHyg; pRSV; pSV2; pTK2; pIRES (Clontech); pRc/CMV2; pRc/RSV; pSFV1 (Life Technologies); pVPakc Vectors; pCMV vectors; pSG5 vectors (Stratagene); retroviral vectors (e.g., pFB vectors (Stratagene)); pCDNA-3 (Invitrogen) or modified forms thereof; adenoviral vectors; Adeno-associated virus vectors; baculovirus vectors. Other expression vectors for eukaryotic host cells include pESC vectors (Stratagene) for yeast and pFastBac for expression in insect cells (Gibco/BRL, Rockville, Md.).

The expression vectors can include expression control elements for expression in bacterial host cells. These expression control elements can be induced by environmental conditions, such as heat-shock, or by addition of agents such as isopropyl-β-D-thiogalactopyranoside (e.g., IPTG) (Yamaguchi, N. et al. (2002) *J. Biol. Chem.* 277:6806–6812). Prokaryotic cell expression vectors are well known in the art and are available from several commercial sources. For example, pGEX vector (Promega, Madison, Wis.), pTrcHisB vector (Invitrogen), pET vector (e.g., pET-21, Novagen Corp.), BLUESCRIPT phagemid (Stratagene, LaJolla, Calif.), pSPORT (Gibco BRL, Rockville, Md.), or ptrp-lac hybrids can be used to express the modified corin molecules in bacterial host cells.

E. Modified Corin Host-Vector Systems

The present invention further provides a host-vector system comprising a vector, plasmid, phagemid, BAC, PAC, YAC or cosmid comprising a modified corin molecule nucleotide sequence, or a fragment or derivative thereof, introduced into a suitable host cell.

The host-vector system can be used to transcribe and/or express (e.g., produce) the modified corin molecules of the invention. A variety of expression vector/host systems can be utilized to carry and express the modified corin molecule sequences. The host cell can be either prokaryotic or eukaryotic.

Eukaryotic Host Cells

Examples of suitable eukaryotic host cells include insect cells, yeast cells, plant cells, or animal cells such as mammalian cells.

An expression system that can be used to express modified corin molecules is an insect system. In one such system, *Autographa californica* nuclear polyhedrosis virus (AcNPV) can be used as a vector to express foreign genes in *Spodoptera frugiperda* insect cells or in *Trichoplusia larvae*. The sequence encoding a modified corin molecule can be cloned into a nonessential region of the virus, such as the polyhedrin gene, and placed under control of the polyhedrin promoter. Successful insertion of a modified corin molecule nucleotide sequence will render the polyhedrin gene inactive and produce recombinant virus lacking coat protein. The recombinant viruses can then used to infect *S. frugiperda* cells or *Trichoplusia larvae* in which the modified corin molecule can be expressed (Smith, G. E. et al. (1983) *J.*

Virol. 46:584–593; Engelhard, E. K. et al. (1994) *Proc. Natl. Acad. Sci. USA* 91:3224–3227).

In mammalian host cells, a number of viral-based expression systems can be utilized. In cases where an adenovirus is used as an expression vector, a modified corin molecule nucleotide sequence can be ligated into an adenovirus transcription/translation vector having the late promoter and tripartite leader sequence. Insertion in a nonessential E1 or E3 region of the viral genome results in a viable virus capable of expressing a modified corin molecule in infected host cells (Logan, J. and Shenk, T. (1984) *Proc. Natl. Acad. Sci. USA* 81:3655–3659). In addition, transcription enhancers, such as the Rous sarcoma virus (RSV) enhancer, can be used to increase expression in mammalian host cells.

In a previous study, human embryonic kidney (HEK) 293 cells were transfected with a plasmid comprising human corin cDNA using a Lipofectin-mediated transfection procedure. The transfected HEK293 cells expressed human corin, which activated pro-ANP (Yan, W. et al. (2000) supra).

In yeast, *Saccharomyces cerevisiae*, a number of vectors including constitutive or inducible promoters such as betafactor, alcohol oxidase and PGH can be used. For reviews, see Ausubel, F. M. et al. (1989) supra and Bitter, G. A. et al. (1987) supra.

In cases where plant expression vectors are used, the expression of a sequence encoding a modified corin molecule can be driven by any of a number of promoters. For example, viral promoters such as the 35S and 19S promoters of CaMV (Brisson, N. et al. (1984) *Nature* 310:511–514) can be used alone or in combination with the omega leader sequence from TMV (Takamatsu, N. et al. (1987) *EMBO J.* 6:307–311). Alternatively, plant promoters such as the small subunit of RUBISCO (Coruzzi, G. et al. (1984) *EMBO J.* 3:1671–1680; Broglie, R. et al. (1984) *Science* 224:838–843); or heat shock promoters (Winter, J. and Sinibaldi, R. M. (1991) *Results Probl. Cell Differ.* 17:85–105) can be used.

In addition, a host cell strain can be chosen for its ability to modulate the expression of the inserted modified corin molecule nucleotide sequences or to process the expressed protein in the desired fashion. Such modifications of the expressed modified corin molecule include, but are not limited to, acetylation, carboxylation, glycosylation, phosphorylation, lipidation, and acylation. Post-translational processing which cleaves a precursor form of the protein (e.g., a pre-pro-protein) can also be important for correct insertion, folding and/or function. Different host cells such as CHO, HeLa, MDCK, 293, WI38, and the like, have specific cellular machinery and characteristic mechanisms for such post-translational activities and can be chosen to ensure the correct modification and processing of the introduced foreign protein.

Prokaryotic Host Cells

Examples of suitable prokaryotic host cells include bacteria strains from genera such as *Escherichia, Bacillus, Pseudomonas, Streptococcus*, and *Streptomyces*. For example, bacterial cells, such as Epicurian coli XL-1 Blue cells (Stratagene) which have been previously used to produce a naturally-occurring hepsin (Kazama, Y. et al. (1995) *J. Biol. Chem.* 270:66–72) can also be used to produce the modified corin molecule.

In bacterial systems, a number of expression vectors can be selected depending upon the use intended for the modified corin molecules. For example, when large quantities of the modified corin molecules are needed, for example for the induction of antibodies, vectors that direct high level expression of fusion proteins that are soluble and readily purified can be desirable. Such vectors include, but are not limited to, the multifunctional *E. coli* cloning and expression vectors such as BLUESCRIPT (Stratagene), in which the modified corin molecule nucleotide sequence can be ligated into the vector in-frame with sequences for the amino-terminal Met and the subsequent 7 residues of galactosidase so that a hybrid protein is produced. Other vectors include the pIN vectors (Van Heeke, G. and Schuster, S. M. (1989) *J. Biol. Chem.* 264:5503–5509), and the like. The pGEX vectors (Promega, Madison Wis.) can also be used to express foreign proteins as fusion proteins with glutathione-S-transferase (GST). In general, such fusion proteins are soluble and can easily be purified from lysed cells by adsorption to glutathione-agarose beads followed by elution in the presence of free glutathione. Proteins made in such systems are designed to include hepsin, thrombin or factor Xa protease cleavage sites so that the cloned protein of interest can be released from the GST moiety at will.

Methods for Introducing Modified Corin Nucleic Acid Sequence into Host Cells

The methods for introducing the modified corin molecule nucleotide sequences into the host cells are well-known methods that depend on the type of vector used and host system employed.

For example, in vertebrate cells, the nucleic acid sequences are introduced with vectors using various methods, including calcium phosphate-mediated DNA transfection (Graham, F. L. and Van der Eb, A. J. (1973) *Virology* 52:456–467; Wigler, M. et al. (1977) supra) or other cationic-mediated transfection methods, electroporation (Neuman, E. et al. (1982) *EMBO J.* 1:841–845), microinjection Anderson, W. F. et al. 1(980) *Proc. Natl. Acad. Sci. USA* 77:5399–5403; Cappechi, M. R. (1980) *Cell* 22:479–488; Graessman, A. et al. (1979) *J. Virol.* 32:989–994), or lipid methods including encapsulation of DNA in lipid vesicles (Schaefer-Ridder, M. (1982) *Science* 215:166–168). Other methods include the particle gun method. Still other methods include using an adenovirus transcription/translation vector comprising the late promoter and tripartite leader sequence. A nucleic acid sequence can be inserted in a nonessential E1 or E3 region of the adenoviral genome to create a viable virus capable of expressing the protein encoded by the nucleic acid sequence (Logan, J. and Shenk, T (1984) supra). Alternatively, retroviral transfer methods can be used (Gilboa, E. et al. (1986) *BioTechniques* 4:504–512).

Plant cells can be introduced by direct DNA transformation or pathogen-mediated transfection. For reviews of such techniques, see Hobbs, S. (1992) in *McGraw Yearbook of Science and Technology*, McGraw Hill, New York, N.Y., pp 191–196 and Weissbach, A. and Weissbach, H. (1988) in *Methods for Plant Molecular Biology*, Academic Press, New York, N.Y., pp 421–463. Alternatively, plant cells can be introduced via a particle-gun method using metal particles.

Prokaryotic host cells are introduced (e.g., transformed) with nucleic acid molecules by electroporation or salt treatment methods (Cohen, S. N. et al. (1972) *Proc. Natl. Acad. Sci. USA* 69:2110–2114; Sambrook, J. E. et al. (1989) supra).

Selection of Transformed Cells

The cells introduced with the modified corin molecule nucleotide sequences can be identified by techniques well known in the art. The cells can be selected, lysed and their DNA content examined for the presence of the introduced sequences using a DNA gel blot method or similar method (Southern, E. M. (1975) *J. Mol. Biol.* 98:503–517; Berent, S. L. et al. (1985) *Biotechniques* 3:208–220). Alternatively, the proteins produced from the cells of the invention can be assayed via a biochemical assay or an immunological method.

Any number of selection systems can be used to recover the introduced (e.g, transformed or transfected) cells. The introduced cells can be selected based on expression of herpes simplex virus thymidine kinase (Wigler, M. et al. (1977) supra), or adenine phosphoribosyltransferase (Lowy, I. et al. (1980) *Cell* 22:817–23) genes which can be employed in tk-minus or aprt-minus cells, respectively. Also, antimetabolite, antibiotic or herbicide resistance can be used as a basis for selection; for example, dhfr which confers resistance to methotrexate (Wigler, M. et al. (1980) supra); npt, which confers resistance to the aminoglycosides neomycin and G-418 (Colbere-Garapin, F. et al. (1981) supra) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman, S. C. and Mulligan, R. C. (1988) supra). Recently, the use of visible markers has gained popularity with such markers as anthocyanins, beta-glucuronidase and its substrate, GUS, and luciferase and its substrate, luciferin, being widely used not only to identify transformants, but also to quantify the amount of transient or stable protein expression attributable to a specific vector system (Rhodes, C. et al. (1995) supra).

F. Cell and Gene Therapy

A modified corin molecule of the invention may be employed in accordance with the present invention by expression of such modified corin molecule in vivo by a method referred to as "cell therapy". Thus, for example, cells may be engineered with a polynucleotide (DNA or RNA) encoding the modified corin molecule ex vivo, and the engineered cells are then provided to a patient to be treated with the modified corin molecule. Such methods are well known in the art. For example, cells may be engineered by procedures known in the art by use of a retroviral particle containing RNA encoding the modified corin molecule of the present invention.

A modified corin molecule of the invention may also be employed in accordance with the present invention by expression of such modified corin molecule in vivo by a method referred to as "gene therapy". Thus, for example, a virus may be engineered with a polynucleotide (DNA or RNA) encoding the modified corin molecule, and the engineered virus is then provided to a patient to be treated with the modified corin molecule. Such methods are well known in the art. For example, recombinant adenoviruses may be engineered by procedures known in the art containing DNA encoding the modified corin molecule of the present invention.

Local delivery of the modified corin molecules of the present invention using cell or gene therapy may provide the therapeutic agent to the target area, the endothelial cells lining blood vessels.

Both in vitro and in vivo cell and gene therapy methodologies are contemplated. Several methods for transferring potentially therapeutic genes to defined cell populations are known. See, e.g., Mulligan, R. C. (1993) *Science* 260: 926–932. These methods include: direct gene transfer (see, e.g., Wolff, J. A. et al. (1990) *Science* 247: 1465–1468); liposome-mediated DNA transfer (see, e.g., Caplen, N. J. et al. (1995) *Nature Med.* 3:39–46; Crystal, R. G. (1995) *Nature Med.* 1:15–17; Gao, X. and Huang, L. (1991) *Biochem. Biophys. Res. Comm.* 179:280–285); retrovirus-mediated DNA transfer (see, e.g., Kay, M. A. et al. (1993) *Science* 262:117–119; Anderson, W. F. (1992) *Science* 256: 808–813); and DNA virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali, M. et al. (1994) *Gene Therapy* 1:367–384; U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. See Naldini, L. et al. (1996) *Science* 272:263–267.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Adenoviruses have the advantage that they have a broad host range, can infect quiescent or terminally differentiated cells, such as neurons or hepatocytes, and appear essentially non-oncogenic. See, e.g., Ali, M. et al. (1994), supra. Adenoviruses do not appear to integrate into the host genome. Because they exist extrachromosomally, the risk of insertional mutagenesis is greatly reduced. Ali, M. et al. (1994), supra.

Adeno-associated viruses exhibit similar advantages as adenoviral-based vectors. However, MVs exhibit site-specific integration on human chromosome 19 (Ali, M. et al. (1994), supra).

In a preferred embodiment, the DNA encoding the modified corin molecules of this invention is used in cell or gene therapy for cardiovascular diseases including, but not limited to, heart failure, hypertension, cardiac hypertrophy, cardiomyopathy, cardiac fibrosis, ischemic heart disease, valvular heart disease, myocarditis, and preeclampsia.

According to this embodiment, cell or gene therapy with DNA encoding the modified corin molecules of this invention is provided to a patient in need thereof, concurrent with, or immediately after diagnosis.

The skilled artisan will appreciate that any suitable gene therapy vector containing DNA encoding the modified corin molecule of the invention or DNA encoding fragments or derivatives of the modified corin molecules of the invention may be used in accordance with this embodiment. The techniques for constructing such a vector are known. See, e.g., Anderson, W. F. (1998) *Nature* 392:25–30; Verma, I. M. and Somia, N. (1998) *Nature* 389:239–242. Introduction of the modified corin molecule DNA-containing vector to the target site may be accomplished using known techniques.

The cell or gene therapy vector includes one or more promoters. Suitable promoters which may be employed include, but are not limited to, the retroviral LTR; the SV40 promoter; and the human cytomegalovirus (CMV) promoter described in Miller, A. D and Rosman, G. J. (1989) *Biotechniques* 7:980–990, or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the modified corin molecule of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoter.

The retroviral plasmid vector is employed to transduce packaging cell lines to form producer cell lines. Examples of packaging cells which maybe transfected include, but are not limited to, the PE501, PA317, ψ-2, ψ-AM, PA12, T19-14X; VT-19-17-H2, ψCRE, ψCRIP, GP+#-86, GP+envAm12, and DAN cell lines as described in Miller, A. D. (1990) *Hum. Gene Ther.* 1:5–14, which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host. The producer cell line generates infectious retroviral vector particles, which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient. U.S. Pat. Nos. 5,641,670 and 5,733,761 disclose in detail this concept, and are hereby incorporated by reference in their entirety.

G. Pharmaceutical Compositions

The present invention provides pharmaceutical compositions comprising the molecules of the invention admixed with an acceptable carrier or adjuvant that is known to those of skill of the art. The pharmaceutical compositions preferably include suitable carriers and adjuvants which include any material which when combined with a molecule of the invention retains the molecule's activity and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g., oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers can also include sterile solutions; tablets, including coated tablets and capsules. Typically such carriers include excipients such as starch, milk, sugar (e.g., sucrose, glucose, maltose), certain types of clay, gelatin, stearic acid or salts thereof, magnesium or calcium stearate, talc, vegetable fats or oils, gums, glycols, or other known excipients. Such carriers can also include flavor and color additives or other ingredients. Compositions comprising such carriers are formulated by well-known conventional methods. Such compositions can also be formulated within various lipid compositions, such as, for example, liposomes as well as in various polymeric compositions, such as polymer microspheres.

H. Kits

This invention further relates to kits for research or diagnostic purposes. Kits typically include one or more containers containing the modified corin molecules of the present invention. In a preferred embodiment, the kits comprise containers containing modified corin molecules in a form suitable for derivatizing with a second molecule. In a more preferred embodiment the kits comprise containers containing the modified corin molecule of SEQ ID NO:34. Further provided are kits comprising compositions of the invention, in free form or in pharmaceutically acceptable form. The kit can comprise instructions for its administration. The kits of the invention can be used in any method of the present invention.

In another embodiment, the kits may contain DNA sequences encoding the modified corin molecules of the invention. Preferably the DNA sequences encoding these modified corin molecules are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various modified corin molecules. The plasmids may also contain numerous other elements to facilitate cloning and expression of the encoded proteins. Such elements are well known to those of skill in the art and include, for example, selectable markers, initiation codons, termination codons, and the like. In a more preferred embodiment the kits comprise containers containing the DNA sequences of SEQ ID NO:33.

I. Utility of the Modified Corin Molecules of the Invention

The modified corin molecules of the invention are useful for treating cardiovascular diseases of any etiology, including, but not limited to, heart failure, hypertension, cardiac hypertrophy, cardiomyopathy, cardiac fibrosis, ischemic heart disease, valvular heart disease, myocarditis, and preeclampsia.

J. Testing of the Modified Corin Molecules of the Invention

The in vitro utility of the modified corin molecules of the invention may be tested in the assays described in Examples 3 to 5, and in the neonatal rat cardiomyocyte hypertrophy model (van Rooij, E. et al. (2002) *J. Biol. Chem.* 277: 48617–48626 and Liang, F. et al. (2003) *J. Biol. Chem.* 278:15073–15083).

The in vivo utility of the modified corin molecules of the invention may be tested in the assays described in Example 6, and in the mouse myocardial infarction model after coronary artery ligation (Feng, Q. et al. (2001) *Circulation* 104:700–704), the mouse pressure overload model after aortic constriction performed by transverse thoracic aorta ligation (Meguro, T. et al. (1999) *Circ. Res.* 84:735–740), the mouse pressure overload model (Rockman, H. A. et al. (1991) *Proc. Natl. Acad. Sci. USA* 88:8277–8281), the mouse genetic model (Beggah, A. T. et al. (2002) *Proc. Natl. Acad. Sci USA* 99:7160–7165), the cardiomyopathic hamster hypothermic-cardioplegia model (Hoshijima, M. et al. (2002) *Nature Med.* 8:864–871 and Ikeda, Y. et al. (2002) *Circulation* 105:502–508), and the dog pacing heart failure model (Shen, W. et al. (2002) *J. Pharmacol. Exp. Ther.* 303:673–680 and Shen, W. et al. (1999) *Circulation* 100: 2113–2118).

K. Administration of the Modified Corin Molecules of the Invention

Administration of the modified corin molecules of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a modified corin molecule of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a modified corin molecule(s) of the invention, or a pharmaceutically acceptable salt thereof, and 99% to 1% by weight of a suitable pharmaceutical excipient. Preferably, the composition will be about 5% to 75% by weight of a modified corin molecule(s) of the invention, or a pharmaceutically acceptable salt thereof, with the rest being suitable pharmaceutical excipients.

One preferred route of administration is oral, using a convenient daily dosage regimen, which can be adjusted according to the degree of severity of the disease-state to be treated. For such oral administration, a pharmaceutically acceptable composition containing a modified corin molecule(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations, and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

Another preferred route of administration is parenteral, for example, intravenous, subcutaneous, or intramuscular administration, wherein the modified corin molecules of the present invention can be used in pharmaceutical compositions. Thus, the above described modified corin molecules preferably will be combined with an acceptable sterile pharmaceutical carrier, such as five percent dextrose, lactated Ringer's solution, normal saline, sterile water, or any other commercially prepared physiological buffer solution designed for intravenous infusion. It will be understood that the selection of the carrier solution and the dosage and administration of the composition will vary with the subject and the particular clinical setting, and will be governed by standard medical procedures.

Administration of the fusion protein may be by a bolus intravenous injection, by a constant intravenous infusion or by a combination of both routes. Alternatively, or in addition, the fusion protein mixed with appropriate excipients may be taken into the circulation from an intramuscular or subcutaneous site. A typical pharmaceutical composition for intravenous, subcutaneous or intramuscular administration can be readily determined by one of ordinary skill in the art. The amounts administered are clearly protein specific and depend on its potency and pharmacokinetic profile. Actual methods for preparing parenterally administrable compositions will be known or apparent to those skilled in the art and are described in more detail in such publications as *Remington's Pharmaceutical Science,* 18$^{th}$ Ed. (Mack Publishing Company, Easton, Pa., 1990). Single or multiple administration of the compositions may be administered depending on the dosage and frequency as required and tolerated by the patient. In any event, the composition should provide a sufficient quantity of the proteins of this invention to effectively treat the patient.

The modified corin molecules of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a modified corin molecule(s) of the invention (about 0.5% to about 20%), or a pharmaceutically acceptable salt thereof, and optional pharmaceutical adjuvants in a carrier, such as, for example, water, saline, aqueous dextrose, glycerol, ethanol, and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a modified corin molecule of the invention, or a pharmaceutically acceptable salt thereof, for treatment of a disease-state characterized by elevated blood pressure in accordance with the teachings of this invention.

The modified corin molecules of the invention, or their pharmaceutically acceptable salts, are administered in a therapeutically effective amount which will vary depending upon a variety of factors including the activity of the specific modified corin molecule employed; the metabolic stability and length of action of the modified corin molecule; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a modified corin molecule of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a modified corin molecule of the invention, or a pharmaceutically acceptable salt thereof, preferably from about 50 mg to about 700 mg per day, and most preferably from about 100 mg to about 500 mg per day.

L. Preferred Embodiments

Of the modified corin molecules of the invention as set forth above in the Summary of the Invention, several groups of modified corin molecules are particularly preferred.

In one preferred embodiment, the modified corin molecule of the invention comprises the extracellular domain of corin, or fragment or derivative thereof, and a substitute activation sequence that replaces the wild-type corin activation sequence RILGG (SEQ ID NO:42).

In a more preferred embodiment, the modified corin molecule of the invention comprises the extracellular domain of corin, or fragment or derivative thereof, and the substitute activation sequence DDDDKILGG (SEQ ID NO:43), which replaces the wild-type corin activation sequence RILGG (SEQ ID NO:42).

In a yet more preferred embodiment, the modified corin molecule of the invention comprises the extracellular domain of corin, or fragment or derivative thereof, and the substitute activation sequence DDDDKILGG (SEQ ID NO:43), which replaces the wild-type corin activation sequence RILGG (SEQ ID NO:42), and further comprises an N-terminal Igκ signal sequence and C-terminal epitope tags.

The modified corin molecule of SEQ ID NO:34 is a preferred embodiment of this invention.

The following specific examples are provided as a guide to assist in the practice of the invention, and are not intended as a limitation on the scope of the invention.

EXAMPLE 1

Construction of Human Corin Expression Vectors

To examine processing of pro-peptides by corin in vitro, mammalian expression vectors encoding the full-length human corin polypeptide and derivatives thereof were constructed.

Construction of a Full-Length Human Corin Expression Vector

The wild-type human corin cDNA was cloned from a human heart cDNA library (Yan, W. et al. (1999) supra). The full-length human corin cDNA sequence is 4933 nucleotides in length, and the human corin coding sequence, including the translation initiation methionine codon and the translation termination codon, is 3129 nucleotides in length (see FIG. 1, SEQ ID NO:1). The wild-type corin polypeptide sequence consists of 1042 amino acids (see FIG. 2, SEQ ID NO:2) with a calculated mass of ~116 kDa (Yan, W. et al. (1999) supra).

A plasmid construct containing the full-length human corin cDNA was generated as described (Yan, W. et al. (2000) supra). The human corin coding region, from the translation initiation codon at position 94 to the C-terminal amino acid at position 3219, was amplified by PCR using a forward primer (5'-ATGAAACAGTCTCCTGC-CCTCGCTCCGGAAGAGC-3'; SEQ ID NO:3) and a reverse primer (5'-GTTTAGGAGAAAGGTCTGGATGTA-3'; SEQ ID NO:4), and inserted into the PCR product site of mammalian expression vector pcDNA3.1N5-His-TOPO (Invitrogen). The recombinant corin generated using this expression vector contains C-terminal viral V5 epitope and 6×His tags, thereby facilitating detection of the recombinant protein by anti-V5 or anti-His antibodies. The resultant plasmid, pcDNA3.1Corin, which was confirmed by restriction enzyme digestion and by DNA sequencing, expresses a recombinant corin consisting of human corin amino acids 1 to 1042, followed by the C-terminal V5 epitope and 6×His tags.

Construction of Transmembrane-Containing Human Corin Deletion Mutant Expression Vectors To facilitate the generation of recombinant corin molecules containing internal deletions, a XhoI restriction site was introduced into the full-length human corin cDNA sequence by PCR methodology as follows. Using pcDNA3.1 Corin as DNA template (see above), the N-terminal region of human corin, from position 1 to 369 in SEQ ID NO:1, which corresponds to amino acids 1 to 123 of SEQ ID NO:2, was amplified by PCR using a forward primer Cor/TMa (5'-GGGGGAATTCATGAAACAGTCTCCTGC-CCTCGCTCCGGAAGAGC-3'; SEQ ID NO:5) and a reverse primer Cor/TMb (5'-GGGGCTCGAGCGTAGTC-CAGGCTGGAACGTGTTGGTCG-3'; SEQ ID NO:6). The PCR product was digested with EcoRI and XhoI (New England Biolabs) and inserted into the EcoRI and XhoI sites of pcDNA4/HisMaxC (Invitrogen). This intermediate plasmid is pcDNA4NCorin1. Again using pcDNA3.1 Corin as DNA template, the C-terminal region of human corin, from position 370 to 3129 in SEQ ID NO:1, which corresponds to amino acids 124 to 1042 and the termination codon of SEQ ID NO:2, was amplified by PCR using a forward primer CorFL (5'-GGGGCTCGAGGATGCTTCTCTCCCAGGG-GACCMAGTCACAGG-3'; SEQ ID NO:7) and a reverse primer CorEnd (5'-GGGGGGGCCCTTAGTTTAG-GAGAAAGGTCTGGATGTMATCTG-3'; SEQ ID NO:8). The PCR product was digested with XhoI and ApaI (New England Biolabs) and inserted into the XhoI and ApaI sites of pcDNA4NCorin1. The resultant plasmid, pcDNA4FLCorin, expresses a recombinant corin consisting of human corin amino acids 1 to 123, a two amino acid insertion (Leu-Glu) due to the introduction of the XhoI site (CTCGAG), and human corin amino acids 124 to 1042 (SEQ ID NO:9).

Internal deletion mutants 1 to 5 were generated in the transmembrane form of human corin by PCR methodology as follows. Using pcDNA3.1 Corin as DNA template, C-terminal regions of human corin were amplified by PCR using the forward primers CorDel I (5'-GGGGCTCGAGCTCT-GTGGAAGGGGTGAGAACTTTCTGTGTGC-3', SEQ ID NO:10), CorDel II (5'-GGGGCTCGAGCTGAATAACTG-TAGTCAATGTGAACC-3', SEQ ID NO:11), CorDel III (5'-GGGGCTCGAGGTGGAAGAATGCTCAC-CTAGTCATTTCAAG-3', SEQ ID NO:12), CorDel IV (5'-GGGGCTCGAGGTGTGTGCAGATGGCTG-GCAGGAGATATTG-3', SEQ ID NO:13), and CorDel V (5'-GGGGCTCGAGGACTGTGGGCGCCGCCCT-GCTGCCCGAATG-3'; SEQ ID NO:14), and reverse primer CorEnd (SEQ ID NO:8). The individual PCR products were digested with XhoI and ApaI and inserted into the XhoI and ApaI sites of pcDNA4NCorin1. The resultant plasmids express recombinant corin polypeptides consisting of human corin amino acids 1 to 123, a two amino acid insertion (Leu-Glu), and human corin amino acids 268 to 1042 (Deletion 1, SEQ ID NO:15), 449 to 1042 (Deletion 2, SEQ ID NO:16), 577 to 1042 (Deletion 3, SEQ ID NO:17), 713 to 1042 (Deletion 4, SEQ ID NO:18) or 789 to 1042 (Deletion 5, SEQ ID NO:19).

Internal deletion 6 was generated in the transmembrane form of human corin by PCR methodology as follows. Using pcDNA3.1 Corin as DNA template, the N-terminal region of human corin, from position 1 to 777 in SEQ ID NO:1, which corresponds to amino acids 1 to 259 of SEQ ID NO:2, was amplified by PCR using forward primer Cor/TMa (SEQ ID NO: 5) and reverse primer Del 62 (5'-GGGGCTCGAGAG-GTGAGAAGCAAATTCTGCTGACATTGC-3'; SEQ ID NO:20). The PCR product was digested with EcoRI and XhoI (New England Biolabs) and inserted into the EcoR1 and XhoI sites of pcDNA4/HisMaxC (Invitrogen). This intermediate plasmid is pcDNA4NCorin2. Using pcDNA3.1Corin as DNA template, the C-terminal region of human corin, from position 1247 to 3129 in SEQ ID NO:2, which corresponds to amino acids 415 to 1042 of SEQ ID NO:2, was amplified by PCR using forward primer Del 61 (5'-GGGGCTCGAGAGCGTCATTCAGACT-TCATGTCAAGMGG-3'; SEQ ID NO:21) and reverse primer CorEnd (SEQ ID NO:8). This PCR product was digested with XhoI and ApaI and inserted into the XhoI and ApaI sites of pcDNA4NCorin2. The resultant plasmid expresses a recombinant corin consisting of human corin amino acids 1 to 259, Leu-Glu, and human corin amino acids 415 to 1042 (Deletion 6, SEQ ID NO:22).

Internal deletion 7 was generated in the transmembrane form of human corin by PCR methodology as follows. Using pcDNA3.1 Corin as DNA template, the N-terminal region of human corin, from position 1 to 1347 in SEQ ID NO:1, which corresponds to amino acids 1 to 449 of SEQ ID NO:2, was amplified by PCR using forward primer Cor/TMa (SEQ ID NO: 5) and reverse primer Del 72 (5'-GGGGCTC-GAGAGGTGAGAAGCAAATTCTGCTGACATTGC-3'; SEQ ID NO:23). The PCR product was digested with EcoRI and XhoI (New England Biolabs) and inserted into the EcoR1 and XhoI sites of pcDNA4/HisMaxC (Invitrogen). This intermediate plasmid is pcDNA4NCorin3. Using pcDNA3.1Corin as DNA template, the C-terminal region of human corin, from position 1705 to 3129 in SEQ ID NO:1, which corresponds to amino acids 569 to 1042 of SEQ ID NO:2, was amplified by PCR using forward primer Del 71 (5'-GGGGCTCGAGACCTGCCTGATGCCTGAT-GAATATGTGG-5', SEQ ID NO:24) and reverse primer CorEnd (SEQ ID NO:8). This PCR product was digested with XhoI and ApaI and inserted into the XhoI and ApaI sites of pcDNA4NCorin3. The resultant plasmid expresses a recombinant corin consisting of human corin amino acids 1 to 449, Leu-Glu, and human corin amino acids 569 to 1042 (Deletion 7, SEQ ID NO:25).

The schematic structures of the full-length human corin and transmembrane-containing human corin internal deletion mutants are depicted in FIG. 3. They are: Deletion 1 (SEQ ID NO:15), which is missing the CRD1 domain (amino acids 124 to 267); Deletion 2 (SEQ ID NO:16) which is missing the CRD1 and LDLR1–5 domains (amino acids 124 to 448); Deletion 3 (SEQ ID NO:17), which is missing the CRD1, LDLR1–5 and CRD2 domains (amino acids 124 to 576); Deletion 4 (SEQ ID NO:18), which is missing the CRD1, LDLR1–5, CRD2 and LDLR6–8 domains (amino acids 124 to 712); Deletion 5 (SEQ ID NO:19), which is missing the CRD1, LDLR1–5, CRD2, LDLR6–8 and SRCR domains (amino acids 124 to 788); Deletion 6 (SEQ ID NO:22), which is missing the LDLR1–5 domain (amino acids 260 to 414); and Deletion 7 (SEQ ID NO:25), which is missing the CRD2 domain (amino acids 450 to 568).

Construction of a Transmembrane-Containing Modified Human Corin Expression Vector Like most trypsin-like serine proteases, corin is synthesized as a zymogen (Yan, W. et al. (1999) supra; Yan, W. et al. (2000) supra). The predicted activation cleavage sequence in corin is between amino acids Arg801 and Ile802. At this time, the physiological activator of corin is unknown. To generate enzymatically active corin, the cell-based assays described herein rely on an unknown serine protease(s) expressed in HL-5 or 293 cells. Another method to generate enzymatically active corin is to introduce an activation cleavage sequence that is specifically recognized by a known serine protease, such as the peptide sequence Asp-Asp-Asp-Asp-Lys (DDDDK), which is recognized by enterokinase (Kitamoto, Y. et al. (1994) supra).

Plasmid constructs expressing transmembrane-containing modified human corin were generated by PCR methodology using a mutagenesis kit (Stratagene) as follows. Using pcDNA4FLCorin as DNA template, the C-terminal region of human corin was amplified by PCR using two sets of primers: (1) forward primer EntPCR1 a (5'-CAACACGT-TCCAGCCTGGACTACGCTC-3'; SEQ ID NO:26) and reverse primer EntPCR1b (5'-CCTCCAAGGATCT-TATCGTCATCGTCCCCACAGTCTTGTTTAGTACA-3'; SEQ ID NO:27), which span human corin amino acids 116 to 791, the enterokinase activation cleavage sequence Asp-Asp-Asp-Asp-Lys (DDDDK), and human corin amino acids 802 to 805, and (2) forward primer EntPCR2a (5'-GGTT-TAAACGGGCCCTTAGTTTAGGAG-3', SEQ ID NO:28) and reverse primer EntPCR2b (5'-GACGATGACGATAA-GATCCTTGGAGGTCGGACGAGTCG-3', SEQ ID NO:29), which span the enterokinase activation sequence and human corin amino acids 802 to 1042. The PCR conditions used were: 95° C.—2 min; 95° C.—30 sec; 56° C.—30 sec; 72° C.—2 min; 30 cycles; and 72° C.—10 min. The PCR product was digested with XhoI and ApaI and inserted into the XhoI and ApaI sites of pcDNA4FLCorin. The resultant plasmid, pcDNA4FLCorin-EK, expresses a recombinant corin polypeptide consisting of human corin amino acids 1 to 123, Leu-Glu, human corin amino acids 124 to 791, Asp-Asp-Asp-Asp-Lys, and human corin amino acids 802 to 1042 (FLCorin-EK, SEQ ID NO:30).

Construction of Soluble Modified Human Corin Expression Vectors

The N-terminal transmembrane domain of type II transmembrane serine proteases is predicted to part of a regulatory mechanism that restricts the activity of the protease to specific locations on the cell surface (Hooper, J. D. et al. (2001) supra). The transmembrane domain, however, does not appear to be required for the enzymatic activity of type II transmembrane serine proteases since recombinant soluble enterokinase (Lu, D. et al. (1997) *J. Biol. Chem.* 272:31293–31300) and matriptase (Lin, C. Y. et al. (1997) *J. Biol. Chem.* 272:9147–9152; Takeuchi, T. et al. (2000) *J. Biol. Chem.* 275:26333–26342) have been shown to be catalytically active.

The predicted N-terminal transmembrane domain of human corin encompasses amino acid residues 46 to 66 (Yan, W. et al. (1999) supra). Therefore, the extracellular domain of human corin encompasses amino acid residues 67 to 1042 in FIG. 2, corresponding to position 199 to 3129 in FIG. 1. Plasmid constructs expressing soluble human corin lacking the transmembrane domain and containing the enterokinase activation cleavage sequence were generated by PCR methodology as follows. Using pcDNA4FLCorin-EK as DNA template, the human corin region lacking the transmembrane domain and containing the enterokinase activation cleavage sequence Asp-Asp-Asp-Asp-Lys was amplified by PCR using forward primer CorFL-1 (5'-GGGGCTCGAGGATGCTTCTCTCCCAGGG-GACCAAAGTCACAGG-3'; SEQ ID NO:31) and reverse primer CorSol2Apa2 (5'-GGGGGGGCCCGTTTAG-GAGAAAGGTCTGGATGTAAATCTG-3', SEQ ID NO:32), which span human corin amino acids 124 to 1024 and the enterokinase activation cleavage sequence. The PCR conditions used were: 95° C.—2 min; 95° C.—30 sec; 56° C.—2 min; 72° C.—3 min; 30 cycles; and 72° C.—15 min. The PCR product was inserted into pSecTag/FRTN5-His-TOPO (Invitrogen). The resultant plasmid expresses a recombinant corin polypeptide, SolCorin-EK (nucleic acid sequence SEQ ID NO:33, amino acid sequence SEQ ID NO:34), consisting of an N-terminal Igκ secretion signal sequence (amino acids 1 to 36), Leu-Glu (amino acids 37 to 38), human corin amino acids 124 to 796 (amino acids 39 to 711), the enterokinase activation cleavage sequence (amino acids 712 to 716), human corin amino acids 802 to 1042 (amino acids 717 to 957) and a C-terminal viral V5 and 6×His epitope tags (amino acids 958 to 991).

The serine protease domain of human corin is amino acids 802 to 1042 (Yan, W. et al. (1999) supra). Plasmid constructs expressing soluble human corin containing the enterokinase activation cleavage sequence and serine protease catalytic domain and were generated by PCR methodology as follows. Using pcDNA3.1 Corin as DNA template, the serine protease domain of human corin was amplified by PCR using two forward primers, SolCat1 (5'-CTGCTGCCGAC-GATGACGATAAGATCCTTGGAGGTCGGACGAGTC G-3', SEQ ID NO:35) and SolCat2 (5'-AAACAAGACT-GTGGGCGCCGCCCTGCTGCCGACGATGACGATAA G-3', SEQ ID NO:36), and reverse primer CorSol2Apa2 (SEQ ID NO:32), which span human corin amino acids 787 to 796, Asp-Asp-Asp-Asp-Lys, and human corin amino acids 802 to 1042. The PCR conditions used were: 95° C.—2 min; 95° C.—30 sec; 58° C.—1 min; 72° C.—1 min; 30 cycles; and 72° C.—15 min. The PCR product was inserted into pSecTag/FRTN5-His-TOPO (Invitrogen). The resultant plasmid expresses a recombinant corin polypeptide, SolCorinPD-EK (amino acid sequence SEQ ID NO:37) consisting of an N-terminal Igκ secretion signal sequence (amino acids 1 to 36), human corin amino acids 787 to 796 (amino acids 37 to 46), the enterokinase activation cleavage sequence (amino acids 47 to 51), human corin amino acids 802 to 1042 (amino acids 52 to 292) and a C-terminal viral V5 and 6×His epitope tags (amino acids 293 to 326).

Figure 7:
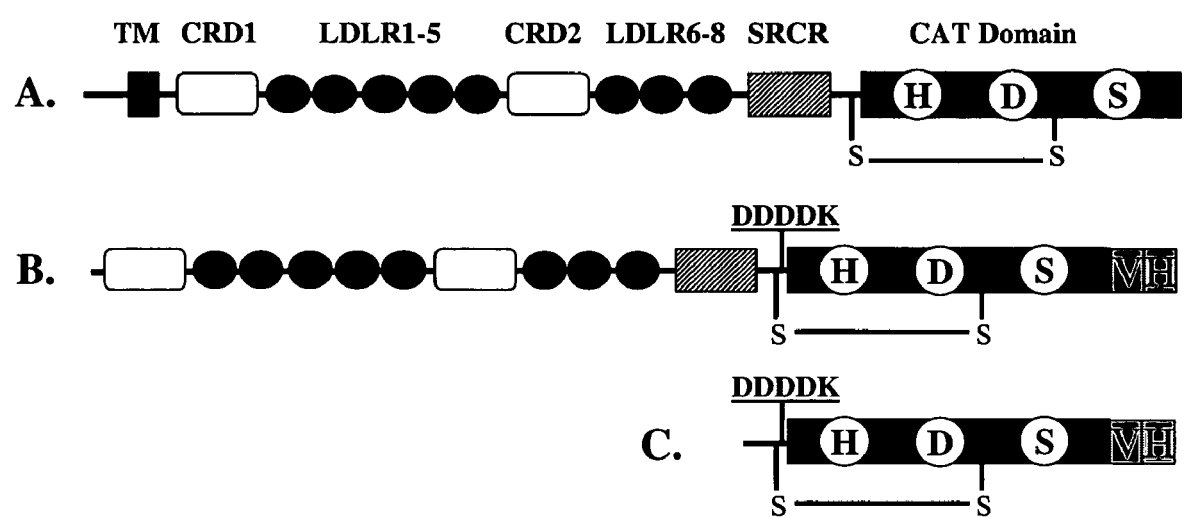
FIG. 7. Schematic structures of soluble modified human corin polypeptides: (A) full-length wild-type human corin; (B) SolCorin-EK, which lacks the transmembrane domain; and (C) SolCorinPD-EK, which contains only the serine protease catalytic domain. The enterokinase activation cleavage sequence DDDDK (SEQ ID NO:44) was introduced in place of the natural corin activation cleavage sequence in SolCorin-EK and SolCorinPD-EK, as described in Example 1.
Figure 11:
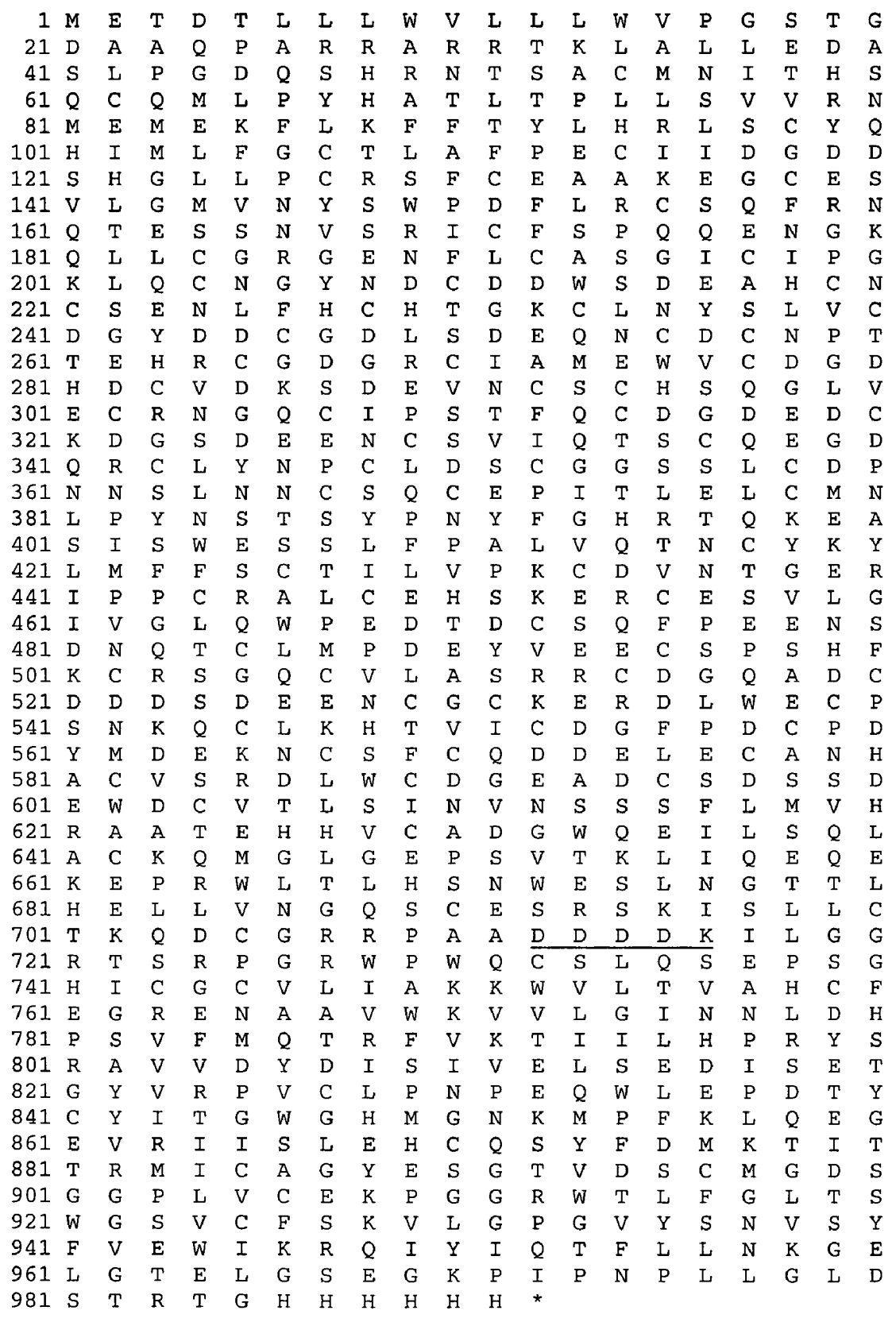

The schematic structures of SolCorin-EK and SolCorinPD-EK are depicted in FIG. 7. The nucleic acid and amino acid sequences of SolCorin-EK (SEQ ID NOS:33 and 34) are shown in FIGS. 10 and 11, respectively.

EXAMPLE 2

Construction of Pro-ANP and Pro-BNP Expression Vectors

To examine processing of pro-peptides by corin in vitro, mammalian expression vectors encoding human pro-ANP and pro-BNP were constructed.

Plasmid constructs expressing either human wild-type pro-ANP or human wild-type pro-BNP were generated as described (Yan, W. et al. (2000) supra). The coding regions of human pro-ANP (Oikawa, S. et al. (1984) *Nature* 309: 724–726) and human pro-BNP (Sudoh, T. et al. (1989) *Biochem. Biophys. Res. Commun.* 159:1427–1434) were amplified by PCR from a human heart cDNA library and inserted individually into pcDNA3.1N5-His-TOPO (Invitrogen). The recombinant pro-ANP and pro-BNP generated using this expression vector contain C-terminal viral V5 and 6×His epitope tags, thereby facilitating detection of the recombinant proteins by anti-V5 and anti-His antibodies. The resultant plasmids were confirmed by restriction enzyme digestion and by DNA sequencing.

EXAMPLE 3

Processing of Pro-Peptides by Corin In Vitro

To examine processing of pro-peptides by corin in vitro, mammalian cells in culture are co-transfected with a corin expression vector and a pro-peptide expression vector. Cleavage of the pro-peptide is analyzed by Western blotting using antibodies against peptide tags attached to the recombinant corin or pro-peptide.

Cell Culture

Murine HL-5 cardiac myocyte cells were cultured in Ex-Cell 320 medium (JRH Biosciences) containing 10% FBS, 15 µg/ml insulin, 50 µg/ml endothelial growth supplement (Upstate Biotechnology Institute), 1 µM retinoic acid, 0.1 mM norepinephrine, 100 µg/ml penicillin/streptomycin, 292 µg/ml L-glutamine, and 0.1 mM MEM non-essential amino acids. Human 293 cells were cultured in α-MEM (Life Technologies, Inc.) supplemented with 10% FBS and 1% L-glutamine. Baby hamster kidney (BHK) cells were cultured in EMEM (Life Technologies, Inc.) supplemented with 10% FBS. All cells were cultured at 37° C. in humidified incubators with 5% $CO_2$ and 95% air.

Transfection and Western Blot Analysis

Figure 4:
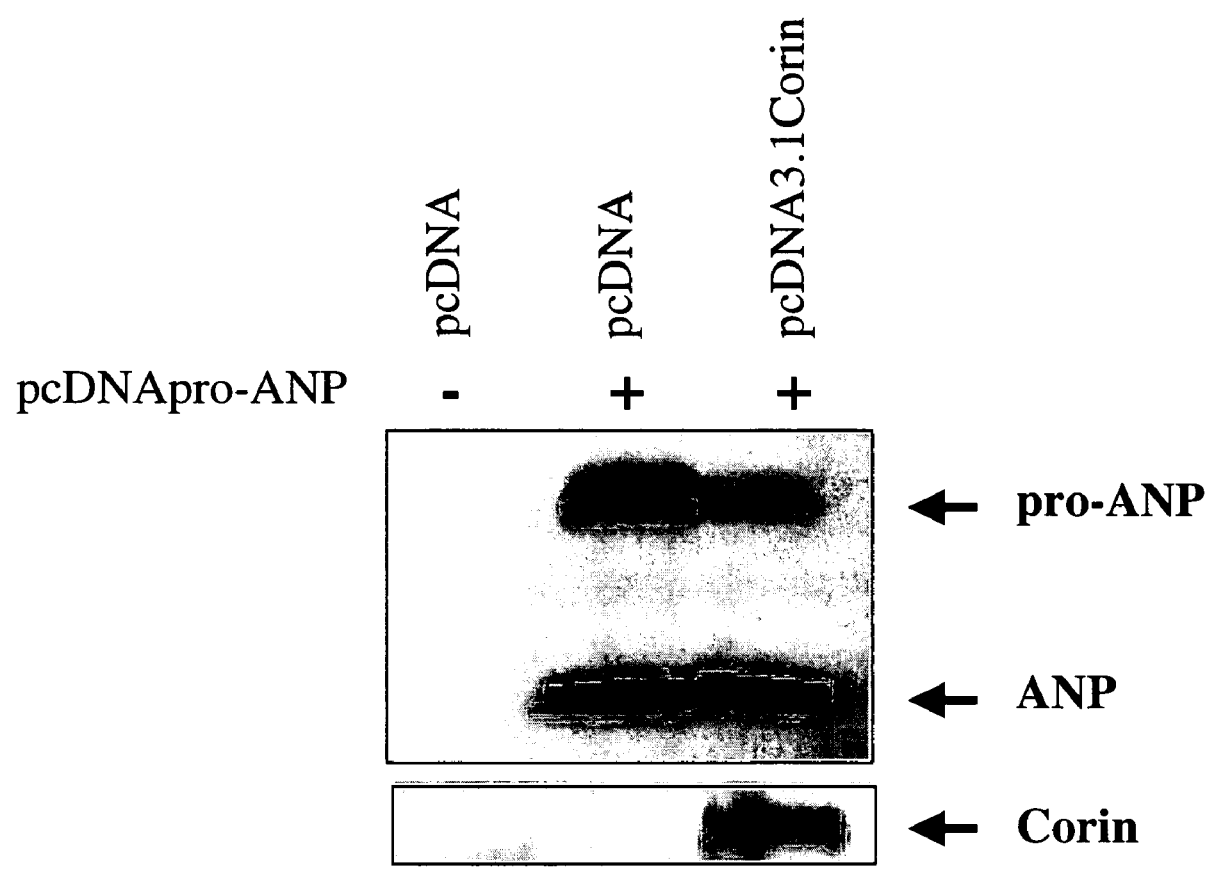
FIG. 4. Processing of recombinant pro-ANP in murine HL-5 cells expressing human corin. Murine HL-5 cells were transfected with the indicated control, pro-ANP, or full-length human corin expression plasmids as described in Example 3. Pro-ANP, ANP, and corin were detected in conditioned medium by Western blotting using an anti-V5 antibody.

Transient transfection was performed in HL-5 cells using Lipofectin (Invitrogen) according to the manufacturer's instructions. Transient or stable transfection was performed in 293 cells using Lipofectin 2000 (Life Technologies, Inc.)

according to the manufacturer's instructions. The control expression vector (pcDNA) or recombinant corin expression vector (pcDNA3.1Corin) was co-transfected with the recombinant pro-ANP expression vector (pcDNApro-ANP). Conditioned medium was collected 48 or 72 hours after transfection. To analyze pro-ANP processing, recombinant pro-ANP and its derivatives, as well as recombinant corin, in the conditioned medium were immunoprecipitated by an anti-V5 antibody (Invitrogen). Proteins were separated by SDS-PAGE and analyzed by Western blotting using a horseradish peroxidase-conjugated anti-V5 antibody (Invitrogen). As shown in FIG. 4, processing of pro-ANP was detected in HL-5 cells transfected with only the pro-ANP expression vector. However, the expression of recombinant corin further enhanced the processing of pro-ANP in HL-5 cells.

cGMP Assay

Figure 5:
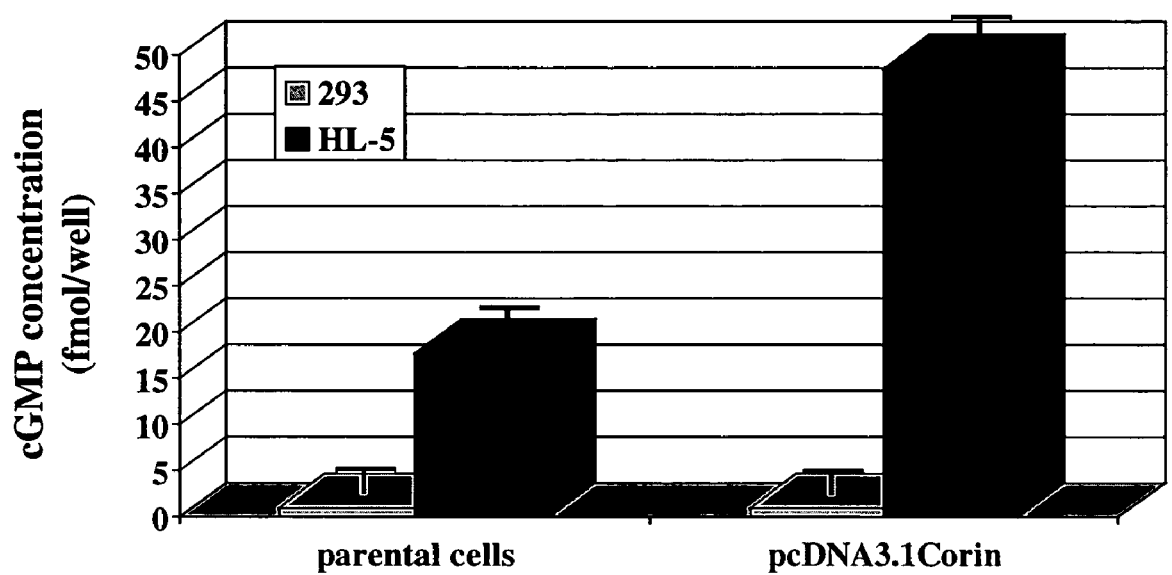
FIG. 5. Stimulation of intracellular cGMP production by conditioned media from murine HL-5 cells expressing human corin. Human 293 cells and murine HL-5 cells were transfected with the full-length human corin expression plasmid, and cGMP-stimulating activity in conditioned medium was measured, as described in Example 3. cGMP-stimulating activity in HL-5 cells was significantly increased by expression of recombinant human corin.

To examine the activity of processed recombinant ANP, a cGMP assay was performed using an enzyme immunoassay (EIA) kit (Biotrak, Amersham Biosciences, Inc.). In this assay, baby hamster kidney (BHK) cells were grown in 96-well plates in MEM medium supplemented with 10% FBS and 1% L-glutamine. Confluent cells were washed once with serum-free medium. Conditioned medium (180 µl) containing recombinant pro-ANP and its derivatives from transfected human 293 cells or murine HL-5 cells was added to each well and incubated at 37° C. for 10 min. The cells were lysed by addition of 20 µl lysis buffer containing 2% dodecyl timethylammonium and 50 mM sodium acetate, pH 5.8. The intracellular cGMP concentration in the ANP-stimulated BHK cells was determined with the Biotrak EIA kit. Each experimental condition was assayed in quadruplicate. As shown in FIG. 5, conditioned medium from 293 cells, untransfected or transfected with the full-length human corin expression vector, does not increase cGMP levels in BHK cells. The conditioned medium from untransfected HL-5 cells stimulates intracellular cGMP production; this production is enhanced by using conditioned medium from HL-5 cells transfected with the full-length human corin expression vector.

EXAMPLE 4

Processing of Pro-ANP by Corin Internal Deletion Mutants In Vitro

To examine the requirement for various domains of human corin for processing of pro-peptides in vitro, mammalian cells in culture are co-transfected with the full-length human corin expression vector or a series of human corin internal deletion mutant expression vectors (see Example 1), together with a pro-peptide expression vector. Cleavage of the pro-peptide is analyzed by Western blotting using antibodies against the tags attached to the recombinant corin and pro-peptide.

Figure 6:
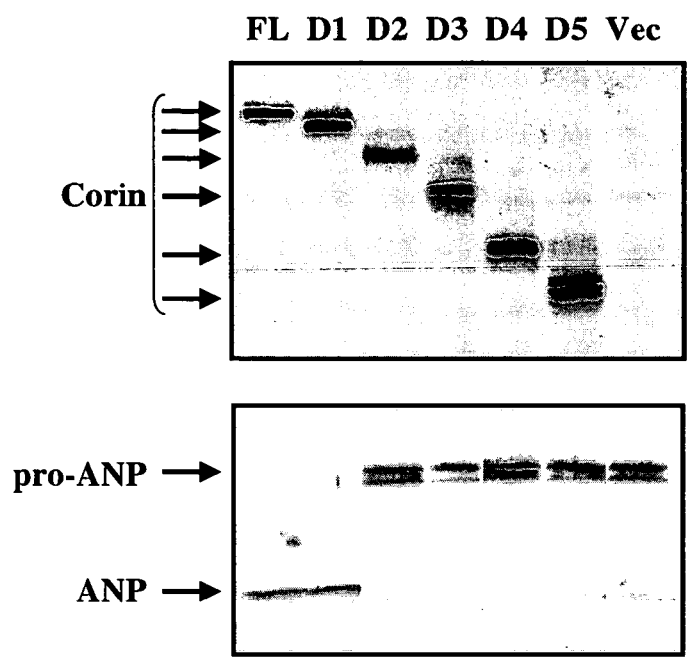
FIG. 6. Processing of pro-ANP by transmembrane-containing modified human corin deletion mutants. The full-length human corin expression vector and a series of human corin internal deletion mutant expression vectors, together with a pro-ANP expression vector, were transfected into human 293 cells. Corin, pro-ANP, and ANP were detected in conditioned medium by Western blotting using an anti-V5 antibody.

Human 293 cells were co-transfected with pcDNApro-ANP and plasmids expressing the full-length human corin and various human corin internal deletion mutants using Lipofectamine 2000 according to the manufacturer's instructions. After 24 hrs, conditioned medium containing recombinant human pro-ANP and its derivatives was collected, and processing of pro-ANP was analyzed by immunoprecipitation using an anti-V5 antibody followed by SDS-PAGE and Western blotting using an HRP-conjugated anti-V5 antibody. FIG. 6 shows that the full-length human corin polypeptide and Deletion 1, which is missing the CRD1 domain, were able to process pro-ANP, whereas Deletions 2 to 5 were inactive in this assay. Deletions 6 and 7 were also inactive in this assay (data not shown). Western blotting of cell extracts prepared from the transfected 293 cells confirmed that all of the internal deletion mutant constructs expressed corin polypeptides of the expected size (FIG. 6 and data not shown).

EXAMPLE 5

Processing of Modified Corin by Enterokinase In Vitro

To examine processing of modified corin by enterokinase in vitro, mammalian cells in culture are co-transfected with a corin expression vector. Cleavage of corin is analyzed by Western blotting using antibodies against peptide tags attached to the recombinant corin.

Cell Culture and Transfection

Human 293 cells were cultured in A-MEM (Life Technologies, Inc.) supplemented with 10% FBS and 1% L-glutamine. Transient or stable transfection was performed in 293 cells using Lipofectin 2000 (Life Technologies, Inc.) according to the manufacturer's instructions.

Activation of Modified Corin by Enterokinase

Figure 8:
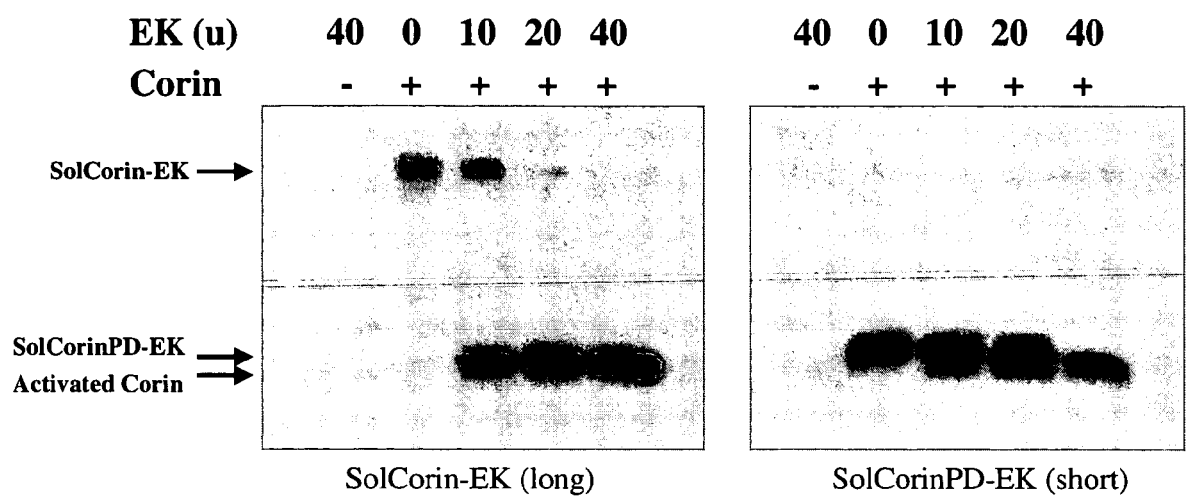
FIG. 8. Activation of soluble modified human corin by enterokinase. SolCorin-EK or SolCorinPD-EK expression vectors were transfected into human 293 cells as indicated. The conditioned medium was treated with the indicated amounts of recombinant enterokinase, and activation of soluble corin was detected by Western blotting using an anti-V5 antibody.

Recombinant SolCorin-EK or SolCorinPD-EK was expressed in stably transfected human 293 cells. Conditioned medium (0.5 ml) containing SolCorin-EK or SolCorinPD-EK was collected and incubated with 0, 2, 10, 20 or 40 units of purified enterokinase (Calbiochem) at 25° C. for 4 hrs. To analyze the activation of corin, 20 µl of samples were used for SDS-PAGE followed by Western blotting using an anti-V5 antibody (Invitrogen). As shown in FIG. 8, both the long form (SolCorin-EK) and short form (SolCorinPD-EK) of soluble modified human corin were cleaved by exposure to enterokinase in a dose-dependent manner.

Activation of Human Pro-ANP by Enterokinase Activated Modified Corin

Recombinant human pro-ANP was transiently transfected into human 293 cells using Lipofectamine 2000 (Life Technologies, Inc.) according to the manufacturer's instructions. Pro-ANP-containing conditioned medium was collected 24 hrs later and placed on ice for later use. The activation of SolCorin-EK or SolCorinPD-EK in the conditioned medium from stably transfected human 293 cells was performed as described above. To remove the enterokinase, an Enterokinase Cleavage Capture Kit was used (Calbiochem). Each sample of conditioned medium was incubated with 100 µl of EKapture agarose beads at 25° C. for 30 min, and filtered through spin filters. Control OPTI-MEM (Life Technologies, Inc.) or the enterokinase-depleted conditioned medium (250 µl) was incubated with 1 ml of the pro-ANP containing conditioned medium at 4° C. for 3 hours. Processing of pro-ANP was analyzed by immunoprecipitation using an anti-V5 antibody and followed by SDS-PAGE and Western blotting using a horseradish peroxidase-conjugated anti-V5 antibody. Recombinant corin is also recognized by the anti-V5 antibody in Western blots because it contains the C-terminal viral V5 epitope tag. As shown in FIG. 9, pro-ANP was processed to ANP by the long form (SolCorin-EK), but not the short form (SolCorin-PD-EK), of soluble modified human corin upon activation by enterokinase in vitro.

EXAMPLE 6

Activity of Soluble Modified Human Corin In Vivo

To examine the activity of soluble modified human corin in vivo, recombinant SolCorin-EK was expressed in mammalian cells, purified, activated by enterokinase, and then tested for its ability to stimulate diuresis and natriuresis in hamsters.

Purification of Recombinant SolCorin-EK or SolCorinPD-EK

Recombinant SolCorin-EK was expressed in stably transfected human 293 cells (see Example 5). Conditioned medium from SolCorin-EK expressing cells was filtered through an Opticab 4 capsule disposable cartridge filter (Millipore), concentrated ~10-fold, and diafiltered in 20 mM Tris-HCl, pH 7.5, 300 mM NaCl. Lipids were then removed by filtration through a Zeta PlusBioCap filter (Cuno).

Concentrated and diafiltered conditioned medium containing SolCorin-EK was adjusted to 10 mM imidazole, then filtered through a 0.45 μm cellulose acetate filter and loaded onto a Ni-NTA-Superflow (Qiagen) column equilibrated in 20 mM Tris-HCl, pH 7.5, 300 mM NaCl. The column was washed in 20 mM Tris-HCl, pH 7.5, 300 mM NaCl, 20 mM imidazole, and protein was eluted from the column in 20 mM Tris-HCl, pH 7.5, 300 mM NaCl with a gradient from 20 mM to 250 mM imidazole.

Ni-NTA eluate containing SolCorin-EK was loaded onto a Poros 50 polyethyleneimine (PI) (Perseptive Biosystems) anion exchange column equilibrated in 20 mM Tris-HCl, pH 7.5. The column was washed to remove aggregated protein in 20 mM Tris-HCl, pH 7.5, 300 mM NaCl, and protein was eluted from the column in 20 mM Tris-HCl, pH 7.5, with a gradient from 300 mM to 1 M NaCl.

The PI eluate containing SolCorin-EK was diluted to ~50 mM NaCl, concentrated by ultrafiltration with a 10 kDa cut-off (Millipore), and loaded onto a DEAE-Sepharose Fast Flow (Pharmacia) anion exchange column equilibrated in 20 mM Tris-HCl, pH 7.5. The column was washed in 20 mM Tris-HCl, pH 7.5, and protein was eluted from the column in 20 mM Tris-HCl, 1 M NaCl. The eluate containing SolCorin-EK was diluted 1:2 with 20 mM Tris-HCl, pH 7.5.

The purity of the SolCorin-EK preparation was determined to be ~94%, as judged by analytical size exclusion chromatography. The size and integrity of SolCorin-EK was confirmed by SDS-polyacrylamide gel chromatography followed by Coomassie Blue staining.

Activation of SolCorin-EK by Enterokinase

Purified SolCorin-EK was activated by exposure to recombinant enterokinase (Novagen) at a ratio of 1 unit enterokinase per 50 μg protein in 20 mM Tris-HCl, pH 7.5, ~260 mM NaCl, 2 mM CaCl$_2$ for 4 hours at room temperature. Aggregated protein was removed by centrifugation for 10 minutes at 10,000 rpm in an Eppendorf microfuge. The activated Sol-Corin-EK was separated into 1 mg aliquots, rapidly frozen in a dry ice/ethanol bath, and then stored at −80° C.

Effect of SolCorin-EK on Diuresis and Natriuresis in Cardiomyopathic Hamsters

The BIO14.6 cardiomyopathic (CM) hamster, an autosomal recessive strain, has a mutation in the δ-sarcoglycan gene (Nigro, V. et al. (1997) *Hum. Mol. Genet.* 6:601–607). The BIO14.6 hamster develops severe cardiomyopathy with hypertrophic features and heart failure, but manifests a comparatively mild skeletal muscle phenotype. Studies have shown that BIO 14.6 CM hamsters are deficient in ANP activity, as judged by reduced diuresis and natriuresis, however, the production, release and/or activation of ANP can be induced (Dlouha, H. and McBroom, M. J. (1986) *Proc. Soc. Exp. Biol. Med.* 181:411–415).

Normal (F1B) and BIO 14.6 CM hamsters were prepared as follows. Under isoflurane (1–2%) anesthesia, the bladder and the right jugular vein were cannulated for urine collection and drug administration, respectively. When blood pressure measurement was required, a transducer pressure was inserted into the left carotid artery. After a ~30 minute period, which covers the time required for surgery, a 5% glucose solution infusion was initiated at 35 μl/min and urine was collected for 10 minute periods, both continuing throughout the experiment. After urine output stabilized (~1 hour after starting the glucose infusion), rat ANP, SolCorin-EK, or Vehicle was intravenously adminstered to the hamsters as a bolus injection into the jugular vein. A 1 mg/ml stock solution of rat ANP (Sigma) was diluted in 0.9% NaCl, and administered in a fixed 100 μl volume to F1B hamsters at doses of 1, 3, 10, and 30 μg/kg, and to BIO 14.6 CM hamsters at 10, 30, and 100 μg/kg. A stock solution of SolCorin-EK, either 1.27 or 1.39 mg/ml, in 20 mM Tris-HCl, pH 7.5, ~260 mM NaCl, 2 mM CaCl$_2$, 45.9 units/ml enterokinase, was administered at 3 mg/kg in a volume of ~300 μl per animal, varying according to solution concentration and body weight. Vehicle (20 mM Tris-HCl, pH 7.5, 260 mM NaCl, 2 mM CaCl$_2$, 45.9 units/ml enterokinase) was administered in a volume of ~300 μl per animal, varying according to body weight.

Figure 12:
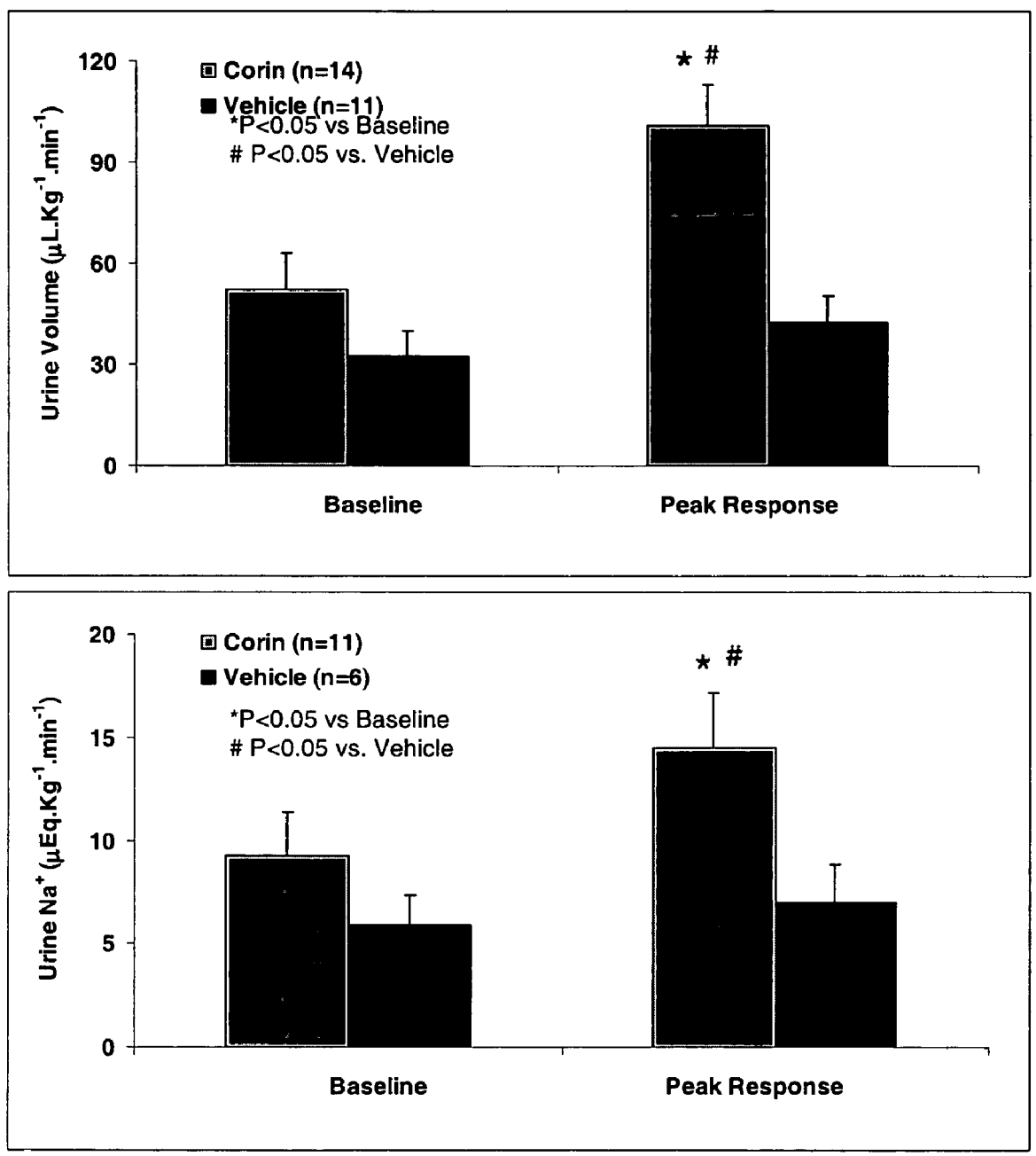
FIG. 12. Soluble modified human corin stimulates diuresis and natriuresis in cardiomyopathic hamsters. SolCorin-EK was expressed in human 293 cells, purified, activated by exposure to recombinant enterokinase, and tested for the ability to elevate urine volume and urine sodium in BIO 14.6 CM hamsters, as described in Example 6. Urine volume and urine sodium was measured before (Baseline) and after (Peak Response) intravenous administration of SolCorin-EK (Corin) or Vehicle as indicated.

Diuresis and natriuresis in hamsters were measured by calculating the urine volume and urine sodium, respectively. Urine volume, expressed as $\mu l.kg^{-1}.min^{-1}$, and urine sodium ($Na^+$), expressed as $\mu Eq.kg^{-1}.min^{-1}$, were calculated from the 10 minute period urine pools directly before (Baseline) and directly after (Peak Response) intravenous administration of either ANP, SolCorin-EK, or Vehicle. In control experiments using BIO 14.6 CM hamsters (not shown), rat ANP increased urine volume and urine sodium excretion in the first 10 minutes, the peak response. As shown in FIG. 12, SolCorin-EK elevated the peak response of both urine volume and urine sodium in BIO 14.6 CM hamsters. This elevation was statistically significant ($p<0.05$) compared to the baseline in corin-treated animals and to the peak response in vehicle-treated animals. Therefore, soluble modified human corin is able to induce ANP activity in cardiomyopathic hamsters in vivo.

EXAMPLE 7

This example illustrates the preparation of representative pharmaceutical compositions for oral administration containing a modified corin molecule of the invention, or a pharmaceutically acceptable salt thereof:

| A. | Ingredients | % wt./wt. |
|---|---|---|
| | Modified corin molecule of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Modified corin molecule of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Modified corin molecule of the invention | 0.1 g |
| | Propylene glycol | 20.0 g |
| | Polyethylene glycol 400 | 20.0 g |
| | Polysorbate 80 | 1.0 g |
| | Water | q.s. 100 ml |

The modified corin molecule of the invention is dissolved in propylene glycol, polyethylene glycol 400 and polysorbate 80. A sufficient quantity of water is then added with stirring to provide 100 ml of the solution, which is filtered and bottled.

| D. | Ingredients | % wt./wt. |
|---|---|---|
| | Modified corin molecule of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Modified corin molecule of the invention | 1.0% |
| | Methyl or carboxymethyl cellulose | 2.0% |
| | 0.9% saline | q.s. 100 ml |

The modified corin molecule of the invention is dissolved in the cellulose/saline solution, filtered and bottled for use.

EXAMPLE 8

This example illustrates the preparation of a representative pharmaceutical formulation for parenteral administration containing a modified corin molecule of the invention, or a pharmaceutically acceptable salt thereof:

| Ingredients | |
|---|---|
| Modified corin molecule of the invention | 0.02 g |
| Propylene glycol | 20.0 g |
| Polyethylene glycol 400 | 20.0 g |

-continued

| Ingredients | |
|---|---|
| Polysorbate 80 | 1.0 g |
| 0.9% Saline solution | q.s. 100 ml |

The modified corin molecule of the invention is dissolved in propylene glycol, polyethylene glycol 400 and polysorbate 80. A sufficient quantity of 0.9% saline solution is then added with stirring to provide 100 ml of the I.V. solution, which is filtered through a 0.2 μm membrane filter and packaged under sterile conditions.

EXAMPLE 9

This example illustrates the preparation of a representative pharmaceutical composition in suppository form containing a modified corin molecule of the invention, or a pharmaceutically acceptable salt thereof:

| Ingredients | % wt./wt. |
|---|---|
| Modified corin molecule of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 10

This example illustrates the preparation of a representative pharmaceutical formulation for insufflation containing a modified corin molecule of the invention, or a pharmaceutically acceptable salt thereof:

| Ingredients | % wt./wt. |
|---|---|
| Micronized modified corin molecule of the invention | 1.0% |
| Micronized lactose | 99.0% |

The ingredients are milled, mixed, and packaged in an insufflator equipped with a dosing pump.

EXAMPLE 11

This example illustrates the preparation of a representative pharmaceutical formulation in nebulized form containing a modified corin molecule of the invention, or a pharmaceutically acceptable salt thereof:

| Ingredients | % wt./wt. |
|---|---|
| Modified corin molecule of the invention | 0.005% |
| Water | 89.995% |
| Ethanol | 10.000% |

The modified corin molecule of the invention is dissolved in ethanol and blended with water. The formulation is then packaged in a nebulizer equipped with a dosing pump.

EXAMPLE 12

This example illustrates the preparation of a representative pharmaceutical formulation in aerosol form containing a modified corin molecule of the invention, or a pharmaceutically acceptable salt thereof:

| Ingredients | % wt./wt. |
| --- | --- |
| Modified corin molecule of the invention | 0.10% |
| Propellant 11/12 | 98.90% |
| Oleic acid | 1.00% |

The modified corin molecule of the invention is dispersed in oleic acid and the propellants. The resulting mixture is then poured into an aerosol container fitted with a metering valve.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An modified corin molecule, comprising a serine protease catalytic domain encoded by a nucleic acid sequence that hybridizes to the complementary strand of a nucleic acid molecule consisting of nucleotides 2404 to 3126 of SEQ ID NO:1 at 42° C. in 50% (vol/vol) formamide, 5×SSC (0.75M NaCl, 0.075 M sodium citrate). 50 mM sodium phosphate (pH 6.8), 0.1% sodium pyrophosphate, 5× Denhardt's solution, sonicated salmon sperm DNA (50 mg/ml), 0.1% SDS, and 10% dextran sulfate followed by washes at 42° C. in 0.2×SSC 0.1% SDS, wherein the modification is the substitution of the activation sequence at positions corresponding to positions 801 through 805 of SEQ ID NO:2 with another activation sequence selected from the group consisting of LKTPRVVGG (SEQ ID NO:38), TRQARVVGG (SEQ ID NO:39), DDDDKIVGG (SEQ ID NO:40), and DDDDKILGG (SEQ ID NO:43), and wherein said modified corin molecule, when activated, is capable of cleaving a pro-atrial natrurietic factor to produce an atrial natrurietic factor.

2. A modified corin molecule comprising the serine protease catalytic domain having the amino acid sequence from position 802 to position 1042 of SEQ ID NO:2 wherein the modification is the substitution of the activation sequence at positions 801 through 805 of SEQ ID NO:2 with another activation sequence selected from the group consisting of LKTPRVVGG (SEQ ID NO:38), TRQARVVGG (SEQ ID NO:39), DDDDKIVGG (SEQ ID NO:40), and DDDDKILGG (SEQ ID NO:43), and wherein said molecule, when activated, is capable of cleaving a pro-atrial natrurietic factor to produce an atrial natrurietic factor.

3. The modified corin molecule of claim 1, wherein said corin molecule further comprises at least one additional domain selected from the group consisting of the cysteine-rich domain 1 (CRD1) from position 134 through position 259 of SEQ ID NO:2, the low-density lipoprotein receptor repeats 1–5 (LDLR1–5) from position 268 through position 415 of SEQ ID NO:2 the cysteine-rich domain 2 (CRD2) from position 450 through position 573 of SEQ ID NO:2 the low-density lipoprotein receptor repeats 6–8 (LDLR6–8) from position 579 through position 690 of SEQ ID NO:2, and the a macrophage scavenger receptor-like domain (SRCR) from position 713 through position 800 of SEQ ID NO:2.

4. The modified corin molecule of claim 3 that, comprises a serine protease catalytic domain, the low-density lipoprotein receptor repeats 1–5 (LDLR1–5) from position 268 through position 415 of SEQ ID NO:2, cysteine-rich domain 2 (CRD2) from position 450 through position 573 of SEQ ID NO:2 the low-density lipoprotein receptor repeats 6–8 (LDLR 6–8) from position 579 through position 690 of SEQ ID NO:2, and the macrophage scavenger receptor-like (SRCR) domain from position 713 through position 800 of SEQ ID NO:2.

5. The modified corin molecule of claim 1, wherein the substitute activation sequence is DDDDKILGG (SEQ ID NO: 43).

6. A modified corin molecule comprising the extracellular domain of corin, wherein said extracellular domain comprises the low-density lipoprotein receptor repeats 1–5 (LDLR1–5) from position 268 through position 415 of SEQ ID NO:2, cysteine-rich domain 2 (CRD2) from position 450 through position 573 of SEQ ID NO:2, low-density lipoprotein receptor repeats 6–8 (LDLR6–8) from position 579 through position 690 of SEQ ID NO:2, the macrophage scavenger receptor-like domain (SRCR) from position 713 through position 800 of SEQ ID NO:2, the serine protease catalytic domain from position 802 to position 1042 of SEQ ID NO:2, wherein the modification is the substitution of the activation sequence at positions 801 through 805 of SEQ ID NO:2 with the activation sequence DDDDKILGG (SEQ ID NO:43).

7. The modified corin molecule of claim 6 that comprises the amino acid sequence of SEQ ID NO:34.

8. The modified corin molecule of claim 1, wherein the substitute activation sequence is recognized and cleaved by thrombin, trypsin, human airway trypsin-like protease (HAT), mast cell tryptase, mannose-binding lectin-associated serine protease 1 (MASP-1), mannose-binding lectin-associated serine protease 2 (MASP-2), matriptase (MT-SP1), transmembrane protease, serine 2 (TMPRSS2), or epitheliasin.

9. The modified corin molecule of claim 1, further comprising a signal peptide sequence.

10. The modified corin molecule of claim 9, wherein the signal peptide sequence is bacterial, fungal, insect, plant, or animal.

11. The modified corin molecule of claim 9, wherein the signal peptide is an IgK signal sequence.

12. The modified corin molecule of claim 1, further comprising an epitope tag.

13. The modified corin molecule of claim 12, wherein the epitope tag is an amino acid tag.

14. The modified corin molecule of claim 12, wherein the epitope tag is histidine (6×His) or cysteine.

15. The modified corin molecule of claim 12, wherein the epitope tag is V5 or flag.

16. The modified corin molecule of claim 1, wherein the serine protease catalytic domain is mammalian.

17. The modified corin molecule of claim 16, wherein the mammal is bovine, porcine, murine, equine, canine, feline, ovine, simian, or human.

18. A pharmaceutical composition, comprising the modified corin molecule of claim 1, which composition comprises a pharmaceutically acceptable excipient and a therapeutically effective amount of said modified corin molecule.

19. The pharmaceutical composition of claim 18, wherein said pharmaceutical excipient is selected from a group consisting of a phosphate buffered saline solution, water, emulsions, oil/water emulsion, wetting agents, sterile solutions, excipients, starch, milk, sugar, clay, gelatin, stearic acid, salts of stearic acid, magnesium stearate, calcium stearate, talc, vegetable fats or oils, gums, and glycols.

20. The pharmaceutical composition of claim 19, which is formulated as a liposome, polymeric composition, or polymer microsphere.

21. The pharmaceutical composition of claim 19, which is formulated as a tablet, coated tablet, or capsule.

22. A kit, comprising the isolated molecule of claim 1.

* * * * *

SEQUENCE LISTING

<160> NUMBER OF SEQ ID NOS: 41

<210> SEQ ID NO 1
<211> LENGTH: 3129
<212> TYPE: DNA
<213> ORGANISM: Homo sapiens

<400> SEQUENCE: 1

```
atgaaacagt ctcctgccct cgctccggaa gagcgctacc gcagagccgg gtccccaaag      60
ccggtcttga gagctgatga caataacatg ggcaatggct gctctcagaa gctggcgact     120
gctaacctcc tccggttcct attgctggtc ctgattccat gtatctgtgc tctcgttctc     180
ttgctggtga tcctgctttc ctatgttgga acattacaaa aggtctattt taaatcaaat     240
gggagtgaac ctttggtcac tgatggtgaa atccaagggt ccgatgttat tcttacaaat     300
acaatttata accagagcac tgtggtgtct actgcacatc ccgaccaaca cgttccagcc     360
tggactacgg atgcttctct cccaggggac caaagtcaca ggaatacaag tgcctgtatg     420
aacatcaccc acagccagtg tcagatgctg ccctaccacg ccacgctgac acctctcctc     480
tcagttgtca gaaacatgga aatggaaaag ttcctcaagt ttttcacata tctccatcgc     540
ctcagttgct atcaacatat catgctgttt ggctgtaccc tcgccttccc tgagtgcatc     600
attgatggcg atgacagtca tggactcctg ccctgtaggt ccttctgtga ggctgcaaaa     660
gaaggctgtg aatcagtcct ggggatggtg aattactcct ggccggattt cctcagatgc     720
tcccagttta gaaaccaaac tgaaagcagc aatgtcagca gaatttgctt ctcacctcag     780
caggaaaacg gaaagcaatt gctctgtgga aggggtgaga actttctgtg tgccagtgga     840
atctgcatcc ccgggaaact gcaatgtaat ggctacaacg actgtgacga ctggagtgac     900
gaggctcatt gcaactgcag cgagaatctg tttcactgtc acacaggcaa gtgccttaat     960
tacagccttg tgtgtgatgg atatgatgac tgtgggggatt tgagtgatga gcaaaactgt    1020
gattgcaatc ccacaacaga gcatcgctgc ggggacgggc gctgcatcgc catggagtgg    1080
gtgtgtgatg gtgaccacga ctgtgtggat aagtccgacg aggtcaactg ctcctgtcac    1140
agccagggtc tggtggaatg cagaaatgga caatgtatcc ccagcacgtt tcaatgtgat    1200
ggtgacgagg actgcaagga tgggagtgat gaggagaact gcagcgtcat tcagacttca    1260
tgtcaagaag agaccaaag atgcctctac aatccctgcc ttgattcatg tggtggtagc    1320
tctctctgtg acccgaacaa cagtctgaat aactgtagtc aatgtgaacc aattacattg    1380
```

-continued

```
gaactctgca tgaatttgcc ctacaacagt acaagttatc caaattattt tggccacagg   1440
actcaaaagg aagcatccat cagctgggag tcttctcttt tccctgcact tgttcaaacc   1500
aactgttata ataccctcat gttctttcct tgcaccattt tggtaccaaa atgtgatgtg   1560
aatacaggcg agcgtatccc tccttgcagg gcattgtgtg aacactctaa agaacgctgt   1620
gagtctgttc ttgggattgt gggcctacag tggcctgaag acacagattg cagtcaattt   1680
ccagaggaaa attcagacaa tcaaacctgc ctgatgcctg atgaatatgt ggaagaatgc   1740
tcacctagtc atttcaagtg ccgctcagga cagtgtgttc tggcttccag aagatgtgat   1800
ggccaggccg actgtgacga tgacagtgat gaggaaaact gtggttgtaa agagagagat   1860
ctttgggaat gtccatccaa taaacaatgt ttgaagcaca cagtgatctg cgatgggttc   1920
ccagactgcc ctgattacat ggacgagaaa aactgctcat tttgccaaga tgatgagctg   1980
gaatgtgcaa ccatgcgtg tgtgtcacgt gacctgtggt gtgatggtga agccgactgc   2040
tcagacagtt cagatgaatg ggactgtgtg accctctcta taaatgtgaa ctcctcttcc   2100
tttctgatgg ttcacagagc tgccacagaa caccatgtgt gtgcagatgg ctggcaggag   2160
atattgagtc agctggcctg caagcagatg ggtttaggag aaccatctgt gaccaaattg   2220
atacaggaac aggagaaaga gccgcggtgg ctgacattac actccaactg ggagagcctc   2280
aatgggacca ctttacatga acttctagta aatgggcagt cttgtgagag cagaagtaaa   2340
atttctcttc tgtgtactaa acaagactgt gggcgccgcc ctgctgcccg aatgaacaaa   2400
aggatccttg gaggtcggac gagtcgccct ggaaggtggc catggcagtg ttctctgcag   2460
agtgaaccca gtggacatat ctgtggctgt gtcctcattg ccaagaagtg ggttctgaca   2520
gttgcccact gcttcgaggg gagagagaat gctgcagttt ggaaagtggt gcttggcatc   2580
aacaatctag accatccatc agtgttcatg cagacacgct tgtgaagac catcatcctg   2640 catccccgct acagtcgagc agtggtggac tatgacatca gcatcgttga gctgagtgaa   2700
gacatcagtg agactggcta cgtccggcct gtctgcttgc ccaacccgga gcagtggcta   2760
gagcctgaca cgtactgcta tatcacaggc tggggccaca tgggcaataa aatgccattt   2820
aagctgcaag agggagaggt ccgcattatt tctctggaac attgtcagtc ctactttgac   2880
atgaagacca tcaccactcg gatgatatgt gctggctatg agtctggcac agttgattca   2940
tgcatgggtg acagcggtgg gcctcttgtt tgtgagaagc ctggaggacg gtggacatta   3000
tttggattaa cttcatgggg ctccgtctgc ttttccaaag tcctgggcc tggcgtttat   3060 agtaatgtgt catatttcgt cgaatggatt aaaagacaga tttacatcca gacctttctc   3120
ctaaactaa                                                          3129
```

<210> SEQ ID NO 2
<211> LENGTH: 1042
<212> TYPE: PRT
<213> ORGANISM: Homo sapiens

<400> SEQUENCE: 2

```
Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Leu Val Ile
```

-continued

```
                50                  55                  60
Leu Leu Ser Tyr Val Gly Thr Leu Gln Lys Val Tyr Phe Lys Ser Asn
 65                  70                  75                  80

Gly Ser Glu Pro Leu Val Thr Asp Gly Glu Ile Gln Gly Ser Asp Val
                 85                  90                  95

Ile Leu Thr Asn Thr Ile Tyr Asn Gln Ser Thr Val Val Ser Thr Ala
                100                 105                 110

His Pro Asp Gln His Val Pro Ala Trp Thr Thr Asp Ala Ser Leu Pro
                115                 120                 125

Gly Asp Gln Ser His Arg Asn Thr Ser Ala Cys Met Asn Ile Thr His
130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
                165                 170                 175

Tyr Leu His Arg Leu Ser Cys Tyr Gln His Ile Met Leu Phe Gly Cys
                180                 185                 190

Thr Leu Ala Phe Pro Glu Cys Ile Ile Asp Gly Asp Asp Ser His Gly
                195                 200                 205

Leu Leu Pro Cys Arg Ser Phe Cys Glu Ala Ala Lys Glu Gly Cys Glu
    210                 215                 220

Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
                260                 265                 270

Glu Asn Phe Leu Cys Ala Ser Gly Ile Cys Ile Pro Gly Lys Leu Gln
                275                 280                 285

Cys Asn Gly Tyr Asn Asp Cys Asp Asp Trp Ser Asp Glu Ala His Cys
    290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
                340                 345                 350

Gly Arg Cys Ile Ala Met Glu Trp Val Cys Asp Gly Asp His Asp Cys
                355                 360                 365

Val Asp Lys Ser Asp Glu Val Asn Cys Ser Cys His Ser Gln Gly Leu
    370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Asn Cys Ser Val
                405                 410                 415

Ile Gln Thr Ser Cys Gln Glu Gly Asp Gln Arg Cys Leu Tyr Asn Pro
                420                 425                 430

Cys Leu Asp Ser Cys Gly Gly Ser Ser Leu Cys Asp Pro Asn Asn Ser
    435                 440                 445

Leu Asn Asn Cys Ser Gln Cys Glu Pro Ile Thr Leu Glu Leu Cys Met
    450                 455                 460

Asn Leu Pro Tyr Asn Ser Thr Ser Tyr Pro Asn Tyr Phe Gly His Arg
465                 470                 475                 480
```

-continued

```
Thr Gln Lys Glu Ala Ser Ile Ser Trp Glu Ser Ser Leu Phe Pro Ala
            485                 490                 495
Leu Val Gln Thr Asn Cys Tyr Lys Tyr Leu Met Phe Phe Ser Cys Thr
            500                 505                 510
Ile Leu Val Pro Lys Cys Asp Val Asn Thr Gly Glu Arg Ile Pro Pro
            515                 520                 525
Cys Arg Ala Leu Cys Glu His Ser Lys Glu Arg Cys Glu Ser Val Leu
            530                 535                 540
Gly Ile Val Gly Leu Gln Trp Pro Glu Asp Thr Asp Cys Ser Gln Phe
545                 550                 555                 560
Pro Glu Glu Asn Ser Asp Asn Gln Thr Cys Leu Met Pro Asp Glu Tyr
            565                 570                 575
Val Glu Glu Cys Ser Pro Ser His Phe Lys Cys Arg Ser Gly Gln Cys
            580                 585                 590
Val Leu Ala Ser Arg Arg Cys Asp Gly Gln Ala Asp Cys Asp Asp Asp
            595                 600                 605
Ser Asp Glu Glu Asn Cys Gly Cys Lys Glu Arg Asp Leu Trp Glu Cys
            610                 615                 620
Pro Ser Asn Lys Gln Cys Leu Lys His Thr Val Ile Cys Asp Gly Phe
625                 630                 635                 640
Pro Asp Cys Pro Asp Tyr Met Asp Glu Lys Asn Cys Ser Phe Cys Gln
            645                 650                 655
Asp Asp Glu Leu Glu Cys Ala Asn His Ala Cys Val Ser Arg Asp Leu
            660                 665                 670
Trp Cys Asp Gly Glu Ala Asp Cys Ser Asp Ser Ser Asp Glu Trp Asp
            675                 680                 685
Cys Val Thr Leu Ser Ile Asn Val Asn Ser Ser Ser Phe Leu Met Val
            690                 695                 700
His Arg Ala Ala Thr Glu His His Val Cys Ala Asp Gly Trp Gln Glu
705                 710                 715                 720
Ile Leu Ser Gln Leu Ala Cys Lys Gln Met Gly Leu Gly Glu Pro Ser
            725                 730                 735
Val Thr Lys Leu Ile Gln Glu Gln Glu Lys Glu Pro Arg Trp Leu Thr
            740                 745                 750
Leu His Ser Asn Trp Glu Ser Leu Asn Gly Thr Thr Leu His Glu Leu
            755                 760                 765
Leu Val Asn Gly Gln Ser Cys Glu Ser Arg Ser Lys Ile Ser Leu Leu
            770                 775                 780
Cys Thr Lys Gln Asp Cys Gly Arg Arg Pro Ala Ala Arg Met Asn Lys
785                 790                 795                 800
Arg Ile Leu Gly Gly Arg Thr Ser Arg Pro Gly Arg Trp Pro Trp Gln
            805                 810                 815
Cys Ser Leu Gln Ser Glu Pro Ser Gly His Ile Cys Gly Cys Val Leu
            820                 825                 830
Ile Ala Lys Lys Trp Val Leu Thr Val Ala His Cys Phe Glu Gly Arg
            835                 840                 845
Glu Asn Ala Ala Val Trp Lys Val Val Leu Gly Ile Asn Asn Leu Asp
            850                 855                 860
His Pro Ser Val Phe Met Gln Thr Arg Phe Val Lys Thr Ile Ile Leu
865                 870                 875                 880
His Pro Arg Tyr Ser Arg Ala Val Val Asp Tyr Asp Ile Ser Ile Val
            885                 890                 895
```

-continued

```
Glu Leu Ser Glu Asp Ile Ser Glu Thr Gly Tyr Val Arg Pro Val Cys
            900                 905                 910
Leu Pro Asn Pro Glu Gln Trp Leu Glu Pro Asp Thr Tyr Cys Tyr Ile
        915                 920                 925
Thr Gly Trp Gly His Met Gly Asn Lys Met Pro Phe Lys Leu Gln Glu
    930                 935                 940
Gly Glu Val Arg Ile Ile Ser Leu Glu His Cys Gln Ser Tyr Phe Asp
945                 950                 955                 960
Met Lys Thr Ile Thr Thr Arg Met Ile Cys Ala Gly Tyr Glu Ser Gly
                965                 970                 975
Thr Val Asp Ser Cys Met Gly Asp Ser Gly Gly Pro Leu Val Cys Glu
            980                 985                 990
Lys Pro Gly Gly Arg Trp Thr Leu  Phe Gly Leu Thr Ser  Trp Gly Ser
        995                 1000                1005
Val Cys  Phe Ser Lys Val Leu  Gly Pro Gly Val Tyr   Ser Asn Val
    1010                1015                1020
Ser Tyr  Phe Val Glu Trp Ile  Lys Arg Gln Ile Tyr   Ile Gln Thr
    1025                1030                1035
Phe Leu  Leu Asn
    1040
```

<210> SEQ ID NO 3
<211> LENGTH: 34
<212> TYPE: DNA
<213> ORGANISM: Artificial
<220> FEATURE:
<223> OTHER INFORMATION: Forward Primer for Corin Polypeptide

<400> SEQUENCE: 3
atgaaacagt ctcctgccct cgctccggaa gagc        34

<210> SEQ ID NO 4
<211> LENGTH: 24
<212> TYPE: DNA
<213> ORGANISM: Artificial
<220> FEATURE:
<223> OTHER INFORMATION: Reverse Primer for Corin Polypeptide

<400> SEQUENCE: 4
gtttaggaga aaggtctgga tgta        24

<210> SEQ ID NO 5
<211> LENGTH: 44
<212> TYPE: DNA
<213> ORGANISM: Artificial
<220> FEATURE:
<223> OTHER INFORMATION: Forward Primer Cor/TMa

<400> SEQUENCE: 5
gggggaattc atgaaacagt ctcctgccct cgctccggaa gagc        44

<210> SEQ ID NO 6
<211> LENGTH: 38
<212> TYPE: DNA
<213> ORGANISM: Artificial
<220> FEATURE:
<223> OTHER INFORMATION: Reverse Primer Cor/TMb

<400> SEQUENCE: 6
ggggctcgag cgtagtccag gctggaacgt gttggtcg        38

```
<210> SEQ ID NO 7
<211> LENGTH: 43
<212> TYPE: DNA
<213> ORGANISM: Artificial
<220> FEATURE:
<223> OTHER INFORMATION: Forward Primer CorFL

<400> SEQUENCE: 7
ggggctcgag gatgcttctc tcccagggga ccaaagtcac agg                43

<210> SEQ ID NO 8
<211> LENGTH: 43
<212> TYPE: DNA
<213> ORGANISM: Artificial
<220> FEATURE:
<223> OTHER INFORMATION: Reverse Primer CorEnd

<400> SEQUENCE: 8 ggggggggccc ttagtttagg agaaaggtct ggatgtaaat ctg               43

<210> SEQ ID NO 9
<211> LENGTH: 1044
<212> TYPE: PRT
<213> ORGANISM: Artificial
<220> FEATURE:
<223> OTHER INFORMATION: Corin AA 1 to 123, Artificial XhoI Site, and
      Corin AA 124 to 1042

<400> SEQUENCE: 9
```

| Met | Lys | Gln | Ser | Pro | Ala | Leu | Ala | Pro | Glu | Glu | Arg | Tyr | Arg | Arg | Ala |
|---|---|---|---|---|---|---|---|---|---|---|---|---|---|---|---|
| 1 | | | | 5 | | | | | 10 | | | | | 15 | |

| Gly | Ser | Pro | Lys | Pro | Val | Leu | Arg | Ala | Asp | Asp | Asn | Asn | Met | Gly | Asn |
|---|---|---|---|---|---|---|---|---|---|---|---|---|---|---|---|
| | | | 20 | | | | | 25 | | | | | 30 | | |

| Gly | Cys | Ser | Gln | Lys | Leu | Ala | Thr | Ala | Asn | Leu | Leu | Arg | Phe | Leu | Leu |
|---|---|---|---|---|---|---|---|---|---|---|---|---|---|---|---|
| | | 35 | | | | | 40 | | | | | 45 | | | |

| Leu | Val | Leu | Ile | Pro | Cys | Ile | Cys | Ala | Leu | Val | Leu | Leu | Leu | Val | Ile |
|---|---|---|---|---|---|---|---|---|---|---|---|---|---|---|---|
| | 50 | | | | | 55 | | | | | 60 | | | | |

| Leu | Leu | Ser | Tyr | Val | Gly | Thr | Leu | Gln | Lys | Val | Tyr | Phe | Lys | Ser | Asn |
|---|---|---|---|---|---|---|---|---|---|---|---|---|---|---|---|
| 65 | | | | | 70 | | | | | 75 | | | | | 80 |

| Gly | Ser | Glu | Pro | Leu | Val | Thr | Asp | Gly | Glu | Ile | Gln | Gly | Ser | Asp | Val |
|---|---|---|---|---|---|---|---|---|---|---|---|---|---|---|---|
| | | | | 85 | | | | | 90 | | | | | 95 | |

| Ile | Leu | Thr | Asn | Thr | Ile | Tyr | Asn | Gln | Ser | Thr | Val | Val | Ser | Thr | Ala |
|---|---|---|---|---|---|---|---|---|---|---|---|---|---|---|---|
| | | | 100 | | | | | 105 | | | | | 110 | | |

| His | Pro | Asp | Gln | His | Val | Pro | Ala | Trp | Thr | Thr | Leu | Glu | Asp | Ala | Ser |
|---|---|---|---|---|---|---|---|---|---|---|---|---|---|---|---|
| | | 115 | | | | | 120 | | | | | 125 | | | |

| Leu | Pro | Gly | Asp | Gln | Ser | His | Arg | Asn | Thr | Ser | Ala | Cys | Met | Asn | Ile |
|---|---|---|---|---|---|---|---|---|---|---|---|---|---|---|---|
| | 130 | | | | | 135 | | | | | 140 | | | | |

| Thr | His | Ser | Gln | Cys | Gln | Met | Leu | Pro | Tyr | His | Ala | Thr | Leu | Thr | Pro |
|---|---|---|---|---|---|---|---|---|---|---|---|---|---|---|---|
| 145 | | | | | 150 | | | | | 155 | | | | | 160 |

| Leu | Leu | Ser | Val | Val | Arg | Asn | Met | Glu | Met | Glu | Lys | Phe | Leu | Lys | Phe |
|---|---|---|---|---|---|---|---|---|---|---|---|---|---|---|---|
| | | | | 165 | | | | | 170 | | | | | 175 | |

| Phe | Thr | Tyr | Leu | His | Arg | Leu | Ser | Cys | Tyr | Gln | His | Ile | Met | Leu | Phe |
|---|---|---|---|---|---|---|---|---|---|---|---|---|---|---|---|
| | | | 180 | | | | | 185 | | | | | 190 | | |

| Gly | Cys | Thr | Leu | Ala | Phe | Pro | Glu | Cys | Ile | Ile | Asp | Gly | Asp | Asp | Ser |
|---|---|---|---|---|---|---|---|---|---|---|---|---|---|---|---|
| | | 195 | | | | | 200 | | | | | 205 | | | |

| His | Gly | Leu | Leu | Pro | Cys | Arg | Ser | Phe | Cys | Glu | Ala | Ala | Lys | Glu | Gly |
|---|---|---|---|---|---|---|---|---|---|---|---|---|---|---|---|
| | 210 | | | | | 215 | | | | | 220 | | | | |

| Cys | Glu | Ser | Val | Leu | Gly | Met | Val | Asn | Tyr | Ser | Trp | Pro | Asp | Phe | Leu |
|---|---|---|---|---|---|---|---|---|---|---|---|---|---|---|---|
| 225 | | | | | 230 | | | | | 235 | | | | | 240 |

-continued

```
Arg Cys Ser Gln Phe Arg Asn Gln Thr Glu Ser Ser Asn Val Ser Arg
            245                 250                 255
Ile Cys Phe Ser Pro Gln Glu Asn Gly Lys Gln Leu Leu Cys Gly
        260                 265                 270
Arg Gly Glu Asn Phe Leu Cys Ala Ser Gly Ile Cys Ile Pro Gly Lys
            275                 280                 285
Leu Gln Cys Asn Gly Tyr Asn Asp Cys Asp Asp Trp Ser Asp Glu Ala
        290                 295                 300
His Cys Asn Cys Ser Glu Asn Leu Phe His Cys His Thr Gly Lys Cys
305                 310                 315                 320
Leu Asn Tyr Ser Leu Val Cys Asp Gly Tyr Asp Asp Cys Gly Asp Leu
                325                 330                 335
Ser Asp Glu Gln Asn Cys Asp Cys Asn Pro Thr Thr Glu His Arg Cys
            340                 345                 350
Gly Asp Gly Arg Cys Ile Ala Met Glu Trp Val Cys Asp Gly Asp His
            355                 360                 365
Asp Cys Val Asp Lys Ser Asp Glu Val Asn Cys Ser Cys His Ser Gln
        370                 375                 380
Gly Leu Val Glu Cys Arg Asn Gly Gln Cys Ile Pro Ser Thr Phe Gln
385                 390                 395                 400
Cys Asp Gly Asp Glu Asp Cys Lys Asp Gly Ser Asp Glu Asn Cys
                405                 410                 415
Ser Val Ile Gln Thr Ser Cys Gln Glu Gly Asp Gln Arg Cys Leu Tyr
            420                 425                 430
Asn Pro Cys Leu Asp Ser Cys Gly Gly Ser Ser Leu Cys Asp Pro Asn
        435                 440                 445
Asn Ser Leu Asn Asn Cys Ser Gln Cys Glu Pro Ile Thr Leu Glu Leu
        450                 455                 460
Cys Met Asn Leu Pro Tyr Asn Ser Thr Ser Tyr Pro Asn Tyr Phe Gly
465                 470                 475                 480
His Arg Thr Gln Lys Glu Ala Ser Ile Ser Trp Glu Ser Ser Leu Phe
            485                 490                 495
Pro Ala Leu Val Gln Thr Asn Cys Tyr Lys Tyr Leu Met Phe Phe Ser
        500                 505                 510
Cys Thr Ile Leu Val Pro Lys Cys Asp Val Asn Thr Gly Glu Arg Ile
        515                 520                 525
Pro Pro Cys Arg Ala Leu Cys Glu His Ser Lys Glu Arg Cys Glu Ser
        530                 535                 540
Val Leu Gly Ile Val Gly Leu Gln Trp Pro Glu Asp Thr Asp Cys Ser
545                 550                 555                 560
Gln Phe Pro Glu Glu Asn Ser Asp Asn Gln Thr Cys Leu Met Pro Asp
                565                 570                 575
Glu Tyr Val Glu Glu Cys Ser Pro Ser His Phe Lys Cys Arg Ser Gly
            580                 585                 590
Gln Cys Val Leu Ala Ser Arg Arg Cys Asp Gly Gln Ala Asp Cys Asp
        595                 600                 605
Asp Asp Ser Asp Glu Glu Asn Cys Gly Cys Lys Glu Arg Asp Leu Trp
    610                 615                 620
Glu Cys Pro Ser Asn Lys Gln Cys Leu Lys His Thr Val Ile Cys Asp
625                 630                 635                 640
Gly Phe Pro Asp Cys Pro Asp Tyr Met Asp Glu Lys Asn Cys Ser Phe
                645                 650                 655
Cys Gln Asp Asp Glu Leu Glu Cys Ala Asn His Ala Cys Val Ser Arg
```

```
                        660             665             670
Asp Leu Trp Cys Asp Gly Glu Ala Asp Cys Ser Asp Ser Asp Glu
            675                 680                 685

Trp Asp Cys Val Thr Leu Ser Ile Asn Val Asn Ser Ser Phe Leu
            690                 695                 700

Met Val His Arg Ala Ala Thr Glu His His Val Cys Ala Asp Gly Trp
705                 710                 715                 720

Gln Glu Ile Leu Ser Gln Leu Ala Cys Lys Gln Met Gly Leu Gly Glu
                725                 730                 735

Pro Ser Val Thr Lys Leu Ile Gln Glu Gln Lys Glu Pro Arg Trp
            740                 745                 750

Leu Thr Leu His Ser Asn Trp Glu Ser Leu Asn Gly Thr Thr Leu His
                755                 760                 765

Glu Leu Leu Val Asn Gly Gln Ser Cys Glu Ser Arg Ser Lys Ile Ser
770                 775                 780

Leu Leu Cys Thr Lys Gln Asp Cys Gly Arg Arg Pro Ala Ala Arg Met
785                 790                 795                 800

Asn Lys Arg Ile Leu Gly Gly Arg Thr Ser Arg Pro Gly Arg Trp Pro
                805                 810                 815

Trp Gln Cys Ser Leu Gln Ser Glu Pro Ser Gly His Ile Cys Gly Cys
            820                 825                 830

Val Leu Ile Ala Lys Lys Trp Val Leu Thr Val Ala His Cys Phe Glu
            835                 840                 845

Gly Arg Glu Asn Ala Ala Val Trp Lys Val Val Leu Gly Ile Asn Asn
850                 855                 860

Leu Asp His Pro Ser Val Phe Met Gln Thr Arg Phe Val Lys Thr Ile
865                 870                 875                 880

Ile Leu His Pro Arg Tyr Ser Arg Ala Val Val Asp Tyr Asp Ile Ser
                885                 890                 895

Ile Val Glu Leu Ser Glu Asp Ile Ser Glu Thr Gly Tyr Val Arg Pro
                900                 905                 910

Val Cys Leu Pro Asn Pro Glu Gln Trp Leu Glu Pro Asp Thr Tyr Cys
            915                 920                 925

Tyr Ile Thr Gly Trp Gly His Met Gly Asn Lys Met Pro Phe Lys Leu
930                 935                 940

Gln Glu Gly Glu Val Arg Ile Ile Ser Leu Glu His Cys Gln Ser Tyr
945                 950                 955                 960

Phe Asp Met Lys Thr Ile Thr Thr Arg Met Ile Cys Ala Gly Tyr Glu
                965                 970                 975

Ser Gly Thr Val Asp Ser Cys Met Gly Asp Ser Gly Gly Pro Leu Val
            980                 985                 990

Cys Glu Lys Pro Gly Gly Arg Trp Thr Leu Phe Gly Leu Thr Ser Trp
            995                 1000                1005

Gly Ser Val Cys Phe Ser Lys Val Leu Gly Pro Gly Val Tyr Ser
    1010                1015                1020

Asn Val Ser Tyr Phe Val Glu Trp Ile Lys Arg Gln Ile Tyr Ile
    1025                1030                1035

Gln Thr Phe Leu Leu Asn
    1040

<210> SEQ ID NO 10
<211> LENGTH: 42
<212> TYPE: DNA
<213> ORGANISM: Artificial
```

-continued

```
<220> FEATURE:
<223> OTHER INFORMATION: Forward Primer CorDel I

<400> SEQUENCE: 10
ggggctcgag ctctgtggaa ggggtgagaa ctttctgtgt gc                    42

<210> SEQ ID NO 11
<211> LENGTH: 36
<212> TYPE: DNA
<213> ORGANISM: Artificial
<220> FEATURE:
<223> OTHER INFORMATION: Forward Primer CorDel II

<400> SEQUENCE: 11
ggggctcgag ctgaataact gtagtcaatg tgaacc                           36

<210> SEQ ID NO 12
<211> LENGTH: 40
<212> TYPE: DNA
<213> ORGANISM: Artificial
<220> FEATURE:
<223> OTHER INFORMATION: Forward Primer CorDel III

<400> SEQUENCE: 12
ggggctcgag gtggaagaat gctcacctag tcatttcaag                       40

<210> SEQ ID NO 13
<211> LENGTH: 40
<212> TYPE: DNA
<213> ORGANISM: Artificial
<220> FEATURE:
<223> OTHER INFORMATION: Forward Primer CorDel IV

<400> SEQUENCE: 13
ggggctcgag gtgtgtgcag atggctggca ggagatattg                       40

<210> SEQ ID NO 14
<211> LENGTH: 40
<212> TYPE: DNA
<213> ORGANISM: Artificial
<220> FEATURE:
<223> OTHER INFORMATION: Forward Primer CorDel V

<400> SEQUENCE: 14
ggggctcgag gactgtgggc gccgccctgc tgcccgaatg                       40

<210> SEQ ID NO 15
<211> LENGTH: 900
<212> TYPE: PRT
<213> ORGANISM: Artificial
<220> FEATURE:
<223> OTHER INFORMATION: Corin AA 1 to 123, Artificial XhoI Site, and
      Corin AA 268 to 1042

<400> SEQUENCE: 15

Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Val Ile
    50                  55                  60

Leu Leu Ser Tyr Val Gly Thr Leu Gln Lys Val Tyr Phe Lys Ser Asn
```

-continued

```
            65                  70                  75                  80
Gly Ser Glu Pro Leu Val Thr Asp Gly Glu Ile Gln Gly Ser Asp Val
                    85                  90                  95
Ile Leu Thr Asn Thr Ile Tyr Asn Gln Ser Thr Val Val Ser Thr Ala
                    100                 105                 110
His Pro Asp Gln His Val Pro Ala Trp Thr Thr Leu Glu Leu Cys Gly
                    115                 120                 125
Arg Gly Glu Asn Phe Leu Cys Ala Ser Gly Ile Cys Ile Pro Gly Lys
                    130                 135                 140
Leu Gln Cys Asn Gly Tyr Asn Asp Cys Asp Asp Trp Ser Asp Glu Ala
145                 150                 155                 160
His Cys Asn Cys Ser Glu Asn Leu Phe His Cys His Thr Gly Lys Cys
                    165                 170                 175
Leu Asn Tyr Ser Leu Val Cys Asp Gly Tyr Asp Asp Cys Gly Asp Leu
                    180                 185                 190
Ser Asp Glu Gln Asn Cys Asp Cys Asn Pro Thr Thr Glu His Arg Cys
                    195                 200                 205
Gly Asp Gly Arg Cys Ile Ala Met Glu Trp Val Cys Asp Gly Asp His
                    210                 215                 220
Asp Cys Val Asp Lys Ser Asp Glu Val Asn Cys Ser Cys His Ser Gln
225                 230                 235                 240
Gly Leu Val Glu Cys Arg Asn Gly Gln Cys Ile Pro Ser Thr Phe Gln
                    245                 250                 255
Cys Asp Gly Asp Glu Asp Cys Lys Asp Gly Ser Asp Glu Glu Asn Cys
                    260                 265                 270
Ser Val Ile Gln Thr Ser Cys Gln Glu Gly Asp Gln Arg Cys Leu Tyr
                    275                 280                 285
Asn Pro Cys Leu Asp Ser Cys Gly Gly Ser Ser Leu Cys Asp Pro Asn
                    290                 295                 300
Asn Ser Leu Asn Asn Cys Ser Gln Cys Glu Pro Ile Thr Leu Glu Leu
305                 310                 315                 320
Cys Met Asn Leu Pro Tyr Asn Ser Thr Ser Tyr Pro Asn Tyr Phe Gly
                    325                 330                 335
His Arg Thr Gln Lys Glu Ala Ser Ile Ser Trp Glu Ser Ser Leu Phe
                    340                 345                 350
Pro Ala Leu Val Gln Thr Asn Cys Tyr Lys Tyr Leu Met Phe Phe Ser
                    355                 360                 365
Cys Thr Ile Leu Val Pro Lys Cys Asp Val Asn Thr Gly Glu Arg Ile
                    370                 375                 380
Pro Pro Cys Arg Ala Leu Cys Glu His Ser Lys Glu Arg Cys Glu Ser
385                 390                 395                 400
Val Leu Gly Ile Val Gly Leu Gln Trp Pro Glu Asp Thr Asp Cys Ser
                    405                 410                 415
Gln Phe Pro Glu Glu Asn Ser Asp Asn Gln Thr Cys Leu Met Pro Asp
                    420                 425                 430
Glu Tyr Val Glu Glu Cys Ser Pro Ser His Phe Lys Cys Arg Ser Gly
                    435                 440                 445
Gln Cys Val Leu Ala Ser Arg Arg Cys Asp Gly Gln Ala Asp Cys Asp
                    450                 455                 460
Asp Asp Ser Asp Glu Glu Asn Cys Gly Cys Lys Glu Arg Asp Leu Trp
465                 470                 475                 480
Glu Cys Pro Ser Asn Lys Gln Cys Leu Lys His Thr Val Ile Cys Asp
                    485                 490                 495
```

```
Gly Phe Pro Asp Cys Pro Asp Tyr Met Asp Glu Lys Asn Cys Ser Phe
            500                 505                 510

Cys Gln Asp Asp Glu Leu Glu Cys Ala Asn His Ala Cys Val Ser Arg
            515                 520                 525

Asp Leu Trp Cys Asp Gly Glu Ala Asp Cys Ser Asp Ser Ser Asp Glu
            530                 535                 540

Trp Asp Cys Val Thr Leu Ser Ile Asn Val Asn Ser Ser Ser Phe Leu
545                 550                 555                 560

Met Val His Arg Ala Ala Thr Glu His His Val Cys Ala Asp Gly Trp
            565                 570                 575

Gln Glu Ile Leu Ser Gln Leu Ala Cys Lys Gln Met Gly Leu Gly Glu
            580                 585                 590

Pro Ser Val Thr Lys Leu Ile Gln Glu Gln Lys Glu Pro Arg Trp
            595                 600                 605

Leu Thr Leu His Ser Asn Trp Glu Ser Leu Asn Gly Thr Thr Leu His
            610                 615                 620

Glu Leu Leu Val Asn Gly Gln Ser Cys Glu Ser Arg Ser Lys Ile Ser
625                 630                 635                 640

Leu Leu Cys Thr Lys Gln Asp Cys Gly Arg Arg Pro Ala Ala Arg Met
            645                 650                 655

Asn Lys Arg Ile Leu Gly Gly Arg Thr Ser Arg Pro Gly Arg Trp Pro
            660                 665                 670

Trp Gln Cys Ser Leu Gln Ser Glu Pro Ser Gly His Ile Cys Gly Cys
            675                 680                 685

Val Leu Ile Ala Lys Lys Trp Val Leu Thr Val Ala His Cys Phe Glu
            690                 695                 700

Gly Arg Glu Asn Ala Ala Val Trp Lys Val Val Leu Gly Ile Asn Asn
705                 710                 715                 720

Leu Asp His Pro Ser Val Phe Met Gln Thr Arg Phe Val Lys Thr Ile
            725                 730                 735

Ile Leu His Pro Arg Tyr Ser Arg Ala Val Val Asp Tyr Asp Ile Ser
            740                 745                 750

Ile Val Glu Leu Ser Glu Asp Ile Ser Glu Thr Gly Tyr Val Arg Pro
            755                 760                 765

Val Cys Leu Pro Asn Pro Glu Gln Trp Leu Glu Pro Asp Thr Tyr Cys
            770                 775                 780

Tyr Ile Thr Gly Trp Gly His Met Gly Asn Lys Met Pro Phe Lys Leu
785                 790                 795                 800

Gln Glu Gly Glu Val Arg Ile Ile Ser Leu Glu His Cys Gln Ser Tyr
            805                 810                 815

Phe Asp Met Lys Thr Ile Thr Thr Arg Met Ile Cys Ala Gly Tyr Glu
            820                 825                 830

Ser Gly Thr Val Asp Ser Cys Met Gly Asp Ser Gly Gly Pro Leu Val
            835                 840                 845

Cys Glu Lys Pro Gly Gly Arg Trp Thr Leu Phe Gly Leu Thr Ser Trp
            850                 855                 860

Gly Ser Val Cys Phe Ser Lys Val Leu Gly Pro Gly Val Tyr Ser Asn
865                 870                 875                 880

Val Ser Tyr Phe Val Glu Trp Ile Lys Arg Gln Ile Tyr Ile Gln Thr
            885                 890                 895

Phe Leu Leu Asn
            900
```

```
<210> SEQ ID NO 16
<211> LENGTH: 719
<212> TYPE: PRT
<213> ORGANISM: Artificial
<220> FEATURE:
<223> OTHER INFORMATION: Corin AA 1 to 123, Artificial XhoI site, and
      Corin AA 449 to 1042

<400> SEQUENCE: 16

Met Lys Gln Ser Pro Ala Leu Ala Pro Glu Arg Tyr Arg Arg Ala
1               5                   10                  15

Gly Ser Pro Lys Pro Val Leu Arg Ala Asp Asp Asn Asn Met Gly Asn
                20                  25                  30

Gly Cys Ser Gln Lys Leu Ala Thr Ala Asn Leu Leu Arg Phe Leu Leu
            35                  40                  45

Leu Val Leu Ile Pro Cys Ile Cys Ala Leu Val Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
                100                 105                 110

His Pro Asp Gln His Val Pro Ala Trp Thr Thr Leu Glu Leu Asn Asn
            115                 120                 125

Cys Ser Gln Cys Glu Pro Ile Thr Leu Glu Leu Cys Met Asn Leu Pro
130                 135                 140

Tyr Asn Ser Thr Ser Tyr Pro Asn Tyr Phe Gly His Arg Thr Gln Lys
145                 150                 155                 160

Glu Ala Ser Ile Ser Trp Glu Ser Ser Leu Phe Pro Ala Leu Val Gln
                165                 170                 175

Thr Asn Cys Tyr Lys Tyr Leu Met Phe Phe Ser Cys Thr Ile Leu Val
            180                 185                 190

Pro Lys Cys Asp Val Asn Thr Gly Glu Arg Ile Pro Pro Cys Arg Ala
        195                 200                 205

Leu Cys Glu His Ser Lys Glu Arg Cys Glu Ser Val Leu Gly Ile Val
    210                 215                 220

Gly Leu Gln Trp Pro Glu Asp Thr Asp Cys Ser Gln Phe Pro Glu Glu
225                 230                 235                 240

Asn Ser Asp Asn Gln Thr Cys Leu Met Pro Asp Glu Tyr Val Glu Glu
                245                 250                 255

Cys Ser Pro Ser His Phe Lys Cys Arg Ser Gly Gln Cys Val Leu Ala
            260                 265                 270

Ser Arg Arg Cys Asp Gly Gln Ala Asp Cys Asp Asp Ser Asp Glu
        275                 280                 285

Glu Asn Cys Gly Cys Lys Glu Arg Asp Leu Trp Glu Cys Pro Ser Asn
    290                 295                 300

Lys Gln Cys Leu Lys His Thr Val Ile Cys Asp Gly Phe Pro Asp Cys
305                 310                 315                 320

Pro Asp Tyr Met Asp Glu Lys Asn Cys Ser Phe Cys Gln Asp Glu
                325                 330                 335

Leu Glu Cys Ala Asn His Ala Cys Val Ser Arg Asp Leu Trp Cys Asp
            340                 345                 350

Gly Glu Ala Asp Cys Ser Asp Ser Ser Asp Glu Trp Asp Cys Val Thr
        355                 360                 365
```

-continued

```
Leu Ser Ile Asn Val Asn Ser Ser Phe Leu Met Val His Arg Ala
        370                 375                 380

Ala Thr Glu His His Val Cys Ala Asp Gly Trp Gln Glu Ile Leu Ser
385                 390                 395                 400

Gln Leu Ala Cys Lys Gln Met Gly Leu Gly Glu Pro Ser Val Thr Lys
                405                 410                 415

Leu Ile Gln Glu Gln Lys Glu Pro Arg Trp Leu Thr Leu His Ser
            420                 425                 430

Asn Trp Glu Ser Leu Asn Gly Thr Thr Leu His Glu Leu Leu Val Asn
                435                 440                 445

Gly Gln Ser Cys Glu Ser Arg Ser Lys Ile Ser Leu Leu Cys Thr Lys
    450                 455                 460

Gln Asp Cys Gly Arg Arg Pro Ala Ala Arg Met Asn Lys Arg Ile Leu
465                 470                 475                 480

Gly Gly Arg Thr Ser Arg Pro Gly Arg Trp Pro Trp Gln Cys Ser Leu
                485                 490                 495

Gln Ser Glu Pro Ser Gly His Ile Cys Gly Cys Val Leu Ile Ala Lys
            500                 505                 510

Lys Trp Val Leu Thr Val Ala His Cys Phe Glu Gly Arg Glu Asn Ala
            515                 520                 525

Ala Val Trp Lys Val Val Leu Gly Ile Asn Asn Leu Asp His Pro Ser
    530                 535                 540

Val Phe Met Gln Thr Arg Phe Val Lys Thr Ile Ile Leu His Pro Arg
545                 550                 555                 560

Tyr Ser Arg Ala Val Val Asp Tyr Asp Ile Ser Ile Val Glu Leu Ser
                565                 570                 575

Glu Asp Ile Ser Glu Thr Gly Tyr Val Arg Pro Val Cys Leu Pro Asn
            580                 585                 590

Pro Glu Gln Trp Leu Glu Pro Asp Thr Tyr Cys Tyr Ile Thr Gly Trp
            595                 600                 605

Gly His Met Gly Asn Lys Met Pro Phe Lys Leu Gln Glu Gly Glu Val
    610                 615                 620

Arg Ile Ile Ser Leu Glu His Cys Gln Ser Tyr Phe Asp Met Lys Thr
625                 630                 635                 640

Ile Thr Thr Arg Met Ile Cys Ala Gly Tyr Glu Ser Gly Thr Val Asp
                645                 650                 655

Ser Cys Met Gly Asp Ser Gly Gly Pro Leu Val Cys Glu Lys Pro Gly
            660                 665                 670

Gly Arg Trp Thr Leu Phe Gly Leu Thr Ser Trp Gly Ser Val Cys Phe
            675                 680                 685

Ser Lys Val Leu Gly Pro Gly Val Tyr Ser Asn Val Ser Tyr Phe Val
    690                 695                 700

Glu Trp Ile Lys Arg Gln Ile Tyr Ile Gln Thr Phe Leu Leu Asn
705                 710                 715
```

<210> SEQ ID NO 17
<211> LENGTH: 591
<212> TYPE: PRT
<213> ORGANISM: Artificial
<220> FEATURE:
<223> OTHER INFORMATION: Corin AA 1 to 123, Artificial XhoI site, and
      Corin AA 577 to 1042

<400> SEQUENCE: 17

Met Lys Gln Ser Pro Ala Leu Ala Pro Glu Glu Arg Tyr Arg Arg Ala

-continued

```
1               5                   10                  15
Gly Ser Pro Lys Pro Val Leu Arg Ala Asp Asp Asn Asn Met Gly Asn
            20                  25                  30
Gly Cys Ser Gln Lys Leu Ala Thr Ala Asn Leu Leu Arg Phe Leu Leu
            35                  40                  45
Leu Val Leu Ile Pro Cys Ile Cys Ala Leu Val Leu Leu Leu Val Ile
        50                  55                  60
Leu Leu Ser Tyr Val Gly Thr Leu Gln Lys Val Tyr Phe Lys Ser Asn
65                      70                  75                  80
Gly Ser Glu Pro Leu Val Thr Asp Gly Glu Ile Gln Gly Ser Asp Val
                85                  90                  95
Ile Leu Thr Asn Thr Ile Tyr Asn Gln Ser Thr Val Val Ser Thr Ala
                100                 105                 110
His Pro Asp Gln His Val Pro Ala Trp Thr Thr Leu Glu Val Glu Glu
            115                 120                 125
Cys Ser Pro Ser His Phe Lys Cys Arg Ser Gly Gln Cys Val Leu Ala
        130                 135                 140
Ser Arg Arg Cys Asp Gly Gln Ala Asp Cys Asp Asp Asp Ser Asp Glu
145                 150                 155                 160
Glu Asn Cys Gly Cys Lys Glu Arg Asp Leu Trp Glu Cys Pro Ser Asn
                165                 170                 175
Lys Gln Cys Leu Lys His Thr Val Ile Cys Asp Gly Phe Pro Asp Cys
                180                 185                 190
Pro Asp Tyr Met Asp Glu Lys Asn Cys Ser Phe Cys Gln Asp Glu
            195                 200                 205
Leu Glu Cys Ala Asn His Ala Cys Val Ser Arg Asp Leu Trp Cys Asp
        210                 215                 220
Gly Glu Ala Asp Cys Ser Asp Ser Ser Asp Glu Trp Asp Cys Val Thr
225                 230                 235                 240
Leu Ser Ile Asn Val Asn Ser Ser Ser Phe Leu Met Val His Arg Ala
                245                 250                 255
Ala Thr Glu His His Val Cys Ala Asp Gly Trp Gln Glu Ile Leu Ser
            260                 265                 270
Gln Leu Ala Cys Lys Gln Met Gly Leu Gly Glu Pro Ser Val Thr Lys
        275                 280                 285
Leu Ile Gln Glu Gln Glu Lys Glu Pro Arg Trp Leu Thr Leu His Ser
    290                 295                 300
Asn Trp Glu Ser Leu Asn Gly Thr Thr Leu His Glu Leu Leu Val Asn
305                 310                 315                 320
Gly Gln Ser Cys Glu Ser Arg Ser Lys Ile Ser Leu Leu Cys Thr Lys
                325                 330                 335
Gln Asp Cys Gly Arg Arg Pro Ala Ala Arg Met Asn Lys Arg Ile Leu
            340                 345                 350
Gly Gly Arg Thr Ser Arg Pro Gly Arg Trp Pro Trp Gln Cys Ser Leu
        355                 360                 365
Gln Ser Glu Pro Ser Gly His Ile Cys Gly Cys Val Leu Ile Ala Lys
    370                 375                 380
Lys Trp Val Leu Thr Val Ala His Cys Phe Glu Gly Arg Glu Asn Ala
385                 390                 395                 400
Ala Val Trp Lys Val Val Leu Gly Ile Asn Asn Leu Asp His Pro Ser
                405                 410                 415
Val Phe Met Gln Thr Arg Phe Val Lys Thr Ile Ile Leu His Pro Arg
            420                 425                 430
```

```
Tyr Ser Arg Ala Val Val Asp Tyr Asp Ile Ser Ile Val Glu Leu Ser
        435                 440                 445

Glu Asp Ile Ser Glu Thr Gly Tyr Val Arg Pro Val Cys Leu Pro Asn
    450                 455                 460

Pro Glu Gln Trp Leu Glu Pro Asp Thr Tyr Cys Tyr Ile Thr Gly Trp
465                 470                 475                 480

Gly His Met Gly Asn Lys Met Pro Phe Lys Leu Gln Glu Gly Glu Val
                485                 490                 495

Arg Ile Ile Ser Leu Glu His Cys Gln Ser Tyr Phe Asp Met Lys Thr
                500                 505                 510

Ile Thr Thr Arg Met Ile Cys Ala Gly Tyr Glu Ser Gly Thr Val Asp
            515                 520                 525

Ser Cys Met Gly Asp Ser Gly Gly Pro Leu Val Cys Glu Lys Pro Gly
        530                 535                 540

Gly Arg Trp Thr Leu Phe Gly Leu Thr Ser Trp Gly Ser Val Cys Phe
545                 550                 555                 560

Ser Lys Val Leu Gly Pro Gly Val Tyr Ser Asn Val Ser Tyr Phe Val
                565                 570                 575

Glu Trp Ile Lys Arg Gln Ile Tyr Ile Gln Thr Phe Leu Leu Asn
                580                 585                 590

<210> SEQ ID NO 18
<211> LENGTH: 455
<212> TYPE: PRT
<213> ORGANISM: Artificial
<220> FEATURE:
<223> OTHER INFORMATION: Corin AA 1 to 123, Artificial XhoI Site, and
      Corin AA 713 to 1042

<400> SEQUENCE: 18

Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
                100                 105                 110

His Pro Asp Gln His Val Pro Ala Trp Thr Thr Leu Glu Val Cys Ala
            115                 120                 125

Asp Gly Trp Gln Glu Ile Leu Ser Gln Leu Ala Cys Lys Gln Met Gly
        130                 135                 140

Leu Gly Glu Pro Ser Val Thr Lys Leu Ile Gln Glu Gln Lys Glu
145                 150                 155                 160

Pro Arg Trp Leu Thr Leu His Ser Asn Trp Glu Ser Leu Asn Gly Thr
                165                 170                 175

Thr Leu His Glu Leu Leu Val Asn Gly Gln Ser Cys Glu Ser Arg Ser
            180                 185                 190

Lys Ile Ser Leu Leu Cys Thr Lys Gln Asp Cys Gly Arg Arg Pro Ala
```

-continued

```
                195                 200                 205
Ala Arg Met Asn Lys Arg Ile Leu Gly Gly Arg Thr Ser Arg Pro Gly
    210                 215                 220

Arg Trp Pro Trp Gln Cys Ser Leu Gln Ser Glu Pro Ser Gly His Ile
225                 230                 235                 240

Cys Gly Cys Val Leu Ile Ala Lys Lys Trp Val Leu Thr Val Ala His
                245                 250                 255

Cys Phe Glu Gly Arg Glu Asn Ala Ala Val Trp Lys Val Val Leu Gly
                260                 265                 270

Ile Asn Asn Leu Asp His Pro Ser Val Phe Met Gln Thr Arg Phe Val
            275                 280                 285

Lys Thr Ile Ile Leu His Pro Arg Tyr Ser Arg Ala Val Val Asp Tyr
        290                 295                 300

Asp Ile Ser Ile Val Glu Leu Ser Glu Asp Ile Ser Glu Thr Gly Tyr
305                 310                 315                 320

Val Arg Pro Val Cys Leu Pro Asn Pro Glu Gln Trp Leu Glu Pro Asp
                325                 330                 335

Thr Tyr Cys Tyr Ile Thr Gly Trp Gly His Met Gly Asn Lys Met Pro
                340                 345                 350

Phe Lys Leu Gln Glu Gly Glu Val Arg Ile Ile Ser Leu Glu His Cys
            355                 360                 365

Gln Ser Tyr Phe Asp Met Lys Thr Ile Thr Thr Arg Met Ile Cys Ala
        370                 375                 380

Gly Tyr Glu Ser Gly Thr Val Asp Ser Cys Met Gly Asp Ser Gly Gly
385                 390                 395                 400

Pro Leu Val Cys Glu Lys Pro Gly Gly Arg Trp Thr Leu Phe Gly Leu
                405                 410                 415

Thr Ser Trp Gly Ser Val Cys Phe Ser Lys Val Leu Gly Pro Gly Val
                420                 425                 430

Tyr Ser Asn Val Ser Tyr Phe Val Glu Trp Ile Lys Arg Gln Ile Tyr
            435                 440                 445

Ile Gln Thr Phe Leu Leu Asn
    450                 455
```

<210> SEQ ID NO 19
<211> LENGTH: 379
<212> TYPE: PRT
<213> ORGANISM: Artificial
<220> FEATURE:
<223> OTHER INFORMATION: Corin AA 1 to 123, Artificial XhoI Site, and
    Corin AA 789 to 1042

<400> SEQUENCE: 19

```
Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Met Gly Asn
                20                  25                  30

Gly Cys Ser Gln Lys Leu Ala Thr Ala Asn Leu Leu Arg Phe Leu Leu
            35                  40                  45

Leu Val Leu Ile Pro Cys Ile Cys Ala Leu Val Leu Leu Val Ile
        50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95
```

```
Ile Leu Thr Asn Thr Ile Tyr Asn Gln Ser Thr Val Val Ser Thr Ala
            100                 105                 110

His Pro Asp Gln His Val Pro Ala Trp Thr Thr Leu Glu Asp Cys Gly
        115                 120                 125

Arg Arg Pro Ala Ala Arg Met Asn Lys Arg Ile Leu Gly Gly Arg Thr
    130                 135                 140

Ser Arg Pro Gly Arg Trp Pro Trp Gln Cys Ser Leu Gln Ser Glu Pro
145                 150                 155                 160

Ser Gly His Ile Cys Gly Cys Val Leu Ile Ala Lys Lys Trp Val Leu
                165                 170                 175

Thr Val Ala His Cys Phe Glu Gly Arg Glu Asn Ala Ala Val Trp Lys
            180                 185                 190

Val Val Leu Gly Ile Asn Asn Leu Asp His Pro Ser Val Phe Met Gln
        195                 200                 205

Thr Arg Phe Val Lys Thr Ile Ile Leu His Pro Arg Tyr Ser Arg Ala
    210                 215                 220

Val Val Asp Tyr Asp Ile Ser Ile Val Glu Leu Ser Glu Asp Ile Ser
225                 230                 235                 240

Glu Thr Gly Tyr Val Arg Pro Val Cys Leu Pro Asn Pro Glu Gln Trp
                245                 250                 255

Leu Glu Pro Asp Thr Tyr Cys Tyr Ile Thr Gly Trp Gly His Met Gly
            260                 265                 270

Asn Lys Met Pro Phe Lys Leu Gln Glu Gly Glu Val Arg Ile Ile Ser
        275                 280                 285

Leu Glu His Cys Gln Ser Tyr Phe Asp Met Lys Thr Ile Thr Thr Arg
    290                 295                 300

Met Ile Cys Ala Gly Tyr Glu Ser Gly Thr Val Asp Ser Cys Met Gly
305                 310                 315                 320

Asp Ser Gly Gly Pro Leu Val Cys Glu Lys Pro Gly Gly Arg Trp Thr
                325                 330                 335

Leu Phe Gly Leu Thr Ser Trp Gly Ser Val Cys Phe Ser Lys Val Leu
            340                 345                 350

Gly Pro Gly Val Tyr Ser Asn Val Ser Tyr Phe Val Glu Trp Ile Lys
        355                 360                 365

Arg Gln Ile Tyr Ile Gln Thr Phe Leu Leu Asn
    370                 375

<210> SEQ ID NO 20
<211> LENGTH: 39
<212> TYPE: DNA
<213> ORGANISM: Artificial
<220> FEATURE:
<223> OTHER INFORMATION: Reverse Primer Del 62

<400> SEQUENCE: 20
ggggctcgag aggtgagaag caaattctgc tgacattgc                          39

<210> SEQ ID NO 21
<211> LENGTH: 39
<212> TYPE: DNA
<213> ORGANISM: Artificial
<220> FEATURE:
<223> OTHER INFORMATION: Forward Primer Del 61

<400> SEQUENCE: 21
ggggctcgag agcgtcattc agacttcatg tcaagaagg                          39
```

-continued

```
<210> SEQ ID NO 22
<211> LENGTH: 889
<212> TYPE: PRT
<213> ORGANISM: Artificial
<220> FEATURE:
<223> OTHER INFORMATION: Corin AA 1 to 259, Artificial XhoI Site, and
      Corin AA 415 to 1042

<400> SEQUENCE: 22
```

| | | | | | | | | | | | | | | | |
|---|---|---|---|---|---|---|---|---|---|---|---|---|---|---|---|
| Met | Lys | Gln | Ser | Pro | Ala | Leu | Ala | Pro | Glu | Glu | Arg | Tyr | Arg | Arg | Ala |
| 1 | | | | 5 | | | | | 10 | | | | | 15 | |
| Gly | Ser | Pro | Lys | Pro | Val | Leu | Arg | Ala | Asp | Asp | Asn | Asn | Met | Gly | Asn |
| | | | 20 | | | | | 25 | | | | | 30 | | |
| Gly | Cys | Ser | Gln | Lys | Leu | Ala | Thr | Ala | Asn | Leu | Leu | Arg | Phe | Leu | Leu |
| | | 35 | | | | | 40 | | | | | 45 | | | |
| Leu | Val | Leu | Ile | Pro | Cys | Ile | Cys | Ala | Leu | Val | Leu | Leu | Val | Ile | |
| | 50 | | | | | 55 | | | | | 60 | | | | |
| Leu | Leu | Ser | Tyr | Val | Gly | Thr | Leu | Gln | Lys | Val | Tyr | Phe | Lys | Ser | Asn |
| 65 | | | | | 70 | | | | | 75 | | | | | 80 |
| Gly | Ser | Glu | Pro | Leu | Val | Thr | Asp | Gly | Glu | Ile | Gln | Gly | Ser | Asp | Val |
| | | | | 85 | | | | | 90 | | | | | 95 | |
| Ile | Leu | Thr | Asn | Thr | Ile | Tyr | Asn | Gln | Ser | Thr | Val | Val | Ser | Thr | Ala |
| | | | 100 | | | | | 105 | | | | | 110 | | |
| His | Pro | Asp | Gln | His | Val | Pro | Ala | Trp | Thr | Thr | Asp | Ala | Ser | Leu | Pro |
| | | 115 | | | | | 120 | | | | | 125 | | | |
| Gly | Asp | Gln | Ser | His | Arg | Asn | Thr | Ser | Ala | Cys | Met | Asn | Ile | Thr | His |
| | 130 | | | | | 135 | | | | | 140 | | | | |
| Ser | Gln | Cys | Gln | Met | Leu | Pro | Tyr | His | Ala | Thr | Leu | Thr | Pro | Leu | Leu |
| 145 | | | | | 150 | | | | | 155 | | | | | 160 |
| Ser | Val | Val | Arg | Asn | Met | Glu | Met | Glu | Lys | Phe | Leu | Lys | Phe | Phe | Thr |
| | | | | 165 | | | | | 170 | | | | | 175 | |
| Tyr | Leu | His | Arg | Leu | Ser | Cys | Tyr | Gln | His | Ile | Met | Leu | Phe | Gly | Cys |
| | | | 180 | | | | | 185 | | | | | 190 | | |
| Thr | Leu | Ala | Phe | Pro | Glu | Cys | Ile | Ile | Asp | Gly | Asp | Asp | Ser | His | Gly |
| | | 195 | | | | | 200 | | | | | 205 | | | |
| Leu | Leu | Pro | Cys | Arg | Ser | Phe | Cys | Glu | Ala | Ala | Lys | Glu | Gly | Cys | Glu |
| | 210 | | | | | 215 | | | | | 220 | | | | |
| Ser | Val | Leu | Gly | Met | Val | Asn | Tyr | Ser | Trp | Pro | Asp | Phe | Leu | Arg | Cys |
| 225 | | | | | 230 | | | | | 235 | | | | | 240 |
| Ser | Gln | Phe | Arg | Asn | Gln | Thr | Glu | Ser | Ser | Asn | Val | Ser | Arg | Ile | Cys |
| | | | | 245 | | | | | 250 | | | | | 255 | |
| Phe | Ser | Pro | Leu | Glu | Ser | Val | Ile | Gln | Thr | Ser | Cys | Gln | Glu | Gly | Asp |
| | | | 260 | | | | | 265 | | | | | 270 | | |
| Gln | Arg | Cys | Leu | Tyr | Asn | Pro | Cys | Leu | Asp | Ser | Cys | Gly | Gly | Ser | Ser |
| | | 275 | | | | | 280 | | | | | 285 | | | |
| Leu | Cys | Asp | Pro | Asn | Asn | Ser | Leu | Asn | Cys | Ser | Gln | Cys | Glu | Pro | |
| | 290 | | | | | 295 | | | | | 300 | | | | |
| Ile | Thr | Leu | Glu | Leu | Cys | Met | Asn | Leu | Pro | Tyr | Asn | Ser | Thr | Ser | Tyr |
| 305 | | | | | 310 | | | | | 315 | | | | | 320 |
| Pro | Asn | Tyr | Phe | Gly | His | Arg | Thr | Gln | Lys | Glu | Ala | Ser | Ile | Ser | Trp |
| | | | | 325 | | | | | 330 | | | | | 335 | |
| Glu | Ser | Ser | Leu | Phe | Pro | Ala | Leu | Val | Gln | Thr | Asn | Cys | Tyr | Lys | Tyr |
| | | | 340 | | | | | 345 | | | | | 350 | | |
| Leu | Met | Phe | Phe | Ser | Cys | Thr | Ile | Leu | Val | Pro | Lys | Cys | Asp | Val | Asn |
| | | 355 | | | | | 360 | | | | | 365 | | | |

-continued

```
Thr Gly Glu Arg Ile Pro Pro Cys Arg Ala Leu Cys Glu His Ser Lys
    370                 375                 380
Glu Arg Cys Glu Ser Val Leu Gly Ile Val Gly Leu Gln Trp Pro Glu
385                 390                 395                 400
Asp Thr Asp Cys Ser Gln Phe Pro Glu Glu Asn Ser Asp Asn Gln Thr
                405                 410                 415
Cys Leu Met Pro Asp Glu Tyr Val Glu Glu Cys Ser Pro Ser His Phe
                420                 425                 430
Lys Cys Arg Ser Gly Gln Cys Val Leu Ala Ser Arg Cys Asp Gly
                435                 440                 445
Gln Ala Asp Cys Asp Asp Ser Asp Glu Glu Asn Cys Gly Cys Lys
    450                 455                 460
Glu Arg Asp Leu Trp Glu Cys Pro Ser Asn Lys Gln Cys Leu Lys His
465                 470                 475                 480
Thr Val Ile Cys Asp Gly Phe Pro Asp Cys Pro Asp Tyr Met Asp Glu
                485                 490                 495
Lys Asn Cys Ser Phe Cys Gln Asp Asp Glu Leu Glu Cys Ala Asn His
                500                 505                 510
Ala Cys Val Ser Arg Asp Leu Trp Cys Asp Gly Glu Ala Asp Cys Ser
                515                 520                 525
Asp Ser Ser Asp Glu Trp Asp Cys Val Thr Leu Ser Ile Asn Val Asn
530                 535                 540
Ser Ser Ser Phe Leu Met Val His Arg Ala Ala Thr Glu His His Val
545                 550                 555                 560
Cys Ala Asp Gly Trp Gln Glu Ile Leu Ser Gln Leu Ala Cys Lys Gln
                565                 570                 575
Met Gly Leu Gly Glu Pro Ser Val Thr Lys Leu Ile Gln Glu Gln Glu
                580                 585                 590
Lys Glu Pro Arg Trp Leu Thr Leu His Ser Asn Trp Glu Ser Leu Asn
                595                 600                 605
Gly Thr Thr Leu His Glu Leu Leu Val Asn Gly Gln Ser Cys Glu Ser
    610                 615                 620
Arg Ser Lys Ile Ser Leu Leu Cys Thr Lys Gln Asp Cys Gly Arg Arg
625                 630                 635                 640
Pro Ala Ala Arg Met Asn Lys Arg Ile Leu Gly Gly Arg Thr Ser Arg
                645                 650                 655
Pro Gly Arg Trp Pro Trp Gln Cys Ser Leu Gln Ser Glu Pro Ser Gly
                660                 665                 670
His Ile Cys Gly Cys Val Leu Ile Ala Lys Lys Trp Val Leu Thr Val
                675                 680                 685
Ala His Cys Phe Glu Gly Arg Glu Asn Ala Ala Val Trp Lys Val Val
    690                 695                 700
Leu Gly Ile Asn Asn Leu Asp His Pro Ser Val Phe Met Gln Thr Arg
705                 710                 715                 720
Phe Val Lys Thr Ile Ile Leu His Pro Arg Tyr Ser Arg Ala Val Val
                725                 730                 735
Asp Tyr Asp Ile Ser Ile Val Glu Leu Ser Glu Asp Ile Ser Glu Thr
                740                 745                 750
Gly Tyr Val Arg Pro Val Cys Leu Pro Asn Pro Glu Gln Trp Leu Glu
                755                 760                 765
Pro Asp Thr Tyr Cys Tyr Ile Thr Gly Trp Gly His Met Gly Asn Lys
    770                 775                 780
Met Pro Phe Lys Leu Gln Glu Gly Glu Val Arg Ile Ile Ser Leu Glu
```

```
                785                 790                 795                 800
His Cys Gln Ser Tyr Phe Asp Met Lys Thr Ile Thr Thr Arg Met Ile
                    805                 810                 815

Cys Ala Gly Tyr Glu Ser Gly Thr Val Asp Ser Cys Met Gly Asp Ser
                820                 825                 830

Gly Gly Pro Leu Val Cys Glu Lys Pro Gly Gly Arg Trp Thr Leu Phe
                835                 840                 845

Gly Leu Thr Ser Trp Gly Ser Val Cys Phe Ser Lys Val Leu Gly Pro
            850                 855                 860

Gly Val Tyr Ser Asn Val Ser Tyr Phe Val Glu Trp Ile Lys Arg Gln
865                 870                 875                 880

Ile Tyr Ile Gln Thr Phe Leu Leu Asn
                885

<210> SEQ ID NO 23
<211> LENGTH: 39
<212> TYPE: DNA
<213> ORGANISM: Artificial
<220> FEATURE:
<223> OTHER INFORMATION: Reverse Primer Del 72

<400> SEQUENCE: 23
ggggctcgag aggtgagaag caaattctgc tgacattgc                          39

<210> SEQ ID NO 24
<211> LENGTH: 38
<212> TYPE: DNA
<213> ORGANISM: Artificial
<220> FEATURE:
<223> OTHER INFORMATION: Forwrd Primer Del 71

<400> SEQUENCE: 24
ggggctcgag acctgcctga tgcctgatga atatgtgg                           38

<210> SEQ ID NO 25
<211> LENGTH: 925
<212> TYPE: PRT
<213> ORGANISM: Artificial
<220> FEATURE:
<223> OTHER INFORMATION: Corin AA 1 to 449, Artifical XhoI Site, and
      Corin AA 569 to 1042

<400> SEQUENCE: 25

Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
            100                 105                 110

His Pro Asp Gln His Val Pro Ala Trp Thr Thr Asp Ala Ser Leu Pro
        115                 120                 125
```

```
Gly Asp Gln Ser His Arg Asn Thr Ser Ala Cys Met Asn Ile Thr His
    130                 135                 140
Ser Gln Cys Gln Met Leu Pro Tyr His Ala Thr Leu Thr Pro Leu Leu
145                 150                 155                 160
Ser Val Val Arg Asn Met Glu Met Glu Lys Phe Leu Lys Phe Phe Thr
                165                 170                 175
Tyr Leu His Arg Leu Ser Cys Tyr Gln His Ile Met Leu Phe Gly Cys
            180                 185                 190
Thr Leu Ala Phe Pro Glu Cys Ile Ile Asp Gly Asp Ser His Gly
        195                 200                 205
Leu Leu Pro Cys Arg Ser Phe Cys Glu Ala Ala Lys Glu Gly Cys Glu
    210                 215                 220
Ser Val Leu Gly Met Val Asn Tyr Ser Trp Pro Asp Phe Leu Arg Cys
225                 230                 235                 240
Ser Gln Phe Arg Asn Gln Thr Glu Ser Ser Asn Val Ser Arg Ile Cys
                245                 250                 255
Phe Ser Pro Gln Gln Glu Asn Gly Lys Gln Leu Leu Cys Gly Arg Gly
            260                 265                 270
Glu Asn Phe Leu Cys Ala Ser Gly Ile Cys Ile Pro Gly Lys Leu Gln
        275                 280                 285
Cys Asn Gly Tyr Asn Asp Cys Asp Asp Trp Ser Asp Glu Ala His Cys
    290                 295                 300
Asn Cys Ser Glu Asn Leu Phe His Cys His Thr Gly Lys Cys Leu Asn
305                 310                 315                 320
Tyr Ser Leu Val Cys Asp Gly Tyr Asp Asp Cys Gly Asp Leu Ser Asp
                325                 330                 335
Glu Gln Asn Cys Asp Cys Asn Pro Thr Thr Glu His Arg Cys Gly Asp
            340                 345                 350
Gly Arg Cys Ile Ala Met Glu Trp Val Cys Asp Gly Asp His Asp Cys
        355                 360                 365
Val Asp Lys Ser Asp Glu Val Asn Cys Ser Cys His Ser Gln Gly Leu
    370                 375                 380
Val Glu Cys Arg Asn Gly Gln Cys Ile Pro Ser Thr Phe Gln Cys Asp
385                 390                 395                 400
Gly Asp Glu Asp Cys Lys Asp Gly Ser Asp Glu Glu Asn Cys Ser Val
                405                 410                 415
Ile Gln Thr Ser Cys Gln Glu Gly Asp Gln Arg Cys Leu Tyr Asn Pro
            420                 425                 430
Cys Leu Asp Ser Cys Gly Gly Ser Ser Leu Cys Asp Pro Asn Asn Ser
        435                 440                 445
Leu Leu Glu Thr Cys Leu Met Pro Asp Glu Tyr Val Glu Glu Cys Ser
    450                 455                 460
Pro Ser His Phe Lys Cys Arg Ser Gly Gln Cys Val Leu Ala Ser Arg
465                 470                 475                 480
Arg Cys Asp Gly Gln Ala Asp Cys Asp Asp Asp Ser Asp Glu Glu Asn
                485                 490                 495
Cys Gly Cys Lys Glu Arg Asp Leu Trp Glu Cys Pro Ser Asn Lys Gln
            500                 505                 510
Cys Leu Lys His Thr Val Ile Cys Asp Gly Phe Pro Asp Cys Pro Asp
        515                 520                 525
Tyr Met Asp Glu Lys Asn Cys Ser Phe Cys Gln Asp Asp Glu Leu Glu
    530                 535                 540
Cys Ala Asn His Ala Cys Val Ser Arg Asp Leu Trp Cys Asp Gly Glu
```

```
                545                 550                 555                 560
Ala Asp Cys Ser Asp Ser Ser Asp Glu Trp Asp Cys Val Thr Leu Ser
                565                     570                 575

Ile Asn Val Asn Ser Ser Ser Phe Leu Met Val His Arg Ala Ala Thr
            580                     585                 590

Glu His His Val Cys Ala Asp Gly Trp Gln Glu Ile Leu Ser Gln Leu
        595                     600                 605

Ala Cys Lys Gln Met Gly Leu Gly Glu Pro Ser Val Thr Lys Leu Ile
    610                     615                 620

Gln Glu Gln Glu Lys Glu Pro Arg Trp Leu Thr Leu His Ser Asn Trp
625                     630                 635                 640

Glu Ser Leu Asn Gly Thr Thr Leu His Glu Leu Leu Val Asn Gly Gln
                645                 650                 655

Ser Cys Glu Ser Arg Ser Lys Ile Ser Leu Leu Cys Thr Lys Gln Asp
                660                 665                 670

Cys Gly Arg Arg Pro Ala Ala Arg Met Asn Lys Arg Ile Leu Gly Gly
            675                 680                 685

Arg Thr Ser Arg Pro Gly Arg Trp Pro Trp Gln Cys Ser Leu Gln Ser
    690                 695                 700

Glu Pro Ser Gly His Ile Cys Gly Cys Val Leu Ile Ala Lys Lys Trp
705                 710                 715                 720

Val Leu Thr Val Ala His Cys Phe Glu Gly Arg Glu Asn Ala Ala Val
                725                 730                 735

Trp Lys Val Val Leu Gly Ile Asn Asn Leu Asp His Pro Ser Val Phe
            740                 745                 750

Met Gln Thr Arg Phe Val Lys Thr Ile Ile Leu His Pro Arg Tyr Ser
        755                 760                 765

Arg Ala Val Val Asp Tyr Asp Ile Ser Ile Val Glu Leu Ser Glu Asp
    770                 775                 780

Ile Ser Glu Thr Gly Tyr Val Arg Pro Val Cys Leu Pro Asn Pro Glu
785                 790                 795                 800

Gln Trp Leu Glu Pro Asp Thr Tyr Cys Tyr Ile Thr Gly Trp Gly His
                805                 810                 815

Met Gly Asn Lys Met Pro Phe Lys Leu Gln Glu Gly Glu Val Arg Ile
            820                 825                 830

Ile Ser Leu Glu His Cys Gln Ser Tyr Phe Asp Met Lys Thr Ile Thr
        835                 840                 845

Thr Arg Met Ile Cys Ala Gly Tyr Glu Ser Gly Thr Val Asp Ser Cys
    850                 855                 860

Met Gly Asp Ser Gly Gly Pro Leu Val Cys Glu Lys Pro Gly Gly Arg
865                 870                 875                 880

Trp Thr Leu Phe Gly Leu Thr Ser Trp Gly Ser Val Cys Phe Ser Lys
                885                 890                 895

Val Leu Gly Pro Gly Val Tyr Ser Asn Val Ser Tyr Phe Val Glu Trp
            900                 905                 910

Ile Lys Arg Gln Ile Tyr Ile Gln Thr Phe Leu Leu Asn
        915                 920                 925

<210> SEQ ID NO 26
<211> LENGTH: 27
<212> TYPE: DNA
<213> ORGANISM: Artificial
<220> FEATURE:
<223> OTHER INFORMATION: Forward Primer EntPCR1a
```

<210> SEQ ID NO 27
<211> LENGTH: 47
<212> TYPE: DNA
<213> ORGANISM: Artificial
<220> FEATURE:
<223> OTHER INFORMATION: Reverse Primer EntPCR1b

<400> SEQUENCE: 27
cctccaagga tcttatcgtc atcgtcccca cagtcttgtt tagtaca        47

<210> SEQ ID NO 28
<211> LENGTH: 27
<212> TYPE: DNA
<213> ORGANISM: Artificial
<220> FEATURE:
<223> OTHER INFORMATION: Forward Primer EntPCR2a

<400> SEQUENCE: 28
ggtttaaacg ggcccttagt ttaggag        27

<210> SEQ ID NO 29
<211> LENGTH: 38
<212> TYPE: DNA
<213> ORGANISM: Artificial
<220> FEATURE:
<223> OTHER INFORMATION: Reverse Primer EntPCR2b

<400> SEQUENCE: 29
gacgatgacg ataagatcct tggaggtcgg acgagtcg        38

<210> SEQ ID NO 30
<211> LENGTH: 1039
<212> TYPE: PRT
<213> ORGANISM: Artificial
<220> FEATURE:
<223> OTHER INFORMATION: Corin AA 1 to 123, Artificial XhoI Site, Corin
      AA 124 to 791, Enterokinase Site, and Corin AA 802 to 1042

<400> SEQUENCE: 30

Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
            100                 105                 110

His Pro Asp Gln His Val Pro Ala Trp Thr Thr Leu Glu Asp Ala Ser
        115                 120                 125

Leu Pro Gly Asp Gln Ser His Arg Asn Thr Ser Ala Cys Met Asn Ile
    130                 135                 140

Thr His Ser Gln Cys Gln Met Leu Pro Tyr His Ala Thr Leu Thr Pro

```
                145                 150                 155                 160
Leu Leu Ser Val Val Arg Asn Met Glu Met Glu Lys Phe Leu Lys Phe
                    165                 170                 175
Phe Thr Tyr Leu His Arg Leu Ser Cys Tyr Gln His Ile Met Leu Phe
                    180                 185                 190
Gly Cys Thr Leu Ala Phe Pro Glu Cys Ile Ile Asp Gly Asp Asp Ser
                    195                 200                 205
His Gly Leu Leu Pro Cys Arg Ser Phe Cys Glu Ala Ala Lys Glu Gly
                    210                 215                 220
Cys Glu Ser Val Leu Gly Met Val Asn Tyr Ser Trp Pro Asp Phe Leu
225                 230                 235                 240
Arg Cys Ser Gln Phe Arg Asn Gln Thr Glu Ser Ser Asn Val Ser Arg
                    245                 250                 255
Ile Cys Phe Ser Pro Gln Gln Glu Asn Gly Lys Gln Leu Leu Cys Gly
                    260                 265                 270
Arg Gly Glu Asn Phe Leu Cys Ala Ser Gly Ile Cys Ile Pro Gly Lys
                    275                 280                 285
Leu Gln Cys Asn Gly Tyr Asn Asp Cys Asp Asp Trp Ser Asp Glu Ala
        290                 295                 300
His Cys Asn Cys Ser Glu Asn Leu Phe His Cys His Thr Gly Lys Cys
305                 310                 315                 320
Leu Asn Tyr Ser Leu Val Cys Asp Gly Tyr Asp Asp Cys Gly Asp Leu
                    325                 330                 335
Ser Asp Glu Gln Asn Cys Asp Cys Asn Pro Thr Thr Glu His Arg Cys
                    340                 345                 350
Gly Asp Gly Arg Cys Ile Ala Met Glu Trp Val Cys Asp Gly Asp His
                    355                 360                 365
Asp Cys Val Asp Lys Ser Asp Glu Val Asn Cys Ser Cys His Ser Gln
        370                 375                 380
Gly Leu Val Glu Cys Arg Asn Gly Gln Cys Ile Pro Ser Thr Phe Gln
385                 390                 395                 400
Cys Asp Gly Asp Glu Asp Cys Lys Asp Gly Ser Asp Glu Glu Asn Cys
                    405                 410                 415
Ser Val Ile Gln Thr Ser Cys Gln Glu Gly Asp Gln Arg Cys Leu Tyr
                    420                 425                 430
Asn Pro Cys Leu Asp Ser Cys Gly Gly Ser Ser Leu Cys Asp Pro Asn
                    435                 440                 445
Asn Ser Leu Asn Cys Ser Gln Cys Glu Pro Ile Thr Leu Glu Leu
        450                 455                 460
Cys Met Asn Leu Pro Tyr Asn Ser Thr Ser Tyr Pro Asn Tyr Phe Gly
465                 470                 475                 480
His Arg Thr Gln Lys Glu Ala Ser Ile Ser Trp Glu Ser Ser Leu Phe
                    485                 490                 495
Pro Ala Leu Val Gln Thr Asn Cys Tyr Lys Tyr Leu Met Phe Phe Ser
                    500                 505                 510
Cys Thr Ile Leu Val Pro Lys Cys Asp Val Asn Thr Gly Glu Arg Ile
            515                 520                 525
Pro Pro Cys Arg Ala Leu Cys Glu His Ser Lys Glu Arg Cys Glu Ser
            530                 535                 540
Val Leu Gly Ile Val Gly Leu Gln Trp Pro Glu Asp Thr Asp Cys Ser
545                 550                 555                 560
Gln Phe Pro Glu Glu Asn Ser Asp Asn Gln Thr Cys Leu Met Pro Asp
                    565                 570                 575
```

```
Glu Tyr Val Glu Glu Cys Ser Pro Ser His Phe Lys Cys Arg Ser Gly
            580                 585                 590

Gln Cys Val Leu Ala Ser Arg Arg Cys Asp Gly Gln Ala Asp Cys Asp
        595                 600                 605

Asp Asp Ser Asp Glu Glu Asn Cys Gly Cys Lys Glu Arg Asp Leu Trp
        610                 615                 620

Glu Cys Pro Ser Asn Lys Gln Cys Leu Lys His Thr Val Ile Cys Asp
625                 630                 635                 640

Gly Phe Pro Asp Cys Pro Asp Tyr Met Asp Glu Lys Asn Cys Ser Phe
            645                 650                 655

Cys Gln Asp Asp Glu Leu Glu Cys Ala Asn His Ala Cys Val Ser Arg
            660                 665                 670

Asp Leu Trp Cys Asp Gly Glu Ala Asp Cys Ser Asp Ser Ser Asp Glu
            675                 680                 685

Trp Asp Cys Val Thr Leu Ser Ile Asn Val Asn Ser Ser Ser Phe Leu
        690                 695                 700

Met Val His Arg Ala Ala Thr Glu His His Val Cys Ala Asp Gly Trp
705                 710                 715                 720

Gln Glu Ile Leu Ser Gln Leu Ala Cys Lys Gln Met Gly Leu Gly Glu
                725                 730                 735

Pro Ser Val Thr Lys Leu Ile Gln Glu Gln Lys Glu Pro Arg Trp
            740                 745                 750

Leu Thr Leu His Ser Asn Trp Glu Ser Leu Asn Gly Thr Thr Leu His
                755                 760                 765

Glu Leu Leu Val Asn Gly Gln Ser Cys Glu Ser Arg Ser Lys Ile Ser
    770                 775                 780

Leu Leu Cys Thr Lys Gln Asp Cys Gly Asp Asp Asp Lys Ile Leu
785                 790                 795                 800

Gly Gly Arg Thr Ser Arg Pro Gly Arg Trp Pro Trp Gln Cys Ser Leu
                805                 810                 815

Gln Ser Glu Pro Ser Gly His Ile Cys Gly Cys Val Leu Ile Ala Lys
            820                 825                 830

Lys Trp Val Leu Thr Val Ala His Cys Phe Glu Gly Arg Glu Asn Ala
        835                 840                 845

Ala Val Trp Lys Val Val Leu Gly Ile Asn Asn Leu Asp His Pro Ser
    850                 855                 860

Val Phe Met Gln Thr Arg Phe Val Lys Thr Ile Ile Leu His Pro Arg
865                 870                 875                 880

Tyr Ser Arg Ala Val Val Asp Tyr Asp Ile Ser Ile Val Glu Leu Ser
            885                 890                 895

Glu Asp Ile Ser Glu Thr Gly Tyr Val Arg Pro Val Cys Leu Pro Asn
            900                 905                 910

Pro Glu Gln Trp Leu Glu Pro Asp Thr Tyr Cys Tyr Ile Thr Gly Trp
            915                 920                 925

Gly His Met Gly Asn Lys Met Pro Phe Lys Leu Gln Glu Gly Glu Val
        930                 935                 940

Arg Ile Ile Ser Leu Glu His Cys Gln Ser Tyr Phe Asp Met Lys Thr
945                 950                 955                 960

Ile Thr Thr Arg Met Ile Cys Ala Gly Tyr Glu Ser Gly Thr Val Asp
                965                 970                 975

Ser Cys Met Gly Asp Ser Gly Gly Pro Leu Val Cys Glu Lys Pro Gly
            980                 985                 990
```

```
Gly Arg Trp Thr Leu Phe Gly Leu  Thr Ser Trp Gly Ser  Val Cys Phe
        995                 1000                 1005

Ser Lys  Val Leu Gly Pro Gly  Val Tyr Ser Asn Val  Ser Tyr Phe
    1010                 1015                 1020

Val Glu  Trp Ile Lys Arg Gln  Ile Tyr Ile Gln Thr  Phe Leu Leu
    1025                 1030                 1035

Asn

<210> SEQ ID NO 31
<211> LENGTH: 43
<212> TYPE: DNA
<213> ORGANISM: Artificial
<220> FEATURE:
<223> OTHER INFORMATION: Forward Primer CorFL-1

<400> SEQUENCE: 31
ggggctcgag gatgcttctc tcccagggga ccaaagtcac agg          43

<210> SEQ ID NO 32
<211> LENGTH: 40
<212> TYPE: DNA
<213> ORGANISM: Artificial
<220> FEATURE:
<223> OTHER INFORMATION: Reverse Primer CorSol2Apa2

<400> SEQUENCE: 32
ggggggcccc gtttaggaga aaggtctgga tgtaaatctg              40

<210> SEQ ID NO 33
<211> LENGTH: 2976
<212> TYPE: DNA
<213> ORGANISM: Artificial
<220> FEATURE:
<223> OTHER INFORMATION: SolCorin-EK DNA Sequence

<400> SEQUENCE: 33
atggagacag acacactcct gctatgggta ctgctgctct ggttccagg ttccactggt    60 gacgcggccc agccggccag gcgcgcgcgc cgtacgaagc tcgcccttct cgaggatgct   120
tctctcccag gggaccaaag tcacaggaat acaagtgcct gtatgaacat cacccacagc   180
cagtgtcaga tgctgcccta ccacgccacg ctgacacctc tcctctcagt tgtcagaaac   240
atggaaatgg aaaagttcct caagtttttc acatatctcc atcgcctcag ttgctatcaa   300
catatcatgc tgtttggctg taccctcgcc ttccctgagt gcatcattga tggcgatgac   360
agtcatggac tcctgccctg taggtccttc tgtgaggctg caaagaagg ctgtgaatca   420 gtcctgggga tggtgaatta ctcctggccg gatttcctca gatgctccca gtttagaaac   480
caaactgaaa gcagcaatgt cagcagaatt gcttctcac ctcagcagga aaacggaaag   540
caattgctct gtggaagggg tgagaacttt ctgtgtgcca gtggaatctg catccccggg   600
aaactgcaat gtaatggcta caacgactgt gacgactgga tgacgaggc tcattgcaac   660 tgcagcgaga atctgtttca ctgtcacaca ggcaagtgcc ttaattacag ccttgtgtgt   720
gatggatatg atgactgtgg ggattt gagt gatgagcaaa actgtgattg caatcccaca   780
acagagcatc gctgcgggga cgggcgctgc atcgccatgg agtgggtgtg tgatggtgac   840
cacgactgtg tggataagtc tgacgaggtc aactgctcct gtcacagcca gggtctggtg   900
gaatgcagaa atgacaatg tatcccagc acgtttcaat gtgatggtga cgaggactgc   960
aaggatggga gtgatgagga aactgcagc gtcattcaga cttcatgtca agaaggagac  1020
```

-continued

```
caaagatgcc tctacaatcc ctgccttgat tcatgtggtg gtagctctct ctgtgacccg    1080
aacaacagtc tgaataactg tagtcaatgt gaaccaatta cattggaact ctgcatgaat    1140
ttgccctaca acagtacaag ttatccaaat tattttggcc acaggactca aaaggaagca    1200
tccatcagct gggagtcttc tcttttccct gcacttgttc aaaccaactg ttataaatac    1260
ctcatgttct tttcttgcac cattttggta ccaaaatgtg atgtgaatac aggcgagcgt    1320
atccctcctt gcagggcatt gtgtgaacac tctaaagaac gctgtgagtc tgttcttggg    1380
attgtgggcc tacagtggcc tgaagacaca gattgcagtc aatttccaga ggaaaattca    1440
gacaatcaaa cctgcctgat gcctgatgaa tatgtggaag aatgctcacc tagtcatttc    1500
aagtgccgct caggacagtg tgttctggct tccagaagat gtgatggcca ggccgactgt    1560
gacgatgaca gtgatgagga aaactgtggt tgtaaagaga gagatctttg gaatgtccca    1620
tccaataaac aatgtttgaa gcacacagtg atctgcgatg ggttcccaga ctgccctgat    1680
tacatggacg agaaaaactg ctcatttgc caagatgatg agctggaatg tgcaaaccat    1740
gcgtgtgtgt cacgtgacct gtggtgtgat ggtgaagccg actgctcaga cagttcagat    1800
gaatgggact gtgtgaccct ctctataaat gtgaactcct cttcctttct gatggttcac    1860
agagctgcca cagaacacca cgtgtgtgca gatggctggc aggagatatt gagtcagctg    1920
gcctgcaagc agatgggttt aggagaacca tctgtgacca aattgataca ggaacaggag    1980
aaagagccgc ggtggctgac attacactcc aactgggaga gcctcaatgg gaccacttta    2040
catgaacttc tagtaaatgg gcagtcttgt gagagcagaa gtaaaatttc tcttctgtgt    2100
actaaacaag actgtgggcg ccgccctgct gccgacgatg acgataagat ccttggaggt    2160
cggacgagtc gccctggaag gtggccatgg cagtgttctc tgcagagtga acccagtgga    2220
catatctgtg gctgtgtcct cattgccaag aagtgggttc tgacagttgc ccactgcttc    2280
gaggggagag agaatgctgc agtttggaaa gtggtgcttg gcatcaacaa tctagaccat    2340
ccatcagtgt tcatgcagac acgctttgtg aagaccatca tcctgcatcc ccgctacagt    2400
cgagcagtgg tggactatga catcagcatc gttgagctga gtgaagacat cagtgagact    2460
ggctacgtcc ggcctgtctg cttgcccaac ccggagcagt ggctagagcc tgacacgtac    2520
tgctatatca caggctgggg ccacatgggc aataaaatgc catttaagct gcaagaggga    2580
gaggtccgca ttatttctct ggaacattgt cagtcctact ttgacatgaa gaccatcacc    2640
actcggatga tatgtgctgg ctatgagtct ggcacagttg attcatgcat gggtgacagc    2700
ggtgggcctc ttgtttgtga aagcctgga ggacggtgga cattatttgg attaacttca    2760
tggggctccg tctgcttttc caaagtcctg gggcctggcg tttatagtaa tgtgtcatat    2820
ttcgtcgaat ggattaaaag acagatttac atccagacct ttctcctaaa caagggcgag    2880
cttggtaccg agctcggatc cgaaggtaag cctatcccta accctctcct cggtctcgat    2940
tctacgcgta ccggtcatca tcaccatcac cattga                             2976
```

<210> SEQ ID NO 34
<211> LENGTH: 991
<212> TYPE: PRT
<213> ORGANISM: Artificial
<220> FEATURE:
<223> OTHER INFORMATION: IgK Secretion Signal Sequence, Artificial XhoI
      Site, Corin AA 124 to 796, Enterokinase Site, Corin AA 802 to
      1042, and C-Terminal V5 and 6xHis Tags

<400> SEQUENCE: 34

Met Glu Thr Asp Thr Leu Leu Leu Trp Val Leu Leu Leu Trp Val Pro

-continued

```
1               5                   10                  15
Gly Ser Thr Gly Asp Ala Ala Gln Pro Ala Arg Arg Ala Arg Arg Thr
                20                  25                  30
Lys Leu Ala Leu Leu Glu Asp Ala Ser Leu Pro Gly Asp Gln Ser His
                35                  40              45
Arg Asn Thr Ser Ala Cys Met Asn Ile Thr His Ser Gln Cys Gln Met
 50                 55                  60
Leu Pro Tyr His Ala Thr Leu Thr Pro Leu Leu Ser Val Val Arg Asn
 65                 70                  75                  80
Met Glu Met Glu Lys Phe Leu Lys Phe Thr Tyr Leu His Arg Leu
                 85                  90                  95
Ser Cys Tyr Gln His Ile Met Leu Phe Gly Cys Thr Leu Ala Phe Pro
                100                 105                 110
Glu Cys Ile Ile Asp Gly Asp Ser His Gly Leu Leu Pro Cys Arg
                115                 120                 125
Ser Phe Cys Glu Ala Ala Lys Glu Gly Cys Glu Ser Val Leu Gly Met
                130                 135                 140
Val Asn Tyr Ser Trp Pro Asp Phe Leu Arg Cys Ser Gln Phe Arg Asn
145                 150                 155                 160
Gln Thr Glu Ser Ser Asn Val Ser Arg Ile Cys Phe Ser Pro Gln Gln
                165                 170                 175
Glu Asn Gly Lys Gln Leu Leu Cys Gly Arg Gly Glu Asn Phe Leu Cys
                180                 185                 190
Ala Ser Gly Ile Cys Ile Pro Gly Lys Leu Gln Cys Asn Gly Tyr Asn
                195                 200                 205
Asp Cys Asp Asp Trp Ser Asp Glu Ala His Cys Asn Cys Ser Glu Asn
                210                 215                 220
Leu Phe His Cys His Thr Gly Lys Cys Leu Asn Tyr Ser Leu Val Cys
225                 230                 235                 240
Asp Gly Tyr Asp Asp Cys Gly Asp Leu Ser Asp Glu Gln Asn Cys Asp
                245                 250                 255
Cys Asn Pro Thr Thr Glu His Arg Cys Gly Asp Gly Arg Cys Ile Ala
                260                 265                 270
Met Glu Trp Val Cys Asp Gly Asp His Asp Cys Val Asp Lys Ser Asp
                275                 280                 285
Glu Val Asn Cys Ser Cys His Ser Gln Gly Leu Val Glu Cys Arg Asn
                290                 295                 300
Gly Gln Cys Ile Pro Ser Thr Phe Gln Cys Asp Gly Asp Glu Asp Cys
305                 310                 315                 320
Lys Asp Gly Ser Asp Glu Glu Asn Cys Ser Val Ile Gln Thr Ser Cys
                325                 330                 335
Gln Glu Gly Asp Gln Arg Cys Leu Tyr Asn Pro Cys Leu Asp Ser Cys
                340                 345                 350
Gly Gly Ser Ser Leu Cys Asp Pro Asn Asn Ser Leu Asn Asn Cys Ser
                355                 360                 365
Gln Cys Glu Pro Ile Thr Leu Glu Leu Cys Met Asn Leu Pro Tyr Asn
                370                 375                 380
Ser Thr Ser Tyr Pro Asn Tyr Phe Gly His Arg Thr Gln Lys Glu Ala
385                 390                 395                 400
Ser Ile Ser Trp Glu Ser Ser Leu Phe Pro Ala Leu Val Gln Thr Asn
                405                 410                 415
Cys Tyr Lys Tyr Leu Met Phe Phe Ser Cys Thr Ile Leu Val Pro Lys
                420                 425                 430
```

-continued

```
Cys Asp Val Asn Thr Gly Glu Arg Ile Pro Pro Cys Arg Ala Leu Cys
            435                 440                 445
Glu His Ser Lys Glu Arg Cys Glu Ser Val Leu Gly Ile Val Gly Leu
450                 455                 460
Gln Trp Pro Glu Asp Thr Asp Cys Ser Gln Phe Pro Glu Glu Asn Ser
465                 470                 475                 480
Asp Asn Gln Thr Cys Leu Met Pro Asp Glu Tyr Val Glu Glu Cys Ser
            485                 490                 495
Pro Ser His Phe Lys Cys Arg Ser Gly Gln Cys Val Leu Ala Ser Arg
                500                 505                 510
Arg Cys Asp Gly Gln Ala Asp Cys Asp Asp Asp Ser Asp Glu Glu Asn
    515                 520                 525
Cys Gly Cys Lys Glu Arg Asp Leu Trp Glu Cys Pro Ser Asn Lys Gln
530                 535                 540
Cys Leu Lys His Thr Val Ile Cys Asp Gly Phe Pro Asp Cys Pro Asp
545                 550                 555                 560
Tyr Met Asp Glu Lys Asn Cys Ser Phe Cys Gln Asp Asp Glu Leu Glu
            565                 570                 575
Cys Ala Asn His Ala Cys Val Ser Arg Asp Leu Trp Cys Asp Gly Glu
                580                 585                 590
Ala Asp Cys Ser Asp Ser Ser Asp Glu Trp Asp Cys Val Thr Leu Ser
    595                 600                 605
Ile Asn Val Asn Ser Ser Phe Leu Met Val His Arg Ala Ala Thr
610                 615                 620
Glu His His Val Cys Ala Asp Gly Trp Gln Glu Ile Leu Ser Gln Leu
625                 630                 635                 640
Ala Cys Lys Gln Met Gly Leu Gly Glu Pro Ser Val Thr Lys Leu Ile
            645                 650                 655
Gln Glu Gln Glu Lys Glu Pro Arg Trp Leu Thr Leu His Ser Asn Trp
                660                 665                 670
Glu Ser Leu Asn Gly Thr Thr Leu His Glu Leu Leu Val Asn Gly Gln
    675                 680                 685
Ser Cys Glu Ser Arg Ser Lys Ile Ser Leu Leu Cys Thr Lys Gln Asp
690                 695                 700
Cys Gly Arg Arg Pro Ala Ala Asp Asp Asp Lys Ile Leu Gly Gly
705                 710                 715                 720
Arg Thr Ser Arg Pro Gly Arg Trp Pro Trp Gln Cys Ser Leu Gln Ser
            725                 730                 735
Glu Pro Ser Gly His Ile Cys Gly Cys Val Leu Ile Ala Lys Lys Trp
                740                 745                 750
Val Leu Thr Val Ala His Cys Phe Glu Gly Arg Glu Asn Ala Ala Val
    755                 760                 765
Trp Lys Val Val Leu Gly Ile Asn Asn Leu Asp His Pro Ser Val Phe
770                 775                 780
Met Gln Thr Arg Phe Val Lys Thr Ile Ile Leu His Pro Arg Tyr Ser
785                 790                 795                 800
Arg Ala Val Val Asp Tyr Asp Ile Ser Ile Val Glu Leu Ser Glu Asp
            805                 810                 815
Ile Ser Glu Thr Gly Tyr Val Arg Pro Val Cys Leu Pro Asn Pro Glu
                820                 825                 830
Gln Trp Leu Glu Pro Asp Thr Tyr Cys Tyr Ile Thr Gly Trp Gly His
    835                 840                 845
```

Met Gly Asn Lys Met Pro Phe Lys Leu Gln Glu Gly Glu Val Arg Ile
    850                 855                 860

Ile Ser Leu Glu His Cys Gln Ser Tyr Phe Asp Met Lys Thr Ile Thr
865                 870                 875                 880

Thr Arg Met Ile Cys Ala Gly Tyr Glu Ser Gly Thr Val Asp Ser Cys
            885                 890                 895

Met Gly Asp Ser Gly Gly Pro Leu Val Cys Glu Lys Pro Gly Gly Arg
            900                 905                 910

Trp Thr Leu Phe Gly Leu Thr Ser Trp Gly Ser Val Cys Phe Ser Lys
                915                 920                 925

Val Leu Gly Pro Gly Val Tyr Ser Asn Val Ser Tyr Phe Val Glu Trp
    930                 935                 940

Ile Lys Arg Gln Ile Tyr Ile Gln Thr Phe Leu Leu Asn Lys Gly Glu
945                 950                 955                 960

Leu Gly Thr Glu Leu Gly Ser Glu Gly Lys Pro Ile Pro Asn Pro Leu
                965                 970                 975

Leu Gly Leu Asp Ser Thr Arg Thr Gly His His His His His
            980                 985                 990

<210> SEQ ID NO 35
<211> LENGTH: 46
<212> TYPE: DNA
<213> ORGANISM: Artificial
<220> FEATURE:
<223> OTHER INFORMATION: Forward Primer SolCat1

<400> SEQUENCE: 35
ctgctgccga cgatgacgat aagatccttg gaggtcggac gagtcg        46

<210> SEQ ID NO 36
<211> LENGTH: 45
<212> TYPE: DNA
<213> ORGANISM: Artificial
<220> FEATURE:
<223> OTHER INFORMATION: Forward Primer SolCat2

<400> SEQUENCE: 36
aaacaagact gtgggcgccg ccctgctgcc gacgatgacg ataag         45

<210> SEQ ID NO 37
<211> LENGTH: 326
<212> TYPE: PRT
<213> ORGANISM: Artificial
<220> FEATURE:
<223> OTHER INFORMATION: IgK Secretion Signal Sequence, Corin AA 787 to
      796, Enterokinase Site, Corin AA 802 to 1042, and C-Terminal V5
      and 6xHis Tags

<400> SEQUENCE: 37

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ala Leu Lys Gln Asp Cys Gly Arg Arg Pro Ala Ala Asp Asp
        35                  40                  45

Asp Asp Lys Ile Leu Gly Gly Arg Thr Ser Arg Pro Gly Arg Trp Pro
    50                  55                  60

Trp Gln Cys Ser Leu Gln Ser Glu Pro Ser Gly His Ile Cys Gly Cys
65                  70                  75                  80

Val Leu Ile Ala Lys Lys Trp Val Leu Thr Val Ala His Cys Phe Glu

```
                     85                  90                  95
Gly Arg Glu Asn Ala Ala Val Trp Lys Val Val Leu Gly Ile Asn Asn
                100                 105                 110
Leu Asp His Pro Ser Val Phe Met Gln Thr Arg Phe Val Lys Thr Ile
            115                 120                 125
Ile Leu His Pro Arg Tyr Ser Arg Ala Val Val Asp Tyr Asp Ile Ser
        130                 135                 140
Ile Val Glu Leu Ser Glu Asp Ile Ser Glu Thr Gly Tyr Val Arg Pro
145                 150                 155                 160
Val Cys Leu Pro Asn Pro Glu Gln Trp Leu Glu Pro Asp Thr Tyr Cys
                165                 170                 175
Tyr Ile Thr Gly Trp Gly His Met Gly Asn Lys Met Pro Phe Lys Leu
            180                 185                 190
Gln Glu Gly Glu Val Arg Ile Ile Ser Leu Glu His Cys Gln Ser Tyr
        195                 200                 205
Phe Asp Met Lys Thr Ile Thr Thr Arg Met Ile Cys Ala Gly Tyr Glu
    210                 215                 220
Ser Gly Thr Val Asp Ser Cys Met Gly Asp Ser Gly Gly Pro Leu Val
225                 230                 235                 240
Cys Glu Lys Pro Gly Gly Arg Trp Thr Leu Phe Gly Leu Thr Ser Trp
                245                 250                 255
Gly Ser Val Cys Phe Ser Lys Val Leu Gly Pro Gly Val Tyr Ser Asn
            260                 265                 270
Val Ser Tyr Phe Val Glu Trp Ile Lys Arg Gln Ile Tyr Ile Gln Thr
        275                 280                 285
Phe Leu Leu Asn Lys Gly Glu Leu Gly Thr Glu Leu Gly Ser Glu Gly
    290                 295                 300
Lys Pro Ile Pro Asn Pro Leu Leu Gly Leu Asp Ser Thr Arg Thr Gly
305                 310                 315                 320
His His His His His His
            325

<210> SEQ ID NO 38
<211> LENGTH: 9
<212> TYPE: PRT
<213> ORGANISM: Artificial
<220> FEATURE:
<223> OTHER INFORMATION: Substitute Activation Sequence 1

<400> SEQUENCE: 38

Leu Lys Thr Pro Arg Val Val Gly Gly
1               5

<210> SEQ ID NO 39
<211> LENGTH: 9
<212> TYPE: PRT
<213> ORGANISM: Artificial
<220> FEATURE:
<223> OTHER INFORMATION: Substitute Activation Sequence 2

<400> SEQUENCE: 39

Leu Lys Gln Ala Arg Val Val Gly Gly
1               5

<210> SEQ ID NO 40
<211> LENGTH: 9
<212> TYPE: PRT
<213> ORGANISM: Artificial
<220> FEATURE:
```

-continued

```
<223> OTHER INFORMATION: Substitute Activation Sequence 3

<400> SEQUENCE: 40

Asp Asp Asp Asp Lys Ile Val Gly Gly
1               5

<210> SEQ ID NO 41
<211> LENGTH: 6
<212> TYPE: PRT
<213> ORGANISM: Artificial
<220> FEATURE:
<223> OTHER INFORMATION: Substitute Activation Sequence 4

<400> SEQUENCE: 41

Asp Asp Asp Asp Lys Ile
1               5
```